US012661245B2

(12) United States Patent
Martin

(10) Patent No.: US 12,661,245 B2
(45) Date of Patent: Jun. 23, 2026

(54) PROSTHETIC INTERFACE SYSTEM USING COMPLIANT MEMBERS

(71) Applicant: James Jay Martin, Oklahoma City, OK (US)

(72) Inventor: James Jay Martin, Oklahoma City, OK (US)

( * ) Notice: Subject to any disclaimer, the term of this patent is extended or adjusted under 35 U.S.C. 154(b) by 0 days.

(21) Appl. No.: 18/487,745

(22) Filed: Oct. 16, 2023

(65) Prior Publication Data

US 2024/0277493 A1 Aug. 22, 2024

Related U.S. Application Data

(63) Continuation of application No. 18/131,951, filed on Apr. 7, 2023, now abandoned, which is a continuation of application No. 17/410,121, filed on Aug. 24, 2021, now abandoned, which is a continuation of application No. 16/774,924, filed on Jan. 28, 2020, (Continued)

(51) Int. Cl.
| | |
|---|---|
| *A61F 2/80* | (2006.01) |
| *A61F 2/50* | (2006.01) |
| *A61F 2/60* | (2006.01) |
| *A61F 2/76* | (2006.01) |

(Continued)

(52) U.S. Cl.
CPC .................. *A61F 2/80* (2013.01); *A61F 2/78* (2013.01); *A61F 2/7812* (2013.01); *A61F 2002/5024* (2013.01); *A61F 2002/5027* (2013.01); *A61F 2002/543* (2013.01); *A61F 2002/546* (2013.01); *A61F 2002/608* (2013.01); *A61F 2/76* (2013.01); *A61F 2002/7862* (2013.01)

(58) Field of Classification Search
CPC ...... A61F 2/60; A61F 2/76; A61F 2/78; A61F 2/7843; A61F 2/80; A61F 2002/5016; A61F 2002/5026; A61F 2002/5027; A61F 2002/5083; A61F 2002/608
See application file for complete search history.

(56) References Cited

U.S. PATENT DOCUMENTS

| | | | |
|---|---|---|---|
| 8,323,353 B1 | 12/2012 | Alley et al. | |
| 8,945,237 B2 | 2/2015 | Cornell | |
| 2012/0109031 A1* | 5/2012 | Vollbrecht | ............ A61F 13/085 |
| | | | 602/5 |
| 2012/0311886 A1* | 12/2012 | Reno, III | ............... A43B 3/105 |
| | | | 36/71 |

(Continued)

FOREIGN PATENT DOCUMENTS

DE 1033566 B * 7/1958

OTHER PUBLICATIONS

Translation of DE1033566B. (Year: 1955).*

(Continued)

*Primary Examiner* — Christie Bahena
(74) *Attorney, Agent, or Firm* — Phillips Murrah PC; Martin G. Ozinga

(57) ABSTRACT

A prosthetic or orthotic device using at least one of measurements of residual limb length or circumference to define a prosthetic socket assembly configuration, comprising modular socket components fitted to the individual user's residual limb having a mounting point for an attachment, at least one compliant member attached to at least one stabilizing unit, and at least one second compliant member attached to at least one stabilizing unit wherein the first compliant member and the second compliant member work in cooperation with the stabilizing unit(s) to control bone position and support the limb within the interface.

6 Claims, 71 Drawing Sheets

Related U.S. Application Data now abandoned, which is a continuation of application No. 15/886,419, filed on Feb. 1, 2018, now abandoned, which is a continuation-in-part of application No. 15/436,961, filed on Feb. 20, 2017, now abandoned, which is a continuation of application No. 15/260,936, filed on Sep. 9, 2016, now abandoned, which is a continuation-in-part of application No. 14/708,274, filed on May 10, 2015, now abandoned.

(60) Provisional application No. 62/499,709, filed on Feb. 2, 2017, provisional application No. 61/998,569, filed on Jul. 1, 2014.

(51) Int. Cl.
    *A61F 2/78*        (2006.01)
    *A61F 2/54*        (2006.01)

(56) References Cited

U.S. PATENT DOCUMENTS

| | | | |
|---|---|---|---|
| 2013/0035623 A1* | 2/2013 | Nace | A61F 5/0123 |
| | | | 602/26 |
| 2013/0123940 A1 | 5/2013 | Hurley et al. | |
| 2014/0121783 A1 | 5/2014 | Alley | |

OTHER PUBLICATIONS

Ford (Year: 1986) WO-8604228-A1.*
"Socket-Less Socket." Martin Bionics, Jul. 13, 2016, accessed Mar. 13, 2017 url <web.archive.org/web/20160713120125/http://www.martinbionics.com:80/socket-less-socket/.>.
Martin_Bionics. Socket-less Socket Transfemoral. O&P Edge Magazine Ad. Nov. 2015. (Year: 2015).

* cited by examiner

100

109

109

100

112

111

100

100

100

201

200

206

207

202

201

201

204

203

805

100

100

100
600
210
208A
208B
207
209
FIG. 6A
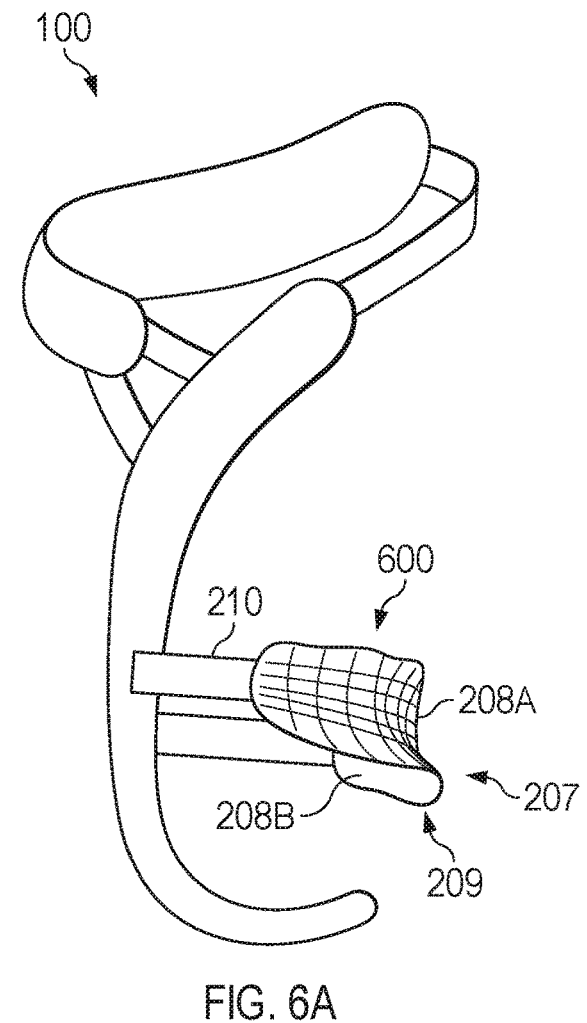
600
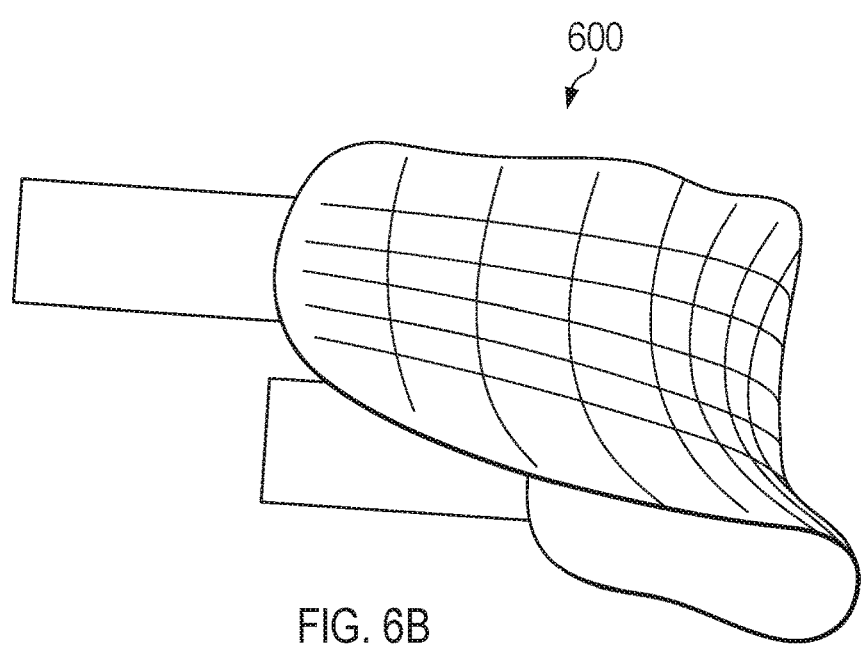
FIG. 6B

Socket-Soft™
Fitting Software

4006

PROSTHETIC INTERFACE SYSTEM USING COMPLIANT MEMBERS

CROSS-REFERENCE TO RELATED APPLICATIONS

The present application is a continuation of Ser. No. 18/131,951, filed on Apr. 7, 2023, currently pending which is a continuation of U.S. patent application Ser. No. 17/410, 121, filed on Aug. 24, 2021, now abandoned, which is a continuation of U.S. patent application Ser. No. 16/774,924, filed on Jan. 28, 2020, now abandoned, which is a continuation of U.S. patent application Ser. No. 15/886,419, filed on Feb. 1, 2018, now abandoned, which claims priority to U.S. Provisional Patent Application Ser. No. 62/499,709 filed Feb. 2, 2017, and which said U.S. patent application Ser. No. 15/886,419 is also a continuation-in-part of U.S. patent application Ser. No. 15/436,961 filed Feb. 20, 2017, now abandoned, which is a continuation of U.S. patent application Ser. No. 15/260,936, filed Sep. 9, 2016, now abandoned, which is a continuation-in-part of U.S. patent application Ser. No. 14/708,274, filed May 10, 2015, now abandoned, which claims priority to U.S. Provisional Patent Application Ser. No. 61/998,569 filed Jul. 1, 2014. Each of the applications listed above is expressly incorporated herein by reference in their entirety.

BACKGROUND OF THE INVENTION

1. Field of the Invention

The present invention relates generally to a limb prosthesis or orthosis for amputees or orthotic users. More particularly, the present invention is a new and improved method for fitting a prosthetic socket or orthotic apparatus and system utilizing simple limb measurements to yield a defined assembly and fitting configuration.

2. Background of the Invention

It is estimated that by the year 2050, the number of amputees will double to over 3.6 Million. American population health concerns are strongly correlated to the weight and age of the individual. The American population and its health patterns show an increase in all high-risk areas as related to dysvascular disease, a leading cause of both stroke and amputation. In the United States, 97% of dysvascular related amputations involve the lower limb.

The aging baby-boomer population is just entering the age where vascular insufficiencies tend to drastically increase, thus, a large influx of stroke patients and amputee patients will be entering the U.S. market alone in the coming few years.

Likewise, there exist over 30,000,000 amputees in developing nations, where less than 5% will have access to well-fitting prosthetics in their lifetime. Three main causes of such a dramatically underserved amputee population in developing nations are A. conventional prosthetics are relatively expensive to fabricate and fit, B. there is a lack of expensive equipment needed to fabricate conventional prosthetics, and C. there is a lack of trained and skilled practitioners who are able to fit them.

The prosthetics market has advanced significantly in recent years-now utilizing many new advanced components such as computer controlled knees and feet. However, the socket interfaces are minimally different from what was being used 20 to 30 years ago. In fact, many of the socket interfaces that are still considered state-of-the-art were originally developed between the 1960's and 1990's, with only minor advancements in materials and suspension methods since then. The core socket interface designs have gone largely unchanged.

There are numerous prosthetic and orthotic companies that provide components for conventional interface designs-ranging from various embodiments of gel liners and suspension aids for prosthetics users. In each of these, the core interface approaches used are antiquated and in desperate need of more advanced methods of how to fit prosthetic devices.

The current state-of-the-art fails to truly accommodate for limb volume changes, has narrow transitions from high force to no force resulting in rubbing and discomfort, and creates a volatile skin environment that is hot and sweaty.

Conventional transfemoral socket shapes hydrostatically compress the residual limb and its tissues into a tight-fitting pre-determined bucket shape, often referred to as a "socket". The lineage of transfemoral design typically include compressing the soft tissue around the underlying muscle-channels and locking around the tuberosity/ramus in various orientations. Conventional socket shapes remain static in size and shape. As the human limb changes in shape and volume, the "key in a keyhole" fit is lost.

The tight fitting nature of conventional interfaces leads to rubbing at the trim lines. At this level, the tissue compression goes from high force to no force over a narrow band, resulting in shear forces on the fragile tissue. The use of rigid or semi-rigid materials in conventional socket interfaces compounds this problem. There is a need for softer, more dynamic materials to be used at transition areas, allowing for compliant transition zones.

The hostile interface environment of conventional prosthetics is hot, full of constant perspiration, lack breathability, and are heavy. As such, many users suffer from various skin conditions including: skin breakdown, pressure sores, heat rash, abrasions, chaffing, dryness, folliculitis, dermatitis, ulcers, eczema, psoriasis, and dry skin. Prosthetics users are desperately searching for better solutions to the many outstanding problems associated with conventional socket interfaces.

The socket interface is by far the most important component of a successful prosthetic or orthotic device. While advanced computer controlled joints are incredibly beneficial for enhancing functional performance, if the socket interface is not stable and comfortable, the high-tech components have little advantage.

Orthotics and prosthetics users are desperately searching for better solutions to the many outstanding problems associated with conventional socket interfaces. Much of the work in advancing the socket comfort has been focused around new materials and suspension capabilities of gel liners, and lighter weight carbon fiber materials. However, the inherent socket interface designs themselves have seen very little change in how they are fit to the patient.

For prosthetics users, the gel liners are a soft padding that resides between the users' limb and the hard socket interface. While these do provide more cushion, they do not address volume change issues, and tend to be very hot, full of perspiration, and make for a hostile environment for the skin. The application of a more advanced compliant-based socket interface approach will greatly enhance the functionality and the daily living for the end user.

Weight Reduction

Prosthetics devices are a significant weight hanging off the body. The Compliant Force Distribution socket interface designs, as disclosed herein, may use compliant materials within its surface area, versus thermoplastic and carbon fiber rigid encapsulated sockets, which are inherently heavier. Thus, the compliant-based socket design may offer a reduction in weight of over 50%.

Keeping the actual weight of prosthetic devices as low as possible is critically important for the efficiency and comfort of the user, but just as important is the perceived weight. The more intrinsic bone motion within the residual limb due to soft tissue pliability in a conventional hydrostatic socket fit results in a significant loss of biomechanical efficiency, and an increase in the perceived weight of the device.

The dynamic Compliant Force Distribution socket interface designs provide for an inherently greater biomechanical lock around the underlying bony structure, providing for a greater one to one connectivity between the user's body and the device—further decreasing perceived weight.

Point Pressures and Force Distribution

One of the main areas causing abrasions within a conventional prosthetic or orthotic socket interface is the trim lines. The trim lines are where there is a rapid transition from high pressure to no pressure. Because the conventional socket interface does not change in shape with the dynamic underlying body, the user's skin often rubs at the trim lines, causing abrasions. Conventionally used padded straps for instance are around 1"-2" wide and are typically pulled tight to provide for stability. The skin under the straps is highly compressed, and the skin just outside of the straps is not. This narrow area of high force to no force creates a shear point. The same issue is found at trim lines of the socket.

The compliant socket designs however eliminate the conventional trim-line transitions, and are replaced with a broad compliant fabric, allowing for a significantly broader distribution of pressures, and a very gradual transition from high forces to no forces.

No matter how much "padding" is used with conventional straps or trimlines, the forces remain distributed within a small surface area. Compliant Force Distribution provides a more gradual transition of forces at the edges, and equalizes the amount of force per square inch within the load bearing areas.

Sensor Integration

The Compliant Force Distribution socket interface technology has been successfully applied to high-level upper extremity amputees. In conventional upper extremity socket designs, the electrodes tend to gap away from the body, as they would typically be integrated into a rigid or semi-rigid socket over a dynamic body. Compliant Force Distribution interface techniques instead maintain consistent electrode contact, as the sensors are "hammocked" directly to the user's limbs, with no loss of connection.

The future of socket designs for other levels of amputation, as well as for some orthotics users will incorporate various sensors, including myoelectric electrodes. Other than the Compliant Force Distribution Technology, there is not an elegant method of incorporating sensors and wires within a socket interface environment. These designs solve the outstanding issues that prevent the practical use of sensors and electrodes within the socket, as they are akin to a hammock and inherently hold the interface tightly against the users' limb—maintaining consistent contact.

Skin Environment

Conventional interface designs encompass the user's limb, creating a hot, moist environment that leads to a variety of skin issues including pressure sores, heat rash, abrasions, chaffing, dryness, folliculitis, dermatitis, ulcers, eczema, psoriasis, dryness, and skin breakdown.

The human skin is designed to breath. By design, the human skin perspires to cool itself, but instead, any perspiration within a conventional socket is trapped and a prosthetics user for instance typically can pour sweat out of their socket upon taking it off.

The Compliant Force Distribution interface designs, however, may be breathable, and allow for perspiration to escape, and the limb to remain cool, naturally.

Control and Stability

In transfemoral amputations for instance, the cut femur bone is no longer directly connected to the remaining leg. With a conventional hydrostatic socket design, the cut femur bone moves back and forth within the soft tissue of the residual limb, decreasing ambulation efficiency.

Randy Alley recently created the Hi-Fidelity socket to better lock the residual bone in a consistent position within the socket (U.S. Pat. No. 8,323,353). His work with the Hi-Fi demonstrates the ability to alter the biomechanical synchronization between the residual bone and prosthesis by changing how the socket interface is fit to the user.

Likewise, the Compliant Force Distribution design is able to replicate the lost biomechanical and neuromuscular connection between the limb and the user by better controlling underlying bone position within the socket, though through a radically different method. Just as importantly, it does so in a modular, breathable way that also accommodates for volume changes. Unlike Randy Alley's socket design, this approach captures the underlying bony structure in a much less aggressive and more compliant manner, making it easier to achieve more comfort. Instead of using aggressive compression zones that encircle the limb, this design more elegantly captures the contouring of the underlying anatomy to lock the bony structure in a desired orientation with respect to the prosthesis.

By more elegantly spreading the load over a broad surface area, our technology is not only reducing the amount of force per square inch, but more importantly, is providing a much more secure connectivity between the user and the device. A prosthetic or orthotic device is a mechanical or electro-mechanical extension from the body. Every amputee for instance gains what is called external physiological proprioception. This means that they are able to at least partially gain a proprioceptive sense of where the prosthesis is in space, in relation to their body. When they move their leg forward to take a step, they have a sense of where their leg position is in space, even though their prosthesis is not neurally connected to their brain. However, the more "wiggle room" there is between their residual limb skeletal system and the prosthesis, the less specificity they have of a true proprioceptive sense of their leg position.

For transfemoral amputees for instance, the femur bone section is cut at the amputation level and is no longer directly connected to the remaining leg. With a conventional hydrostatic socket design, when the transfemoral amputee kicks their leg forward to initiate the swing phase of gait, their femur bone moves back and forth within the soft tissue of their residual limb, and they lose much of the true proprioceptive sense of leg position.

Volume Accommodating—Dynamic vs. Static

The human body is dynamic-yet the socket interfaces we use today are largely relatively static in their size and shape. Socket interfaces typically use a rigid or semi-rigid carbon fiber shell surrounding a semi-flexible thermoplastic inner layer. While this inner layer has some flexibility, its size and shape remain static, and cannot accommodate weight gain or loss. This leads to discomfort and degradation in functional performance of the user if their body changes in size and shape, and no longer perfectly matches the socket interface. Just a small body weight change of 5 lbs. can significantly affect the socket interface fit. It is like wearing a shoe that is a couple sizes too big or too small—except that the effect is greatly compounded, as the limbs are not designed to bear the incredible ambulation forces, as the foot is designed to do.

The human body gains and loses volume due to hydration levels, foods we eat (for instance salty foods versus non-salty foods), exercise, or lack thereof, eating habits, age related issues, and other diseases like diabetes and dysvascular disease.

If the socket does not perfectly fit, it leads to abrasions, rubbing, pressure on the cut end of the amputated bones, unwanted pressure on sensitive nerves, and overall discomfort. Most amputees and orthotics users experience socket interface discomfort from time to time. Socket interfaces tend to need to be replaced every 1 to 3 years due to body size and shape changes.

The Compliant Force Distribution technology inherently accommodates for size and shape changes in the user. These socket interface designs are compliant-based, versus a rigid or semi-rigid shape, therefore the socket interface can be quickly and easily user-adjusted in its tightness to provide a comfortable fit independent of weight gain or loss. As has been found with the Shoulder Disarticulation version of the Compliant Force Distribution socket interface design, the amputee is able to quickly and easily adjust the fit of their prosthetic device to ensure the most comfortable fit.

Conventional prosthetic socket designs could be more closely compared to wooden clog shoes, in that their size and shape do not adequately accommodate for the dynamic nature of the human body. Even if the wooden clog were to be perfectly contoured to the user's foot, its comfort would be limited, especially when the size and shape of the dynamic foot were to change. A compliant-based socket design would more closely resemble the VIBRAM five-fingered shoes, in that they are made of a soft dynamic material that perfectly contours to the user's foot, versus the foot matching to the shoe.

Fitting Method

Conventional socket fitting methods typically require capturing an impression of the limb shape, modifying that impression shape, and iterating through test sockets before a final fitting shape is defined and completed. Capturing the impression shape is largely accomplished by hand casting, or scanning. The cast is then either by hand or electronically modified in shape to achieve a positive model of the socket shape, to then pull a thermoplastic inner socket over be used in diagnostic evaluation of the fitting on the actual limb. This process is time consuming, inexact, and inefficient.

3. Description of the Known Prior Art

Conventionally used prosthetic interfaces remain as an anatomically contoured socket in which the residual limb fits within. This socket may be specifically tailored to the residual limb's size and shape, but it largely remains as a static size and shape. While some flexible materials may be incorporated, their flexibility is typically no more than minor amounts of give at their edges, and not true accommodation for the dynamic nature of the underlying body in which they are fit.

In recent years there have been a few attempts at improving lower extremity socket interface design, and overcome some of the outstanding issues surrounding them.

One such attempt developed by Randy Alley through the Hi-Fidelity (Hi-Fi) Interface (U.S. Pat. No. 8,323,353) design offers excellent locking around the underlying skeletal system, versus solely hydrostatic tissue loading as with conventional designs. However, the Hi-Fi system currently requires full customization for each user, and currently does not accommodate volume changes of the user any more so than other conventional transfemoral designs. It also uses an enclosed socket cavity in which the limb is fit, which does not fully address the environmental issues of limb encapsulation. While this design could in theory be transitioned to more of a modular approach, its design by nature would still require significant customization of the various components to fit appropriately to the user.

The Alley design requires a common distal connection point for each of the four vertical struts. The common distal connection point holds the vertical struts in a certain orientation about the limb for a transfemoral amputee, resulting in a locked-in socket shape. While the distal common connection point could become modular, once fit to the user, the position of the vertical struts is maintained in a consistent position, and is not quickly or easily adjustable for the patient.

It is important to offer a prosthetic interface design that is modularly adjustable by the end user, in real-time, so that they can match the socket to their limb, versus their limb having to match to the socket. In the Alley design, plastic shims may be used to adjust the static socket shape to the user, by placing them in between the static socket shape and the user's limb to take up space. In this invention, however, our design can be modularly adjusted on the fly, allowing an end user to quickly and easily tighten or loosen to socket fit to match their desired comfort.

The Alley design uses struts that extend from the common distal connection point to the proximal brim of the socket. Our design instead uses floating force distribution anchors, to capture the long bone and conform it to the medial wall of the interface design. By using a floating design, the socket interface fully matches to the shape and size of the underlying limb with real-time adjustability, versus requiring a limb to match the shape of a customized socket fit to the patient, as in the Alley design.

Additionally, the Alley design uses the vertical struts as the structural element of the socket, and does not include any compliant members in the design. In our design, we instead make the force distribution anchors as floating, and not connected as a vertical structural element of the socket, in order to be compliant to match the compliant body, and then can integrated flexible fabric or flexible materials or adjustable connectors to span as the connectors. By doing such, this design can effectively leverage the long bone of the limb to become a structural element of the socket, versus solely relying on the carbon fiber struts to be the structural part of the design. Since this design captures the long bone with floating force distribution anchors, and manages the bone position to the stabilizing anchor, the long bone is controlled and its lock within the system assists in creating a structural element of system support.

The Alley design locks the long bone in a set position from all sides, as the vertical struts compress into the soft tissue circumferentially around the limb. This design instead pulls the long bone over to the stabilizing anchor, generating a more appropriate and controlled femoral angle.

According to the Alley patent, their design uses a limb encapsulated strut design where the struts are "appropriately contoured to a patient's residual limb" and "contains windows through which soft tissue can flow". Our design instead is able to use force distribution anchors that can either be of an off-the-shelf shape, or can be dynamic in nature, not fully maintaining any particular shape, but rather match to the shape of the limb. In addition, our design does not have windows which the soft tissue can flow, but rather has un-encapsulated areas where there is not structure, and hence no windows.

Still further, Alley's design requires areas of specific isolated compression zones, whereas our disclosure provides broader areas of tissue stabilization, spreading the forces across more surface area than just isolated struts, and instead may utilize a combination of struts and compliant materials together to broaden the load bearing areas. In Alley's design, tissue is compressed such that the bone is locked in a position from all sides, due to the isolated tissue compression. Our design rather uses purposeful contouring around the bone such that a broader area of the limb is captured and controlled, and pulled toward the main anchor stabilizer along the medial aspect of the interface. Alley's design further calls for areas of the interface to be "enclosed or completely open provided there is minimal restriction to soft tissue flow". Our design instead benefits from open areas where the soft tissue may be further controlled with compliant means, versus just relying on it to flow freely with minimal restriction.

Even further, Alley's patent calls for no less than 3 compression portions, while our approach utilizes just 2 pseudo-compression portions, where compliant means may be spanned in between. Our main anchor stabilizer may be sufficient in dimensions to not necessarily cause its own tissue compression in the same manner as other narrower struts would, as in Alley's design.

Still further, Alley's patent also calls for the struts to be of similar length as the long bone. In our design, the length may be modularly adjustable, and does not necessarily need to extend to the furthest distal end, or furthest proximal end, as our force distribution stabilizers are not directly connected to a common distal mounting point or proximal brim as in Alley's designs.

More recently Hurley's (LIM Innovations) (patent application number 2014/0135946 A1) introduced a modular version of Alley's Hi-Fi socket. Hurley's design accomplishes much the same as what was described by Alley, and functionally is equivalent how it fits to a residual limb, with the exception of being modular. Similar to Alley's design, the Hurley design requires significant customization, and a complex and time consuming fabrication and assembly process, and encapsulates the limb in a structure that surrounds the limb as a solid structural unit. While Hurley's design is modular in nature, the modularity of the design is suited well for a practitioner to modify it to a patient, but is not conducive for a patient to modify it on the fly in real-time. Hurley's design as well locks the long bone in a set position from all sides, as the vertical struts compress into the soft tissue circumferentially around the limb. The Hurley design shares most of the same disadvantages as Alley's design, as was discussed above, as they effectively have the same functions in how they fit about the underlying limb.

The recent REVOLIMB design uses an adjustable Boa lacing system to slightly tighten or loosen various pads within the socket. This provides a step toward making a more accommodating socket though it still remains as a fully encapsulated limb environment, is complex to fabricate, requires significant customization, and is limited in its volume accommodation.

Cornell (U.S. Pat. No. 8,945,237) disclosed a transfemoral socket using a fabric spanned across one side of the frame, referred to as a sail. His disclosure spans the limb circumferentially, but fails to capture or manage the long bone. In his sail design, the limb is simply encapsulated with a combination of rigid frame, and flexible fabric, though the entire limb is encapsulated circumferentially giving a similar socket shape and effects as conventional socket designs. The main advantage that his sail material is that it provides more flexibility in sitting, and is adjustable. However, by not controlling the bone position within the socket, it fails to influence the biomechanical efficiencies while walking.

Meanwhile, Cornell's disclosure also calls for the remainder of the limb, which is not supported by the rigid support to be supported by the fabric sail support, to create a hydrostatic weight bearing support of the entire limb and its tissue. Conversely, in our disclosure, we may purposely maintain open areas to allow the tissue to expand out as needed, so that we can compress the medial/lateral dimension, drawing the long bone into proximity with the anchor stabilizer.

The notion of using a rigid J-shaped support, as Cornell discloses, has been used in the prosthetics field for many years. Between 1999 and 2006 various tests were conducted at Sabolich Prosthetics to cut down the frame's trimlines to more a micro-frame design, resembling the Hi-Fi socket in look, though not necessarily fully in function with aggressive compression zones in the same way as Alley has demonstrated. These clinical fitting experiments, as well as the Hi-Fi sockets design, have demonstrated that the force coupling within a transfemoral socket can be achieved through a micro-frame structure, versus a fully encapsulated frame. Various tests were conducted using a J-shaped main frame, with a compliant silicon material encircling the limb that would be connected to the J-shaped frame. We found that the limb was able to remain stable in such a setup. Distal cups trimmed out at the distal end of the socket, and J shaped trimlines have been common in various socket shapes for many years (Schuch, Michael, Transfemoral Amputation: Prosthetic Management, Atlas of Limb Prosthetics 20B).

Other prosthetic component manufacturers provide components, such as gel liners, for use in conventional sockets, which do not significantly depart from conventional socket design. The Ossur Seal-In V liner for instance is a flexible thermoplastic/silicon sock that rolls over the amputee's residual limb, which then fits into the conventional socket. The sealing rings of this design offer a better method of suspending the prosthesis than predecessor designs, by forming a suction sealing effect toward the distal end of the socket. While the liner does provide cushion for the user, and the suspension capabilities of this design work very well, it is but an iteration of conventional socket approaches, and fails to truly accommodate for volume changes in the residual limb.

Additionally, unlike Alley, Cornell, or Hurley's disclosure, our design does not require a proximal brim as is commonly used. Unlike any other interface design, we can effectively have a brimless socket interface since this design is the only one which does not truly encapsulate the limb with a structure about the circumference of the entire limb. Instead, this disclosure may have floating elements, which may be modularly and adjustably tightened against the limb.

Still further, the other socket designs including Alley, Hurley, and Cornell, all utilize distal contouring of the limb within the socket, and as such bear a portion of the weight distally. Likewise, any weight bearing that is bore circumferentially around the limb extends directly to the distal attachment area. This invention, however, may utilize a non-weight-bearing distal end, and any force through the body of the limb may be bore through the stabilizing unit alone to the distal attachment area. By doing such, the size of the interface can be modularly adjusted circumferentially in real-time by the end user.

Any contouring of the interface about the distal end of the limb may come through compliant materials, versus rigid structure, as used by Alley, Hurley, and Cornell. The distal end of this invention may use more of a hammock-type fit with the contouring of the distal end to be modularly adjusted to the user, through compliant materials that match to the user, versus the user having to match to a pre-formed shape on the distal end of a conventional socket. Spanning fabric to create a distal end, if one is used, ensures comfort, and that there is not too much force applied in that area.

An open distal end, or a modularly adjustable distal end through compliant materials allows for open wounds on the distal end of the limb to be un-enclosed, and to promote healing. As such, this invention could be applied to a new amputee, quickly after the amputation, or to a user who needs to have their distal end de-weighted for healing purposes. An open air design makes for the skin environment to be significantly healthier, versus the conventional hostile interface environment of conventional sockets that encapsulate the limb in a hot, moist environment.

Even if weight is applied to the distal end of this invention, it is estimated that a relatively small amount may be in contact there, with a predominant amount, likely above 90% to be applied through the stabilizing unit, and its opposing force coupling means.

Likewise, this invention could be applied in developing nations, where there is a need for a modular prosthetic design that would not require time consuming an expensive custom fabrication processes, materials, and equipment. Through using off-the-shelf modular kit components, prosthetics can now be fit, either locally or in developing nations, inexpensively. And, since this invention offers so much modularity to fit various users, and fit with them with increased comfort and control, the end user's life is enhanced. Each of the elements of this disclosure can be offered in a kit set, including the connectors, stabilizing unit, and force distribution anchors, etc., to allow for quick and accurate fitting of prosthetics.

In each of the above prior art, conventional casting, modification, and iterative fitting evaluations are required.

SUMMARY OF THE INVENTION

The present invention relates generally to a new and improved prosthetic interface design, and method of producing. In particular, the present invention is a new and improved method of providing control and comfort within a prosthetic device in a more efficient and effective manner.

In this respect, before explaining at least one embodiment of the invention in detail, it is to be understood that the invention is not limited in this application to the details of construction and to the arrangement of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

Accordingly, titles, headings, chapters name, classifications, and overall segmentation of the application in general should not be construed as limiting. Such are provided for overall readability and not necessarily as literally defining text or material associated therewith.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved method of fitting prosthetics to those with limb loss.

It is a further object of the present invention to provide a prosthetic interface that is simpler and more consistent to fit to the user.

It is a further object of the present invention to provide a prosthetic interface whose fit is measurable, quantifiable, and repeatable.

It is a further object of the present invention to provide a prosthetic interface that is user adjustable.

It is a further object of the present invention to provide a prosthetic interface that is more breathable.

It is a further object of the present invention to provide a prosthetic interface that is lower profile under clothing.

It is a further object of the present invention to provide a prosthetic interface that is lighter in weight.

It is a further object of the present invention to provide a prosthetic interface that is modular and repairable.

It is a further object of the present invention to provide a prosthetic interface that can be fabricated less expensively and quicker.

It is a further object of the present invention to provide a prosthetic interface that uses compliant structures versus rigid or semi-rigid structures.

It is a further object of the present invention to provide a prosthetic interface that truly accommodates for volume and shape changes of the dynamic underlying body.

It is a further object of the present invention to provide a prosthetic interface that provides gradual transitions of forces at its trim lines.

It is a further object of the present invention to provide a prosthetic interface that does not encapsulate the limb in the same manner as conventional designs.

It is a further object of the present invention to provide a prosthetic interface that captures the lost biomechanical and neuromuscular connection between the limb and the user.

It is a further object of the present invention to provide a prosthetic interface to better control underlying bone position within the socket.

Another object of the present invention is to provide a new and improved system which provides some of the advantages of the prior art, while simultaneously overcoming some of the disadvantages normally associated therewith.

These together with other objects of the invention, along with the various features of novelty that characterize the invention, are pointed out with particularity in the claims annexed to and forming a part of this disclosure. For a better understanding of the invention, its operating advantages, and the specific objects attained by its uses, reference would be had to the accompanying drawings and descriptive matter in which there are illustrated preferred embodiments of the invention.

BRIEF DESCRIPTION OF THE PICTORIAL ILLUSTRATIONS, GRAPHS, DRAWINGS, AND APPENDICES

The invention will be better understood and objects other than those set forth above will become apparent when consideration is given to the following detailed description thereof. Such description makes reference to the annexed pictorial illustrations, graphs, drawings, and appendices.

FIG. 1A generally illustrates an embodiment of a transfemoral socket interface, viewed from a perspective angle.

FIG. 1B generally illustrates an embodiment of a transfemoral socket interface, viewed from a perspective angle.

FIG. 1C generally illustrates an embodiment of a transfemoral socket interface, viewed from a perspective angle.

FIG. 1D generally illustrates an embodiment of an attachment means connected to an embodiment of a force distribution stabilizer, viewed from a perspective angle.

FIG. 1E generally illustrates an embodiment of a transfemoral socket interface, viewed from a perspective angle, using compliant force distribution stabilizer structure with other compliant material spanned there between.

FIG. 1F generally illustrates an embodiment of a transfemoral socket interface, viewed from a perspective angle, using a less compliant force distribution stabilizer structure with other compliant material spanned there between.

FIG. 1G generally illustrates an embodiment of a transfemoral socket interface, viewed from a perspective angle, using a form holding structure spanned between force distribution stabilizers.

FIG. 1H generally illustrates an embodiment of a transfemoral socket interface, viewed from a perspective angle.

FIG. 1I generally represents possible cross sections of a proximal top-down view of an embodiment of the stabilizing unit 102, as may be affixed to the medial or lateral aspect of the transfemoral limb.

FIG. 2A generally illustrates an embodiment of a compliant structure as may be used for the gluteal fold area.

FIG. 2B generally illustrates an embodiment of a compliant structure as may be used for the gluteal fold area.

FIG. 3 generally illustrates another embodiment of a transfemoral socket interface, viewed from a perspective angle.

FIG. 4A generally illustrates another embodiment of a transfemoral socket interface, viewed from a perspective angle.

FIG. 4B generally illustrates another embodiment of a transfemoral socket interface, viewed from a perspective angle.

FIG. 5 illustrates an embodiment of the prior art, using an encapsulated socket interface.

FIG. 6A generally illustrates another embodiment of a transfemoral socket interface, viewed from a perspective angle.

FIG. 6B generally illustrates a close up view of an embodiment for a distal femoral stabilizing unit.

Figure 13:
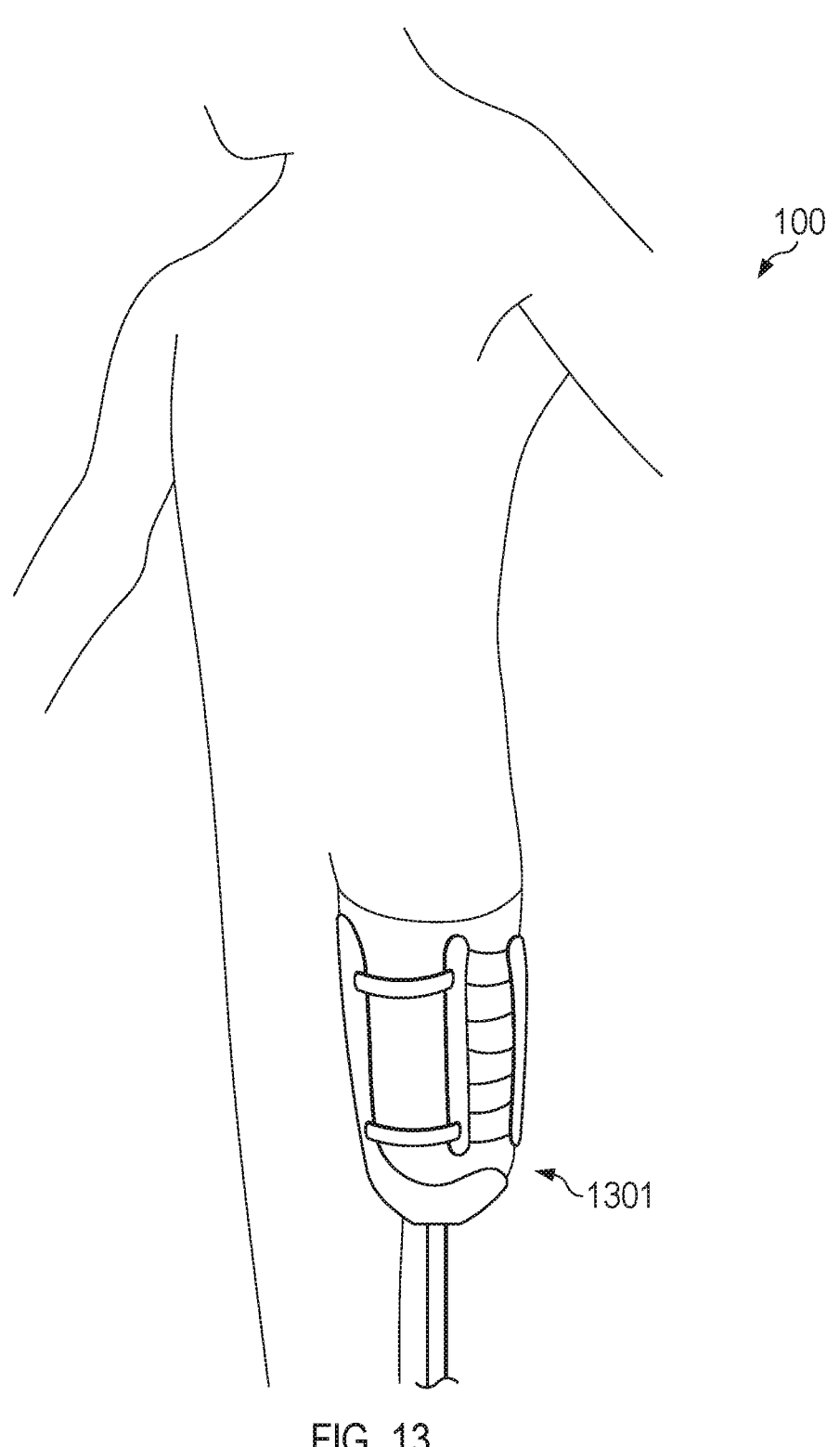

FIG. 13 generally illustrates an embodiment of a transfemoral socket interface, viewed from a perspective angle, being worn by a user.

Figure 14:
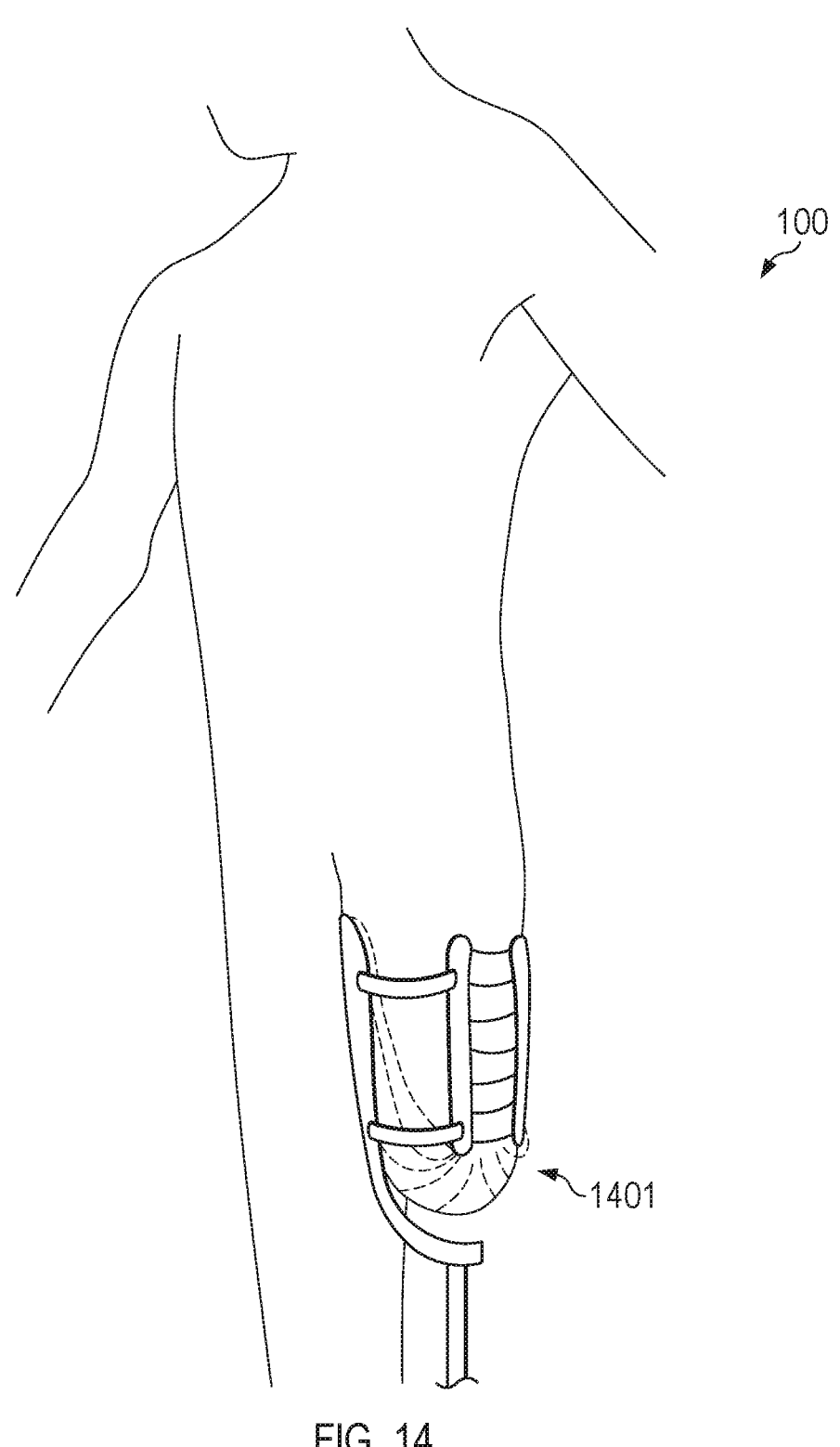

FIG. 14 generally illustrates an embodiment of a transfemoral socket interface, viewed from a perspective angle, being worn by a user.

Figure 15:
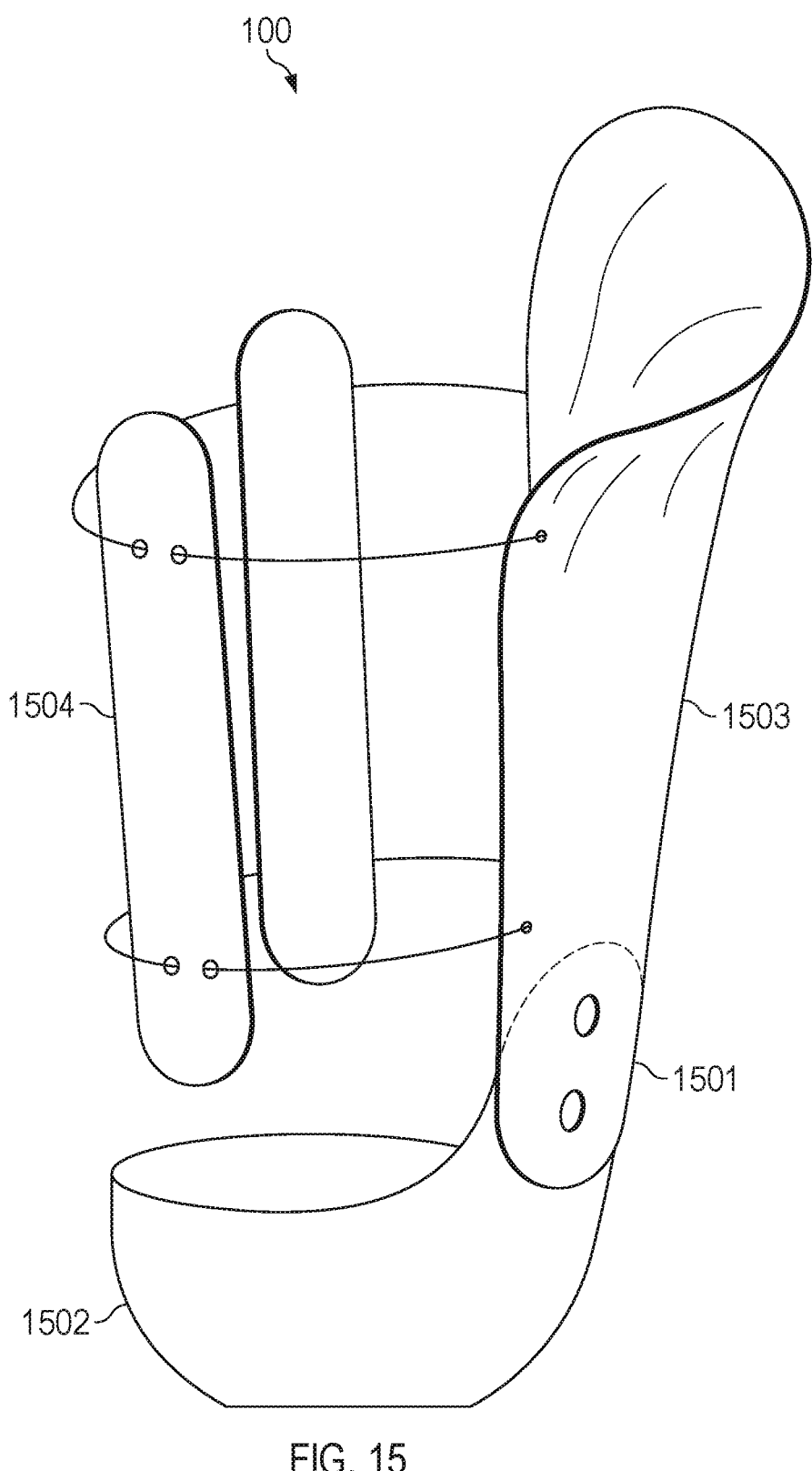

FIG. 15 generally illustrates an embodiment of a transfemoral socket interface, viewed from a perspective angle.

Figure 16:
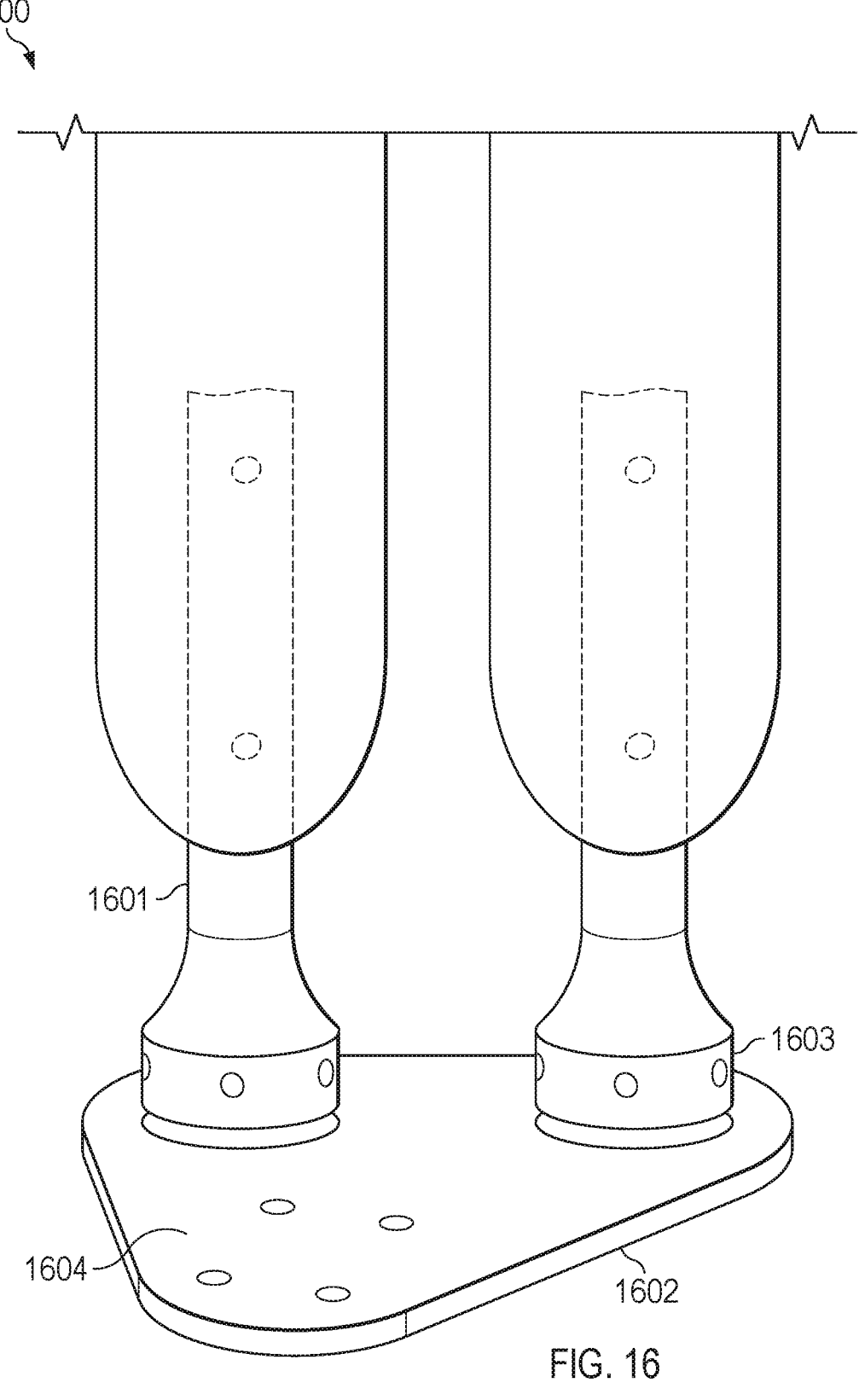

FIG. 16 is a perspective view of a distal attachment embodiment.

Figure 17:
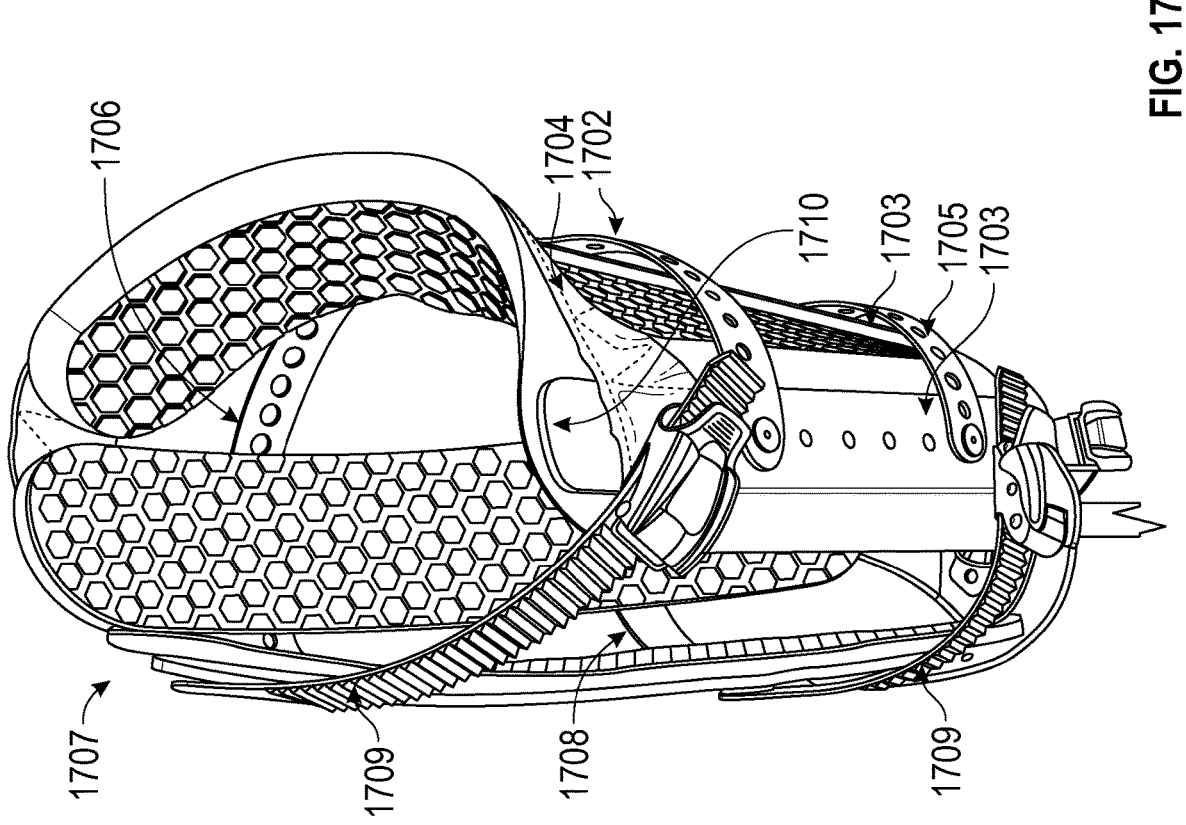

FIG. 17 is a perspective view of an embodiment of a prosthetic interface.

Figure 18:
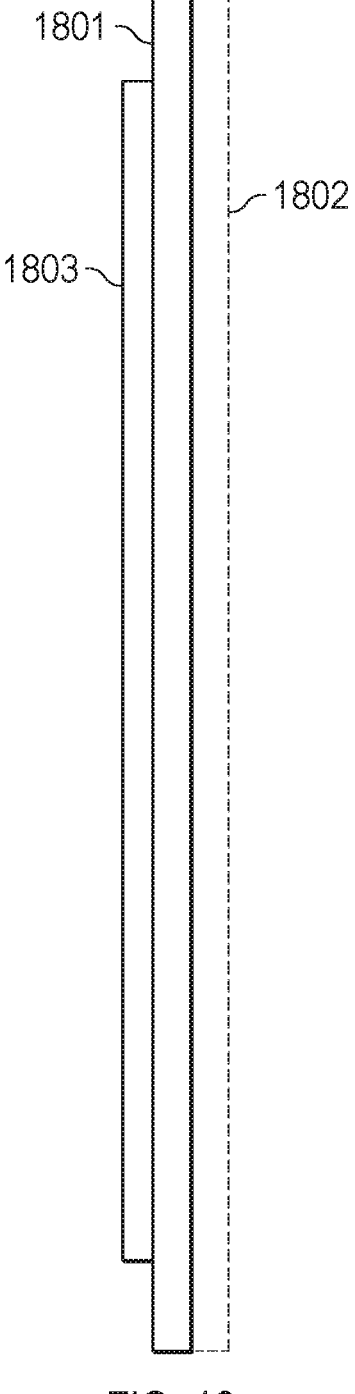

FIG. 18 is a cross section view of an embodiment of a pad.

Figure 19:
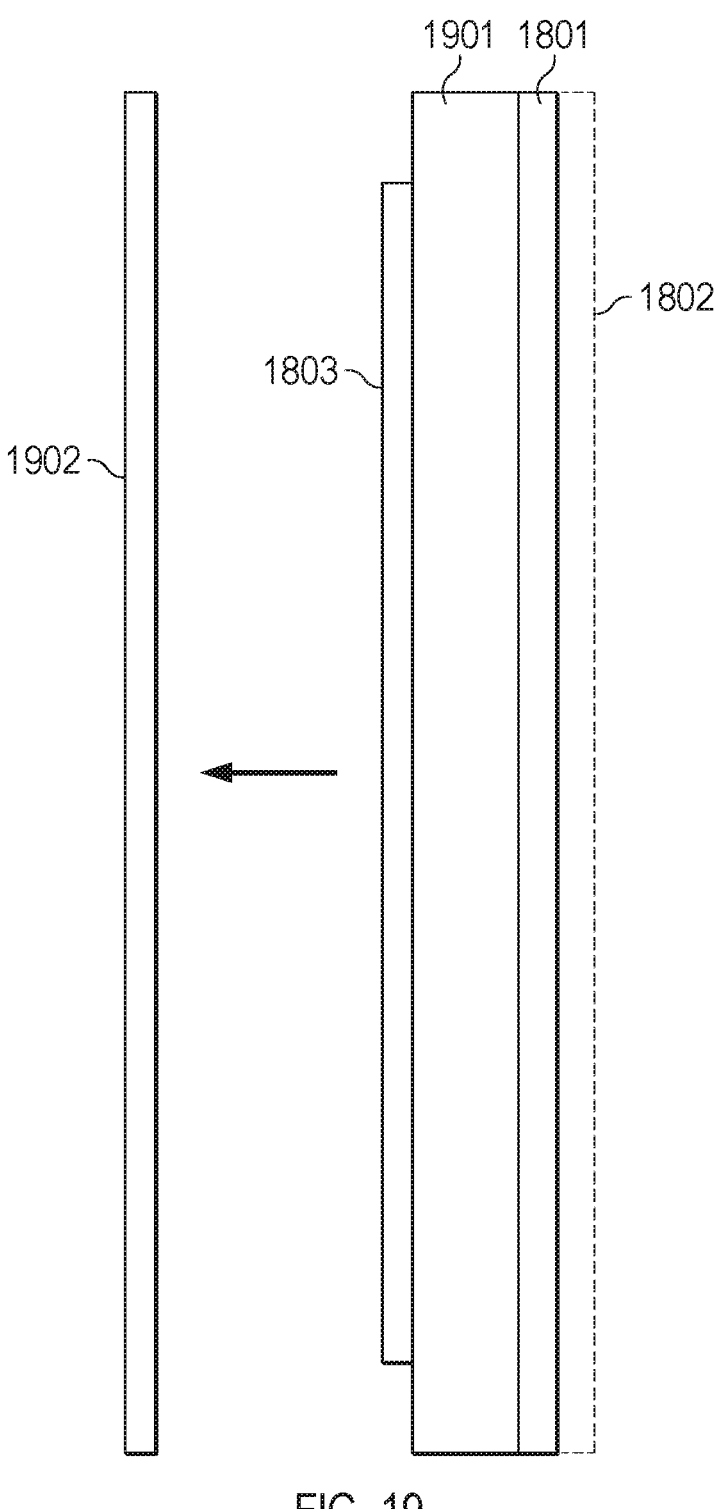

FIG. 19 is a cross section view of an embodiment of a pad.

Figure 20:
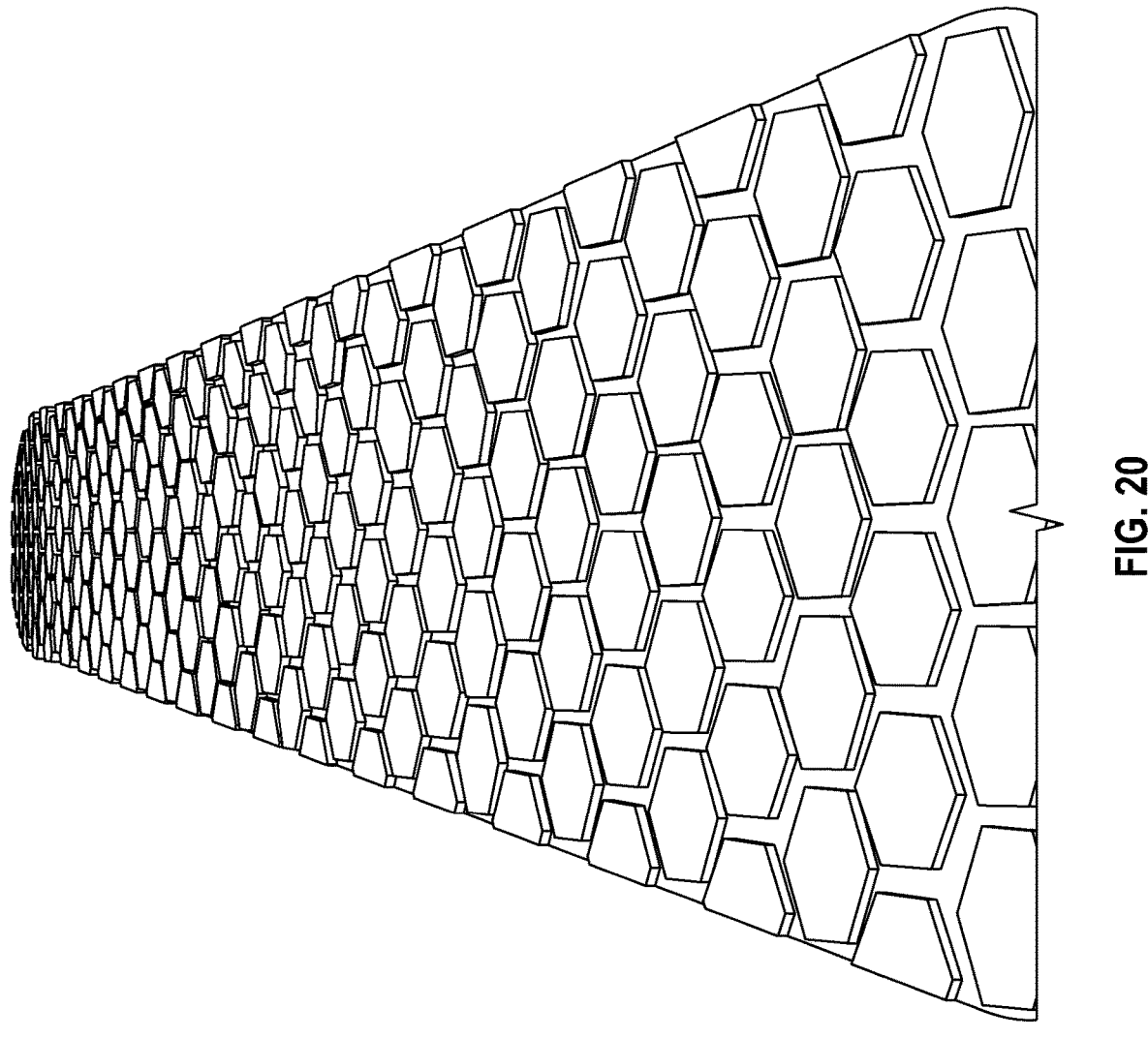

FIG. 20 is an embodiment of a surface texture on a pad.

Figure 21:
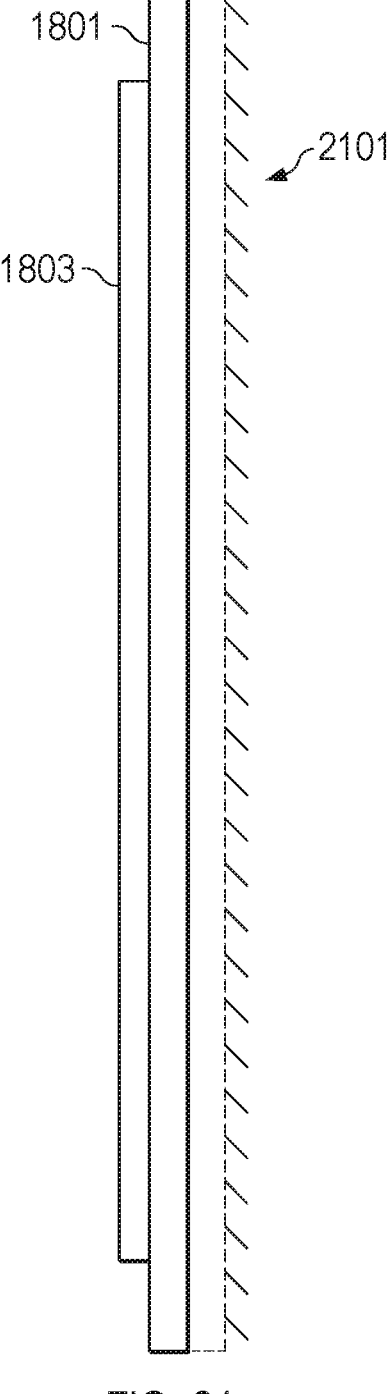

FIG. 21 is an embodiment of a surface texture on a pad, which may be used for suspension or control within a device.

Figure 22:
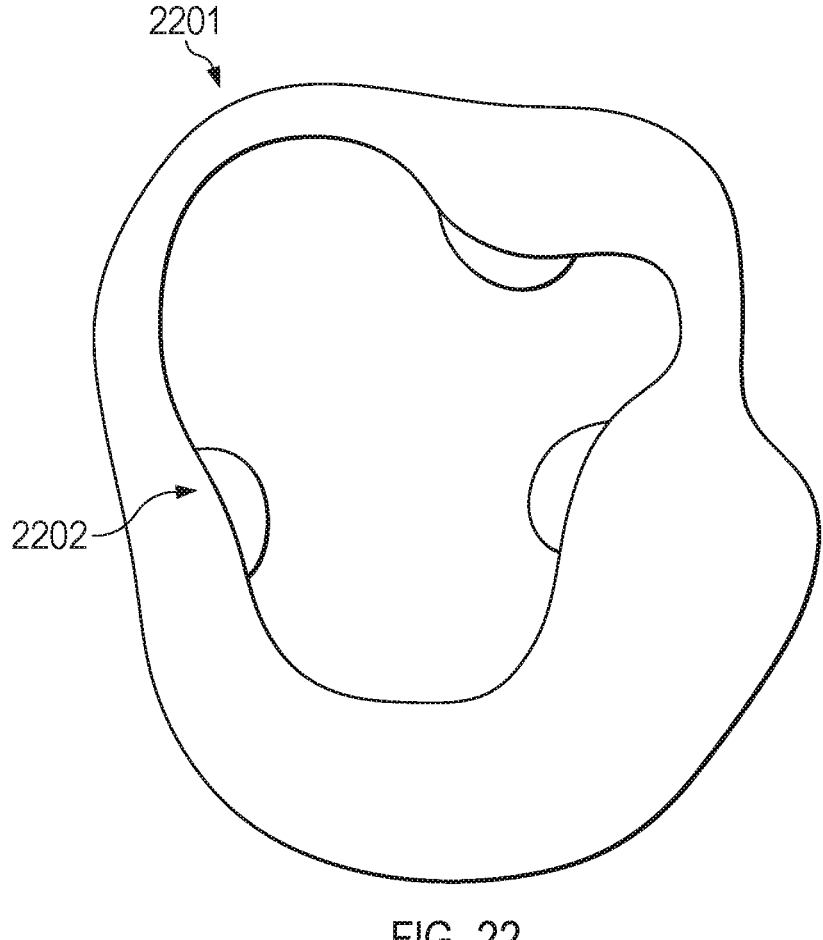

FIG. 22 is an embodiment of an application of using such pads within an existing socket.

Figure 23:
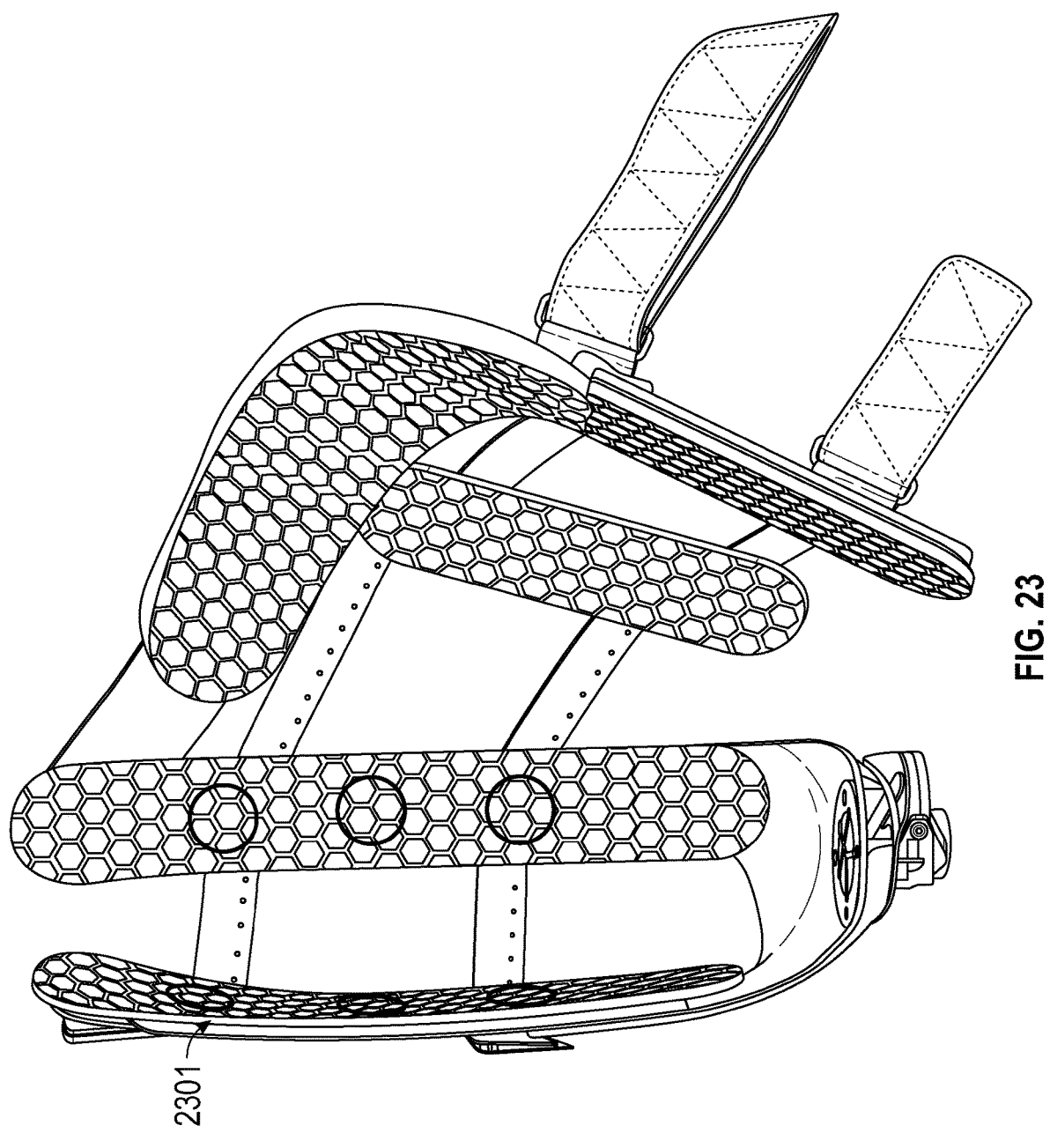

FIG. 23 is a perspective view of an embodiment of the disclosed invention in a splayed open position.

Figure 24:
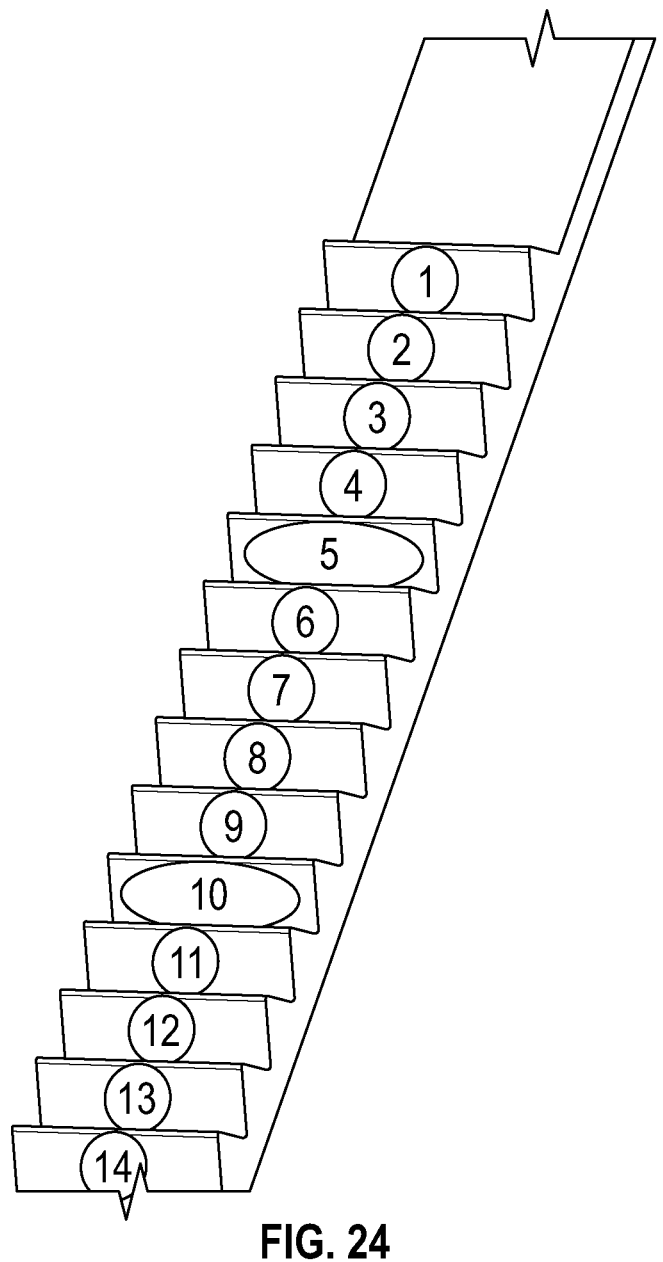

FIG. 24 is an embodiment of a connector with incremental numbers designating its position.

Figure 25:
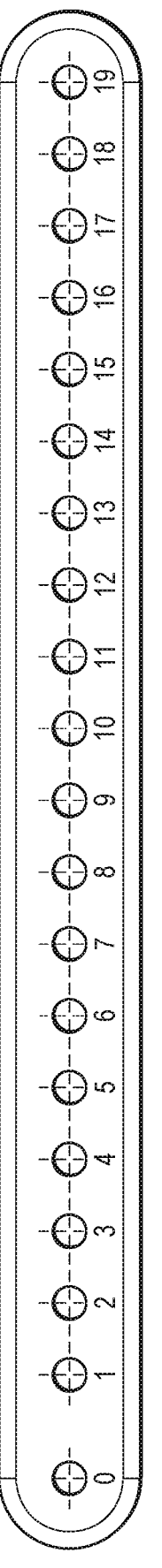

FIG. 25 is an embodiment of a connector with incremental numbers designating its position.

Figure 26A:
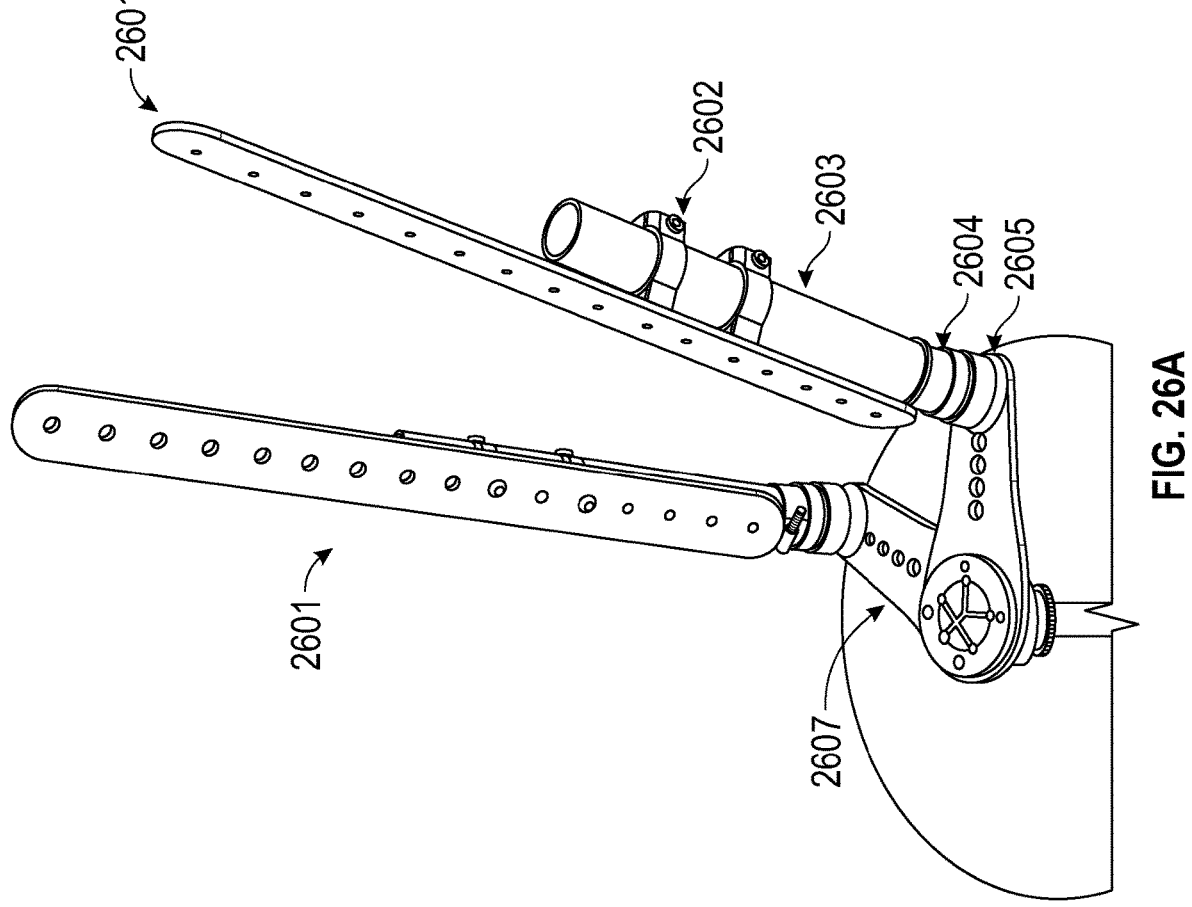

FIG. 26A is an embodiment of a fitting component kit that may be used to fit and align a prosthetic socket and its anchor struts to a user.

Figure 26B:
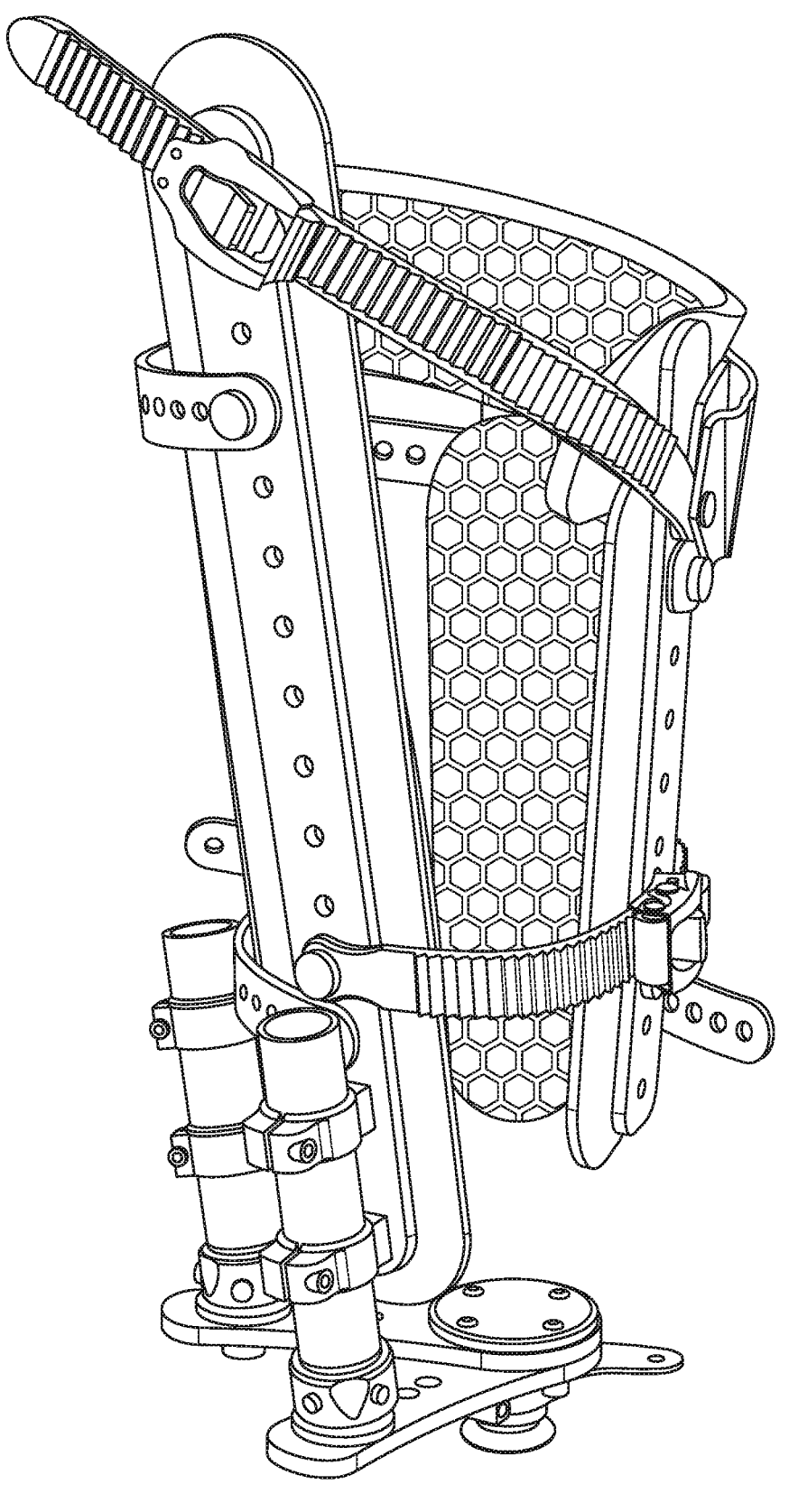

FIG. 26B is an embodiment of a fitting component kit that may be used to fit and align a prosthetic socket and its anchor struts to a user.

Figure 27:
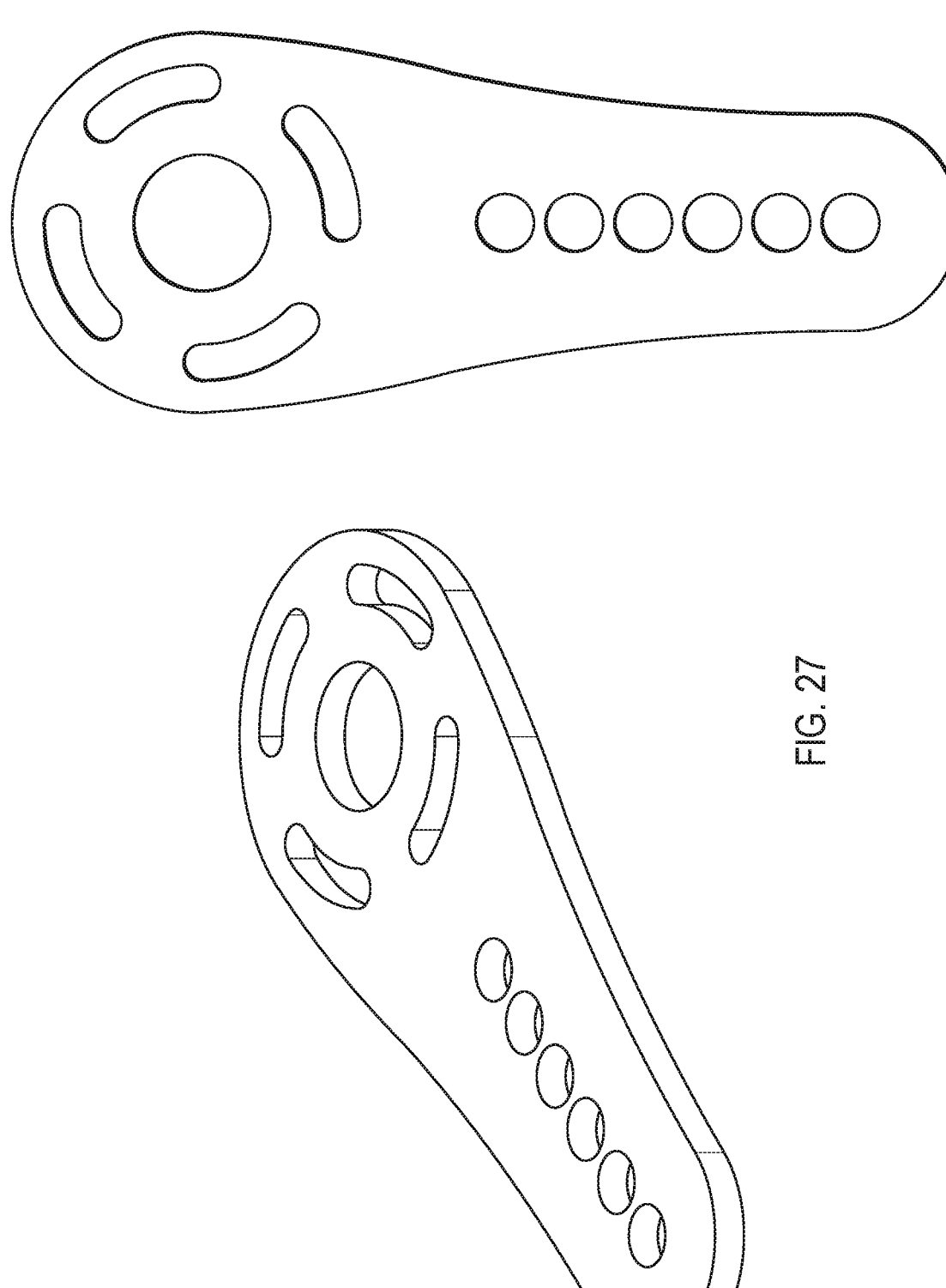

FIG. 27 is an embodiment of a mounting plate with infinite adjustability in rotary position.

Figure 28:
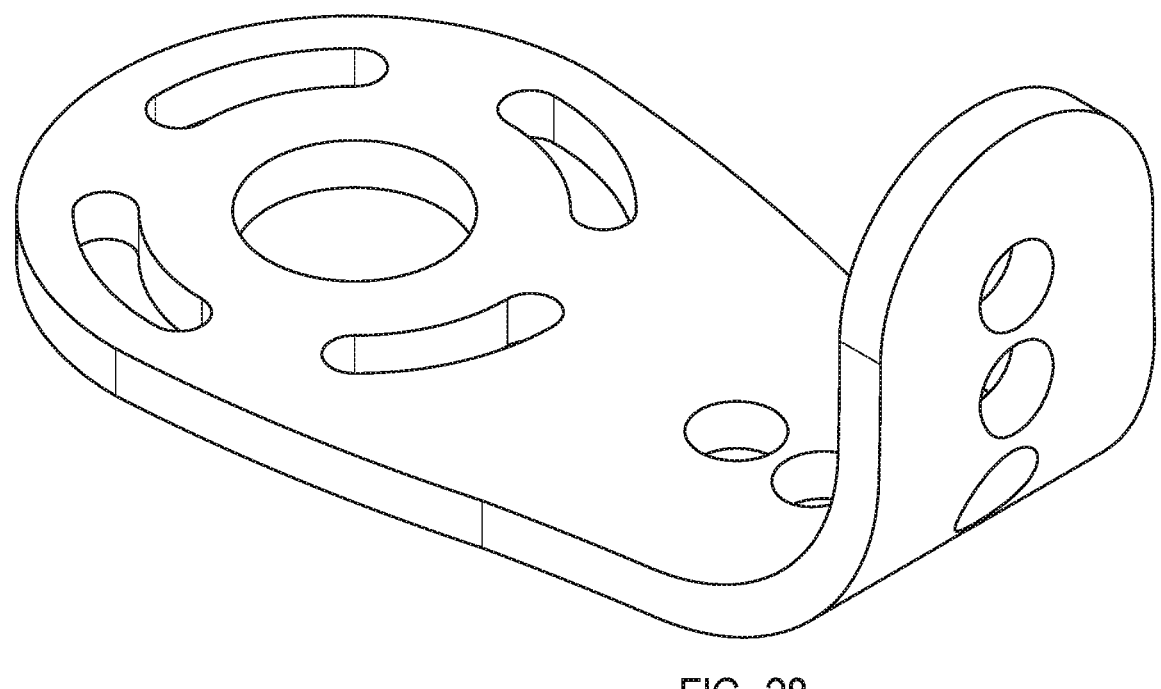

FIG. 28 is an embodiment of a distal mounting plate that may be modified in its angle to connect an anchor strut to a distal end.

Figure 29A:
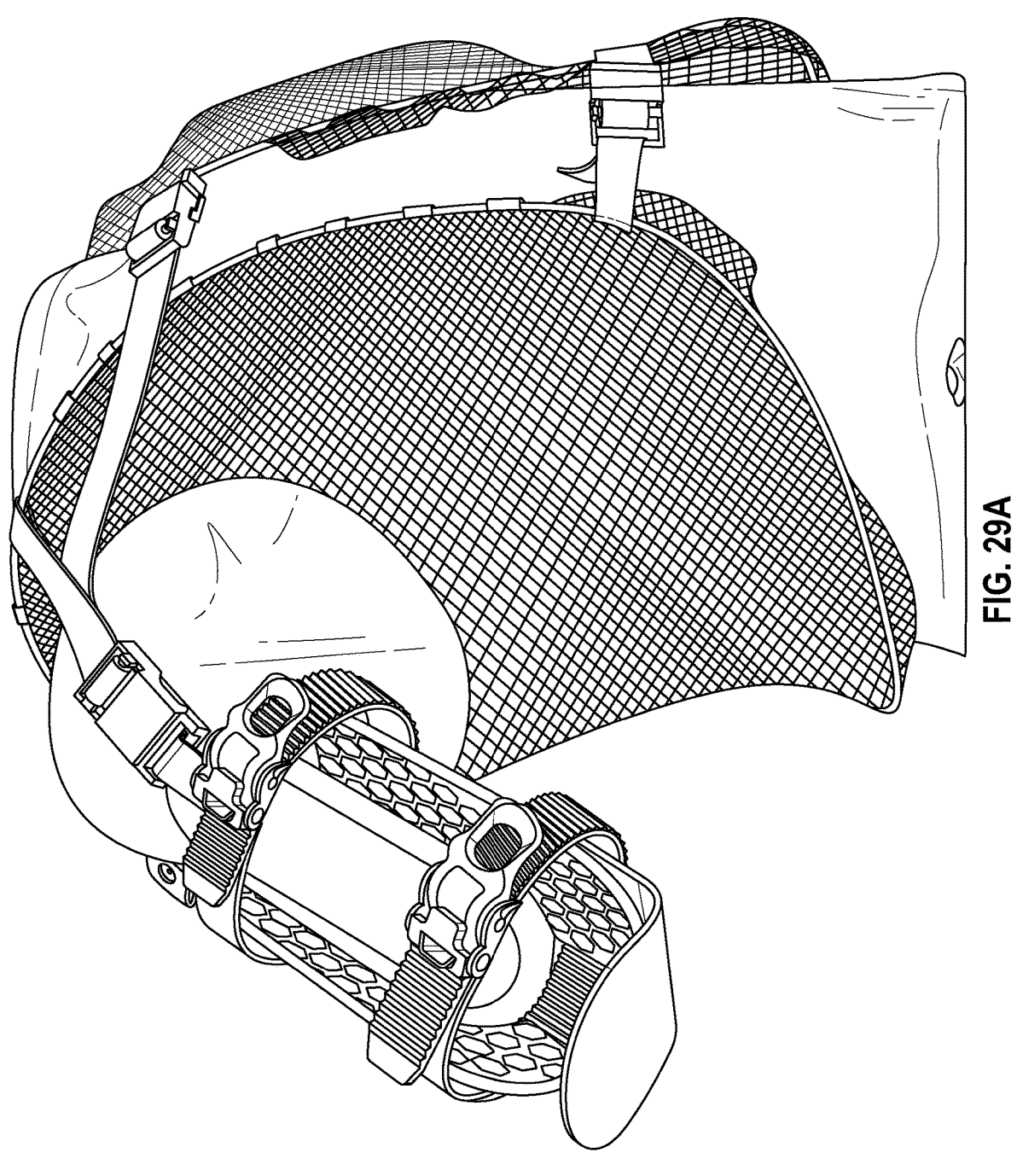

FIG. 29A generally illustrates an embodiment used in a transhumeral application.

Figure 29B:
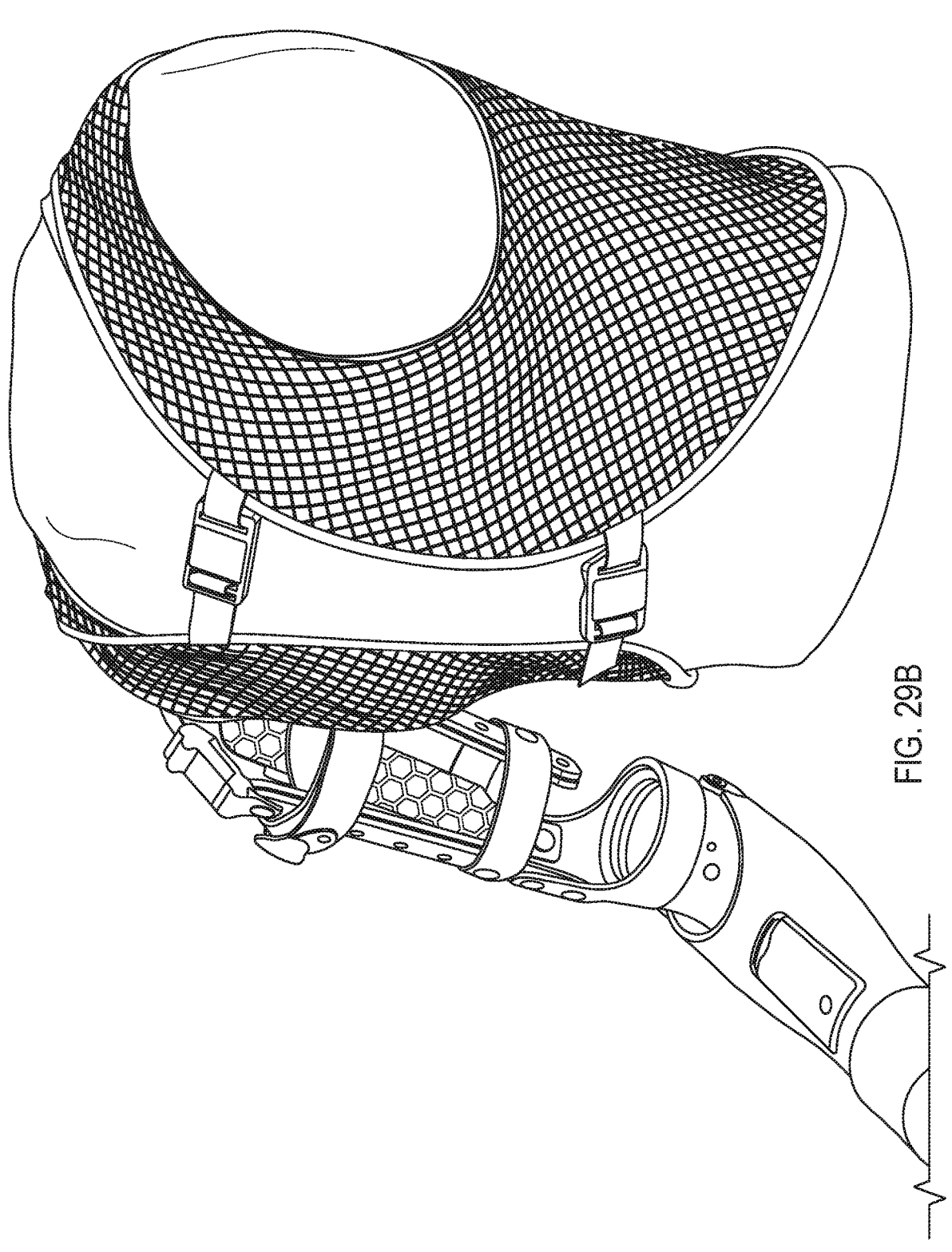

FIG. 29B generally illustrates an embodiment used in a transhumeral application.

Figure 29C:
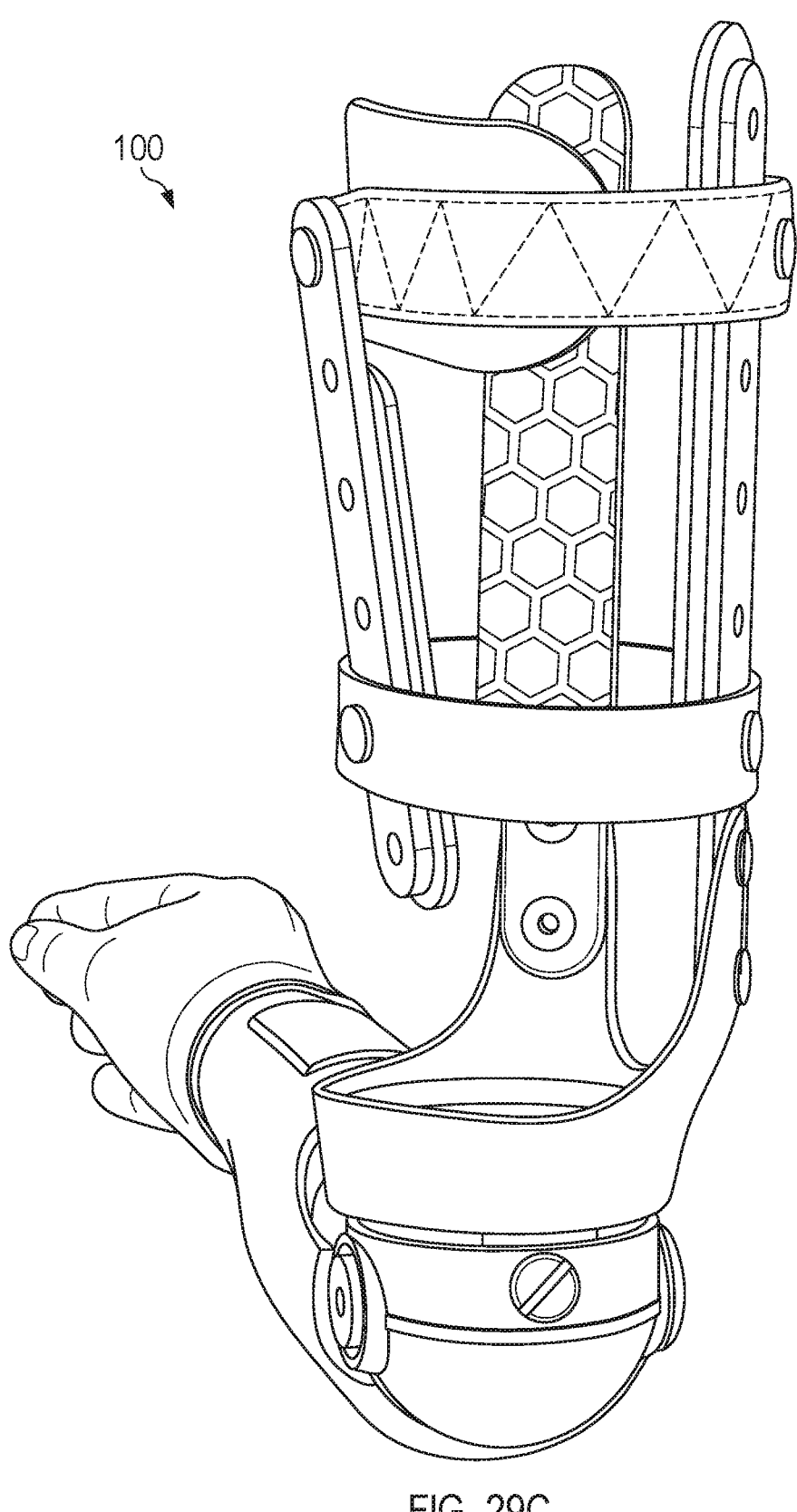

FIG. 29C generally illustrates an embodiment used in a transhumeral application.

Figure 29D:
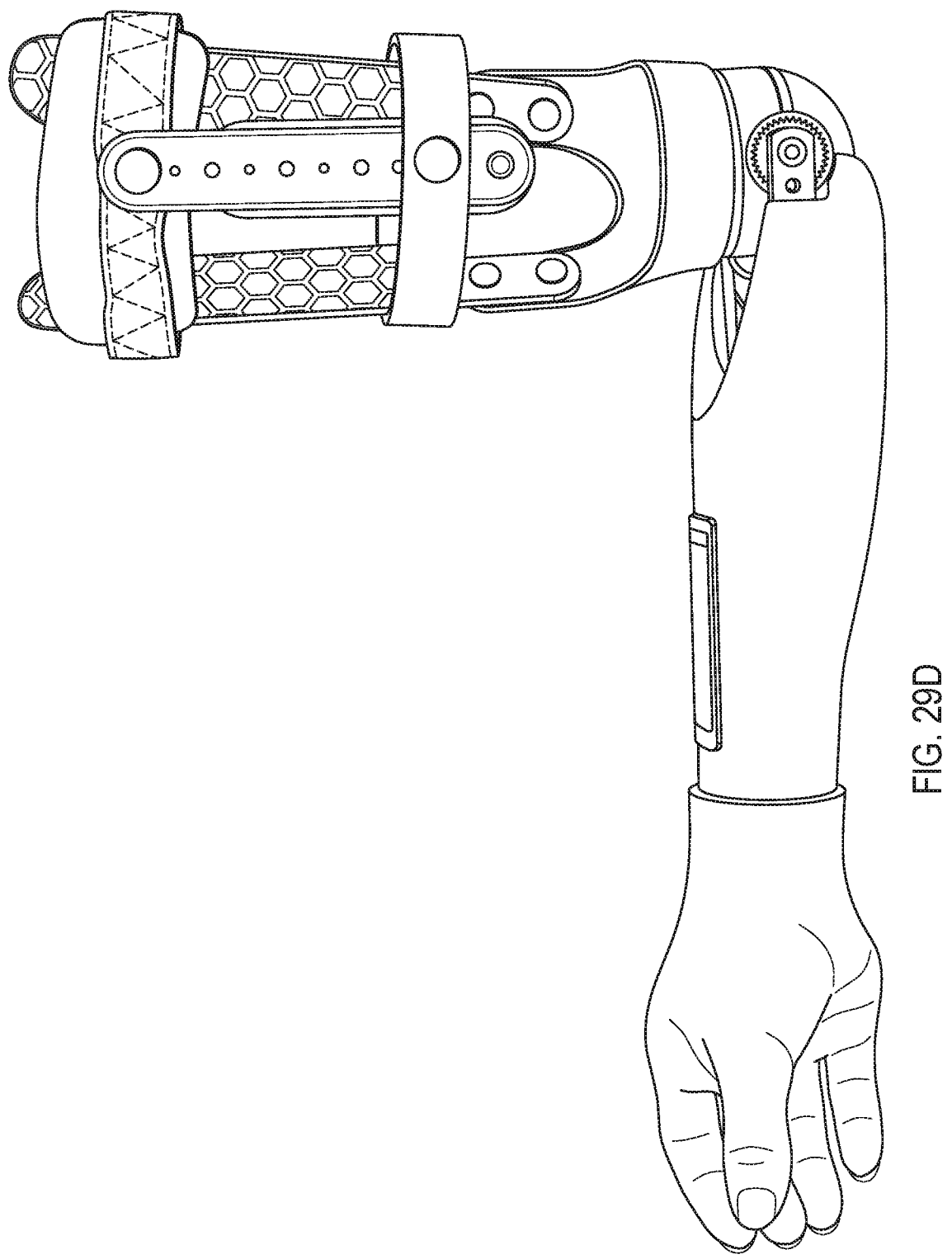

FIG. 29D generally illustrates an embodiment used in a transhumeral application.

Figure 29E:
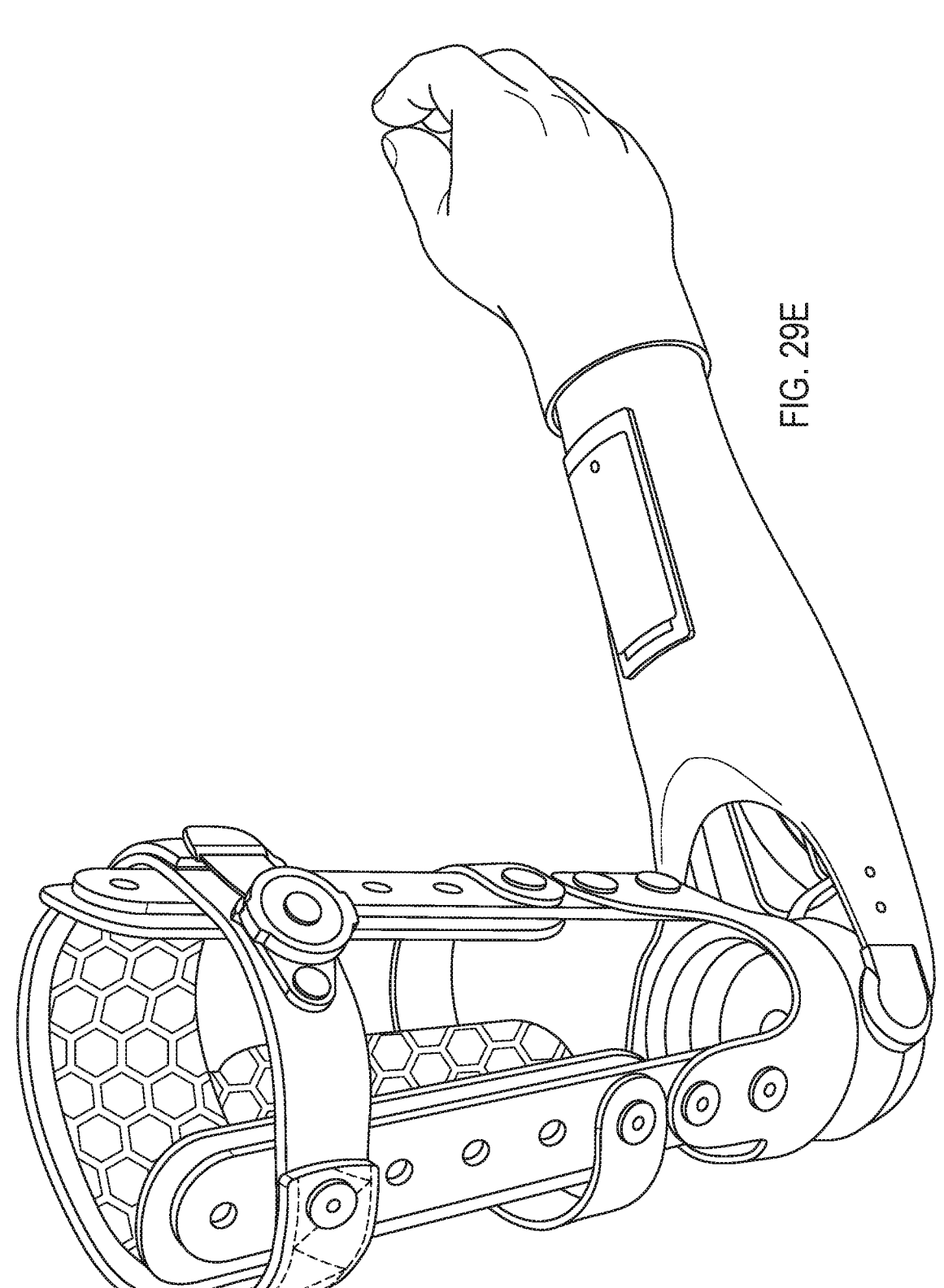

FIG. 29E generally illustrates an embodiment used in a transhumeral application.

Figure 30A:
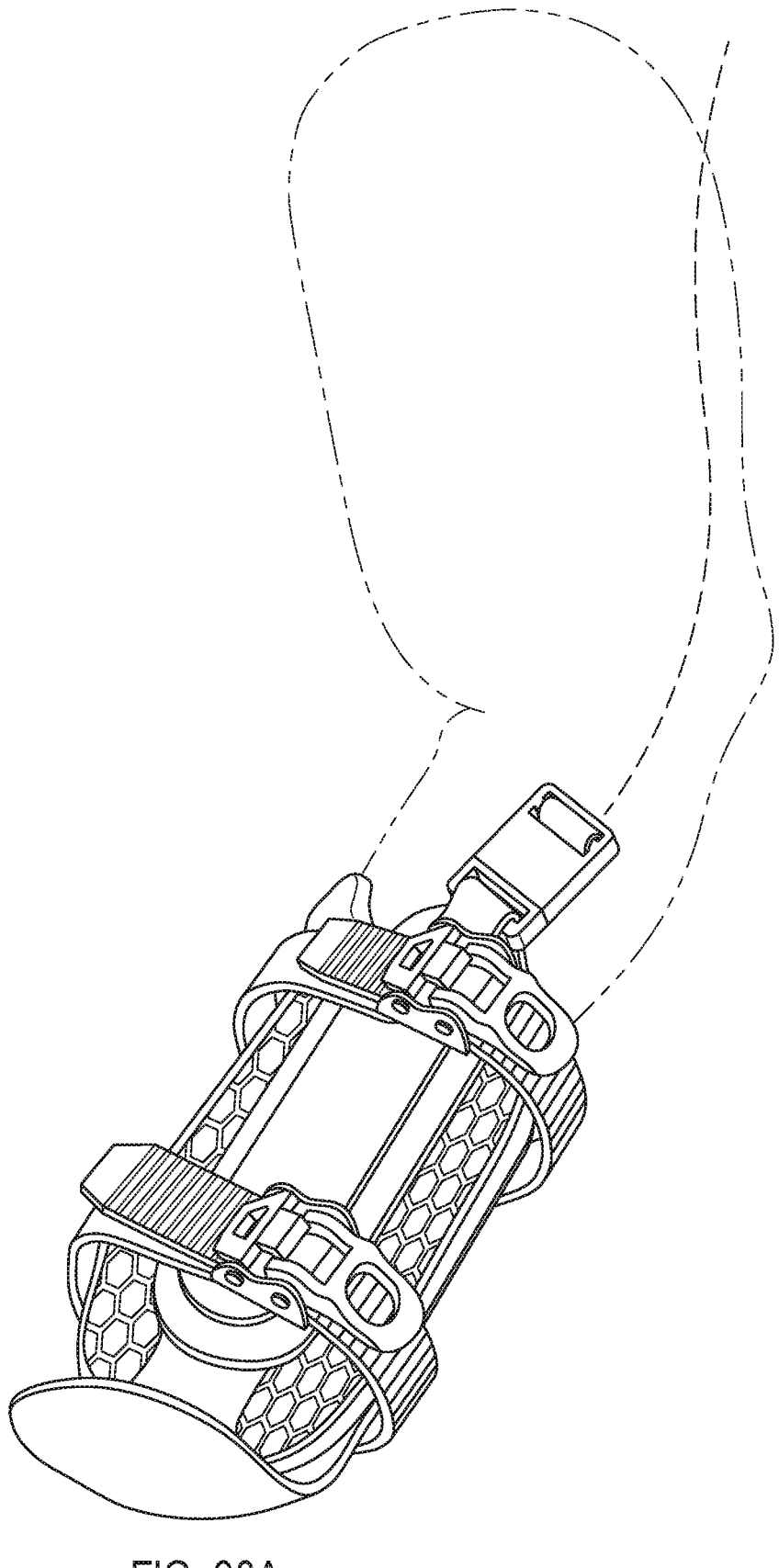

FIG. 30A generally illustrates an embodiment used in a transradial application.

Figure 30B:
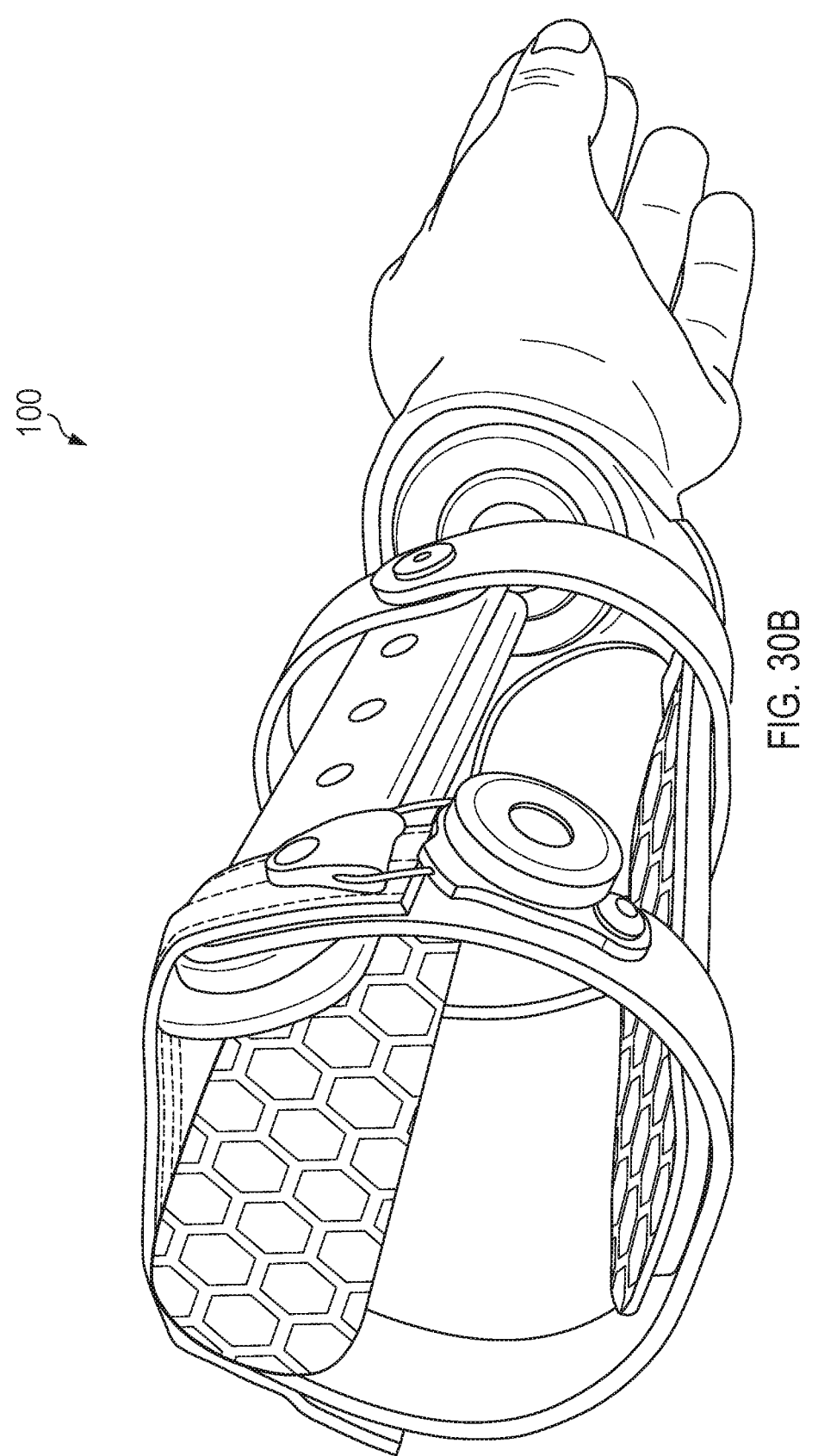

FIG. 30B generally illustrates an embodiment used in a transradial application.

Figure 30C:
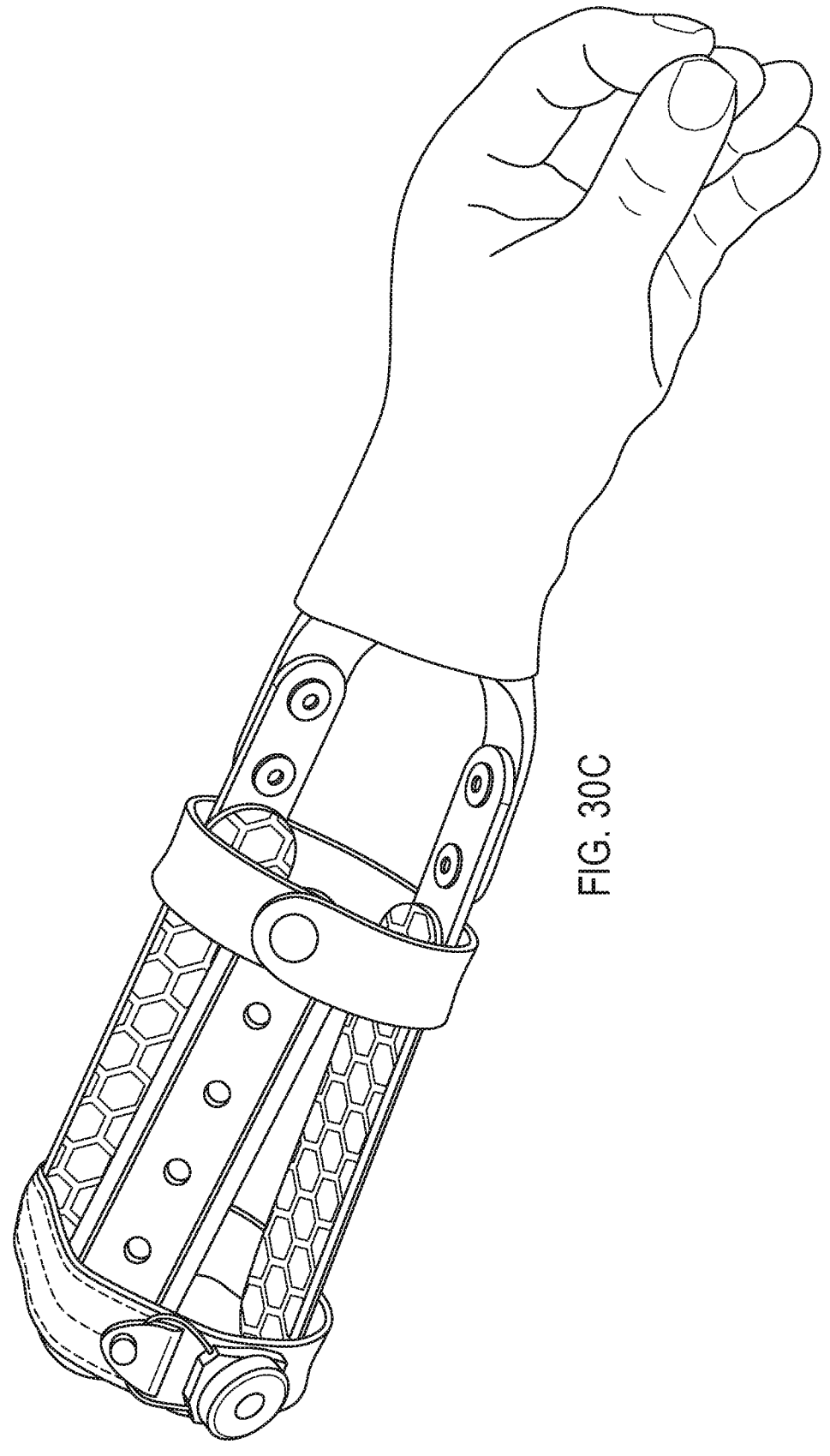

FIG. 30C generally illustrates an embodiment used in a transradial application.

Figure 30D:
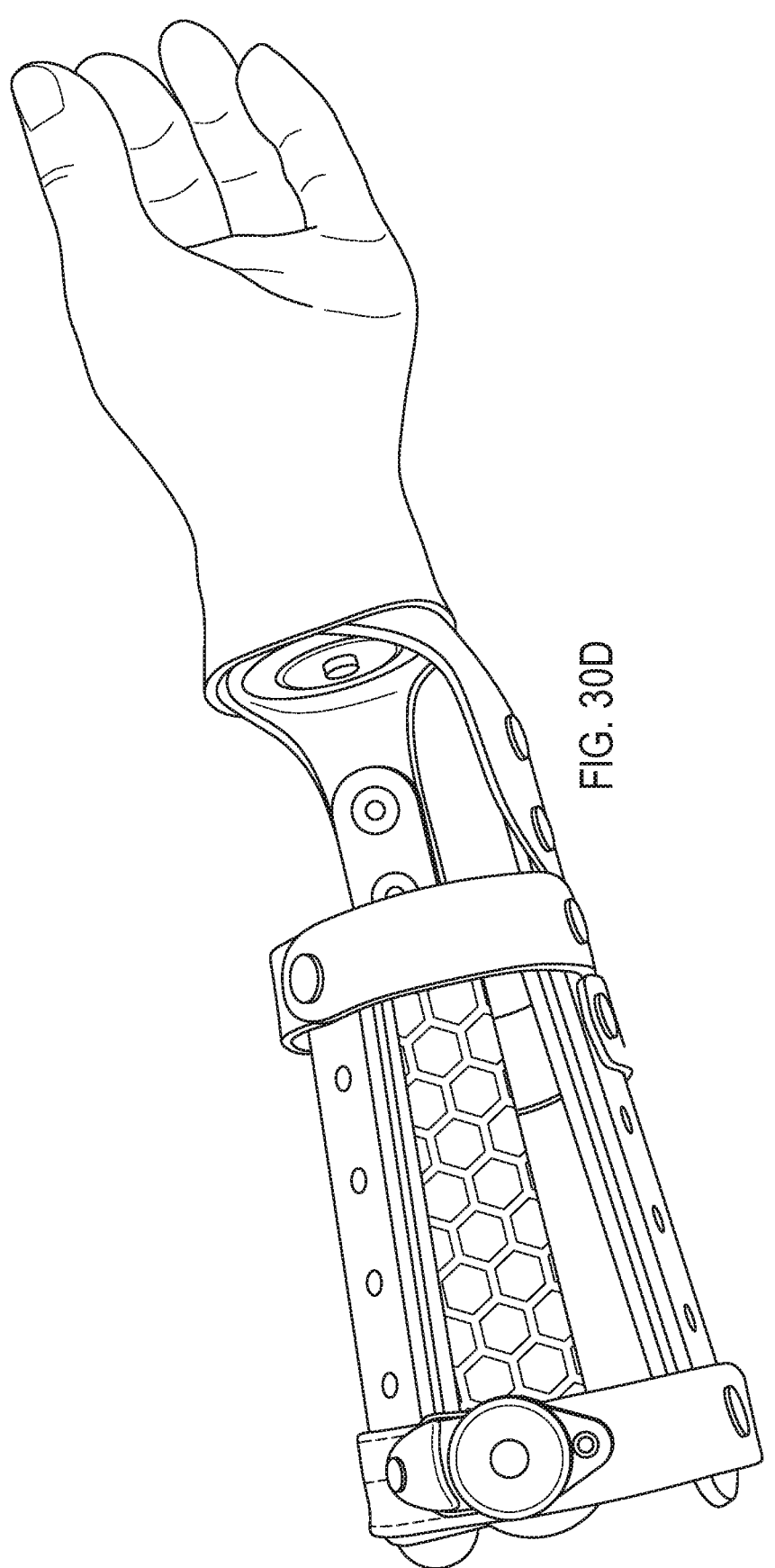

FIG. 30D generally illustrates an embodiment used in a transradial application.

Figure 30E:
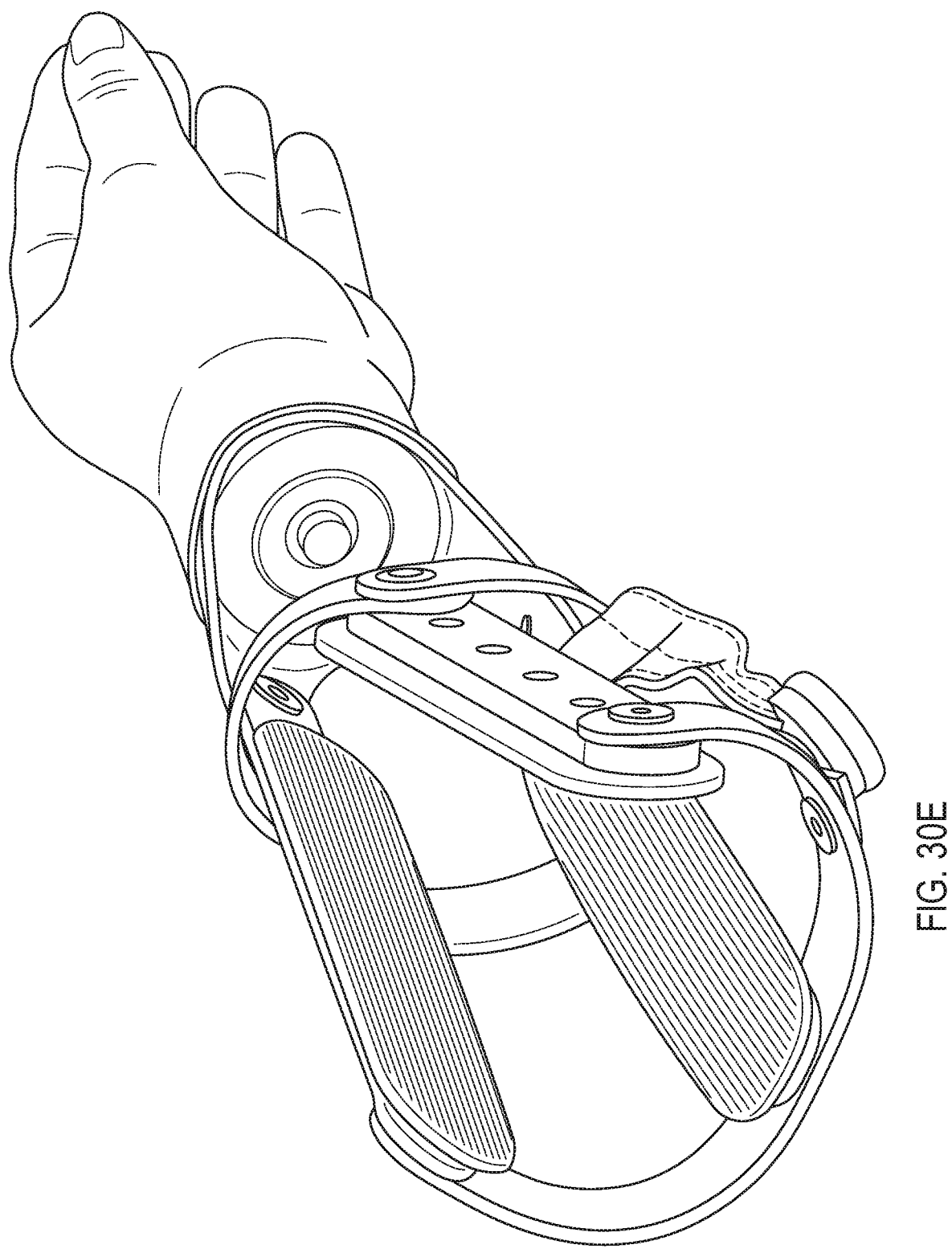

FIG. 30E generally illustrates an embodiment used in a transradial application.

Figure 31A:
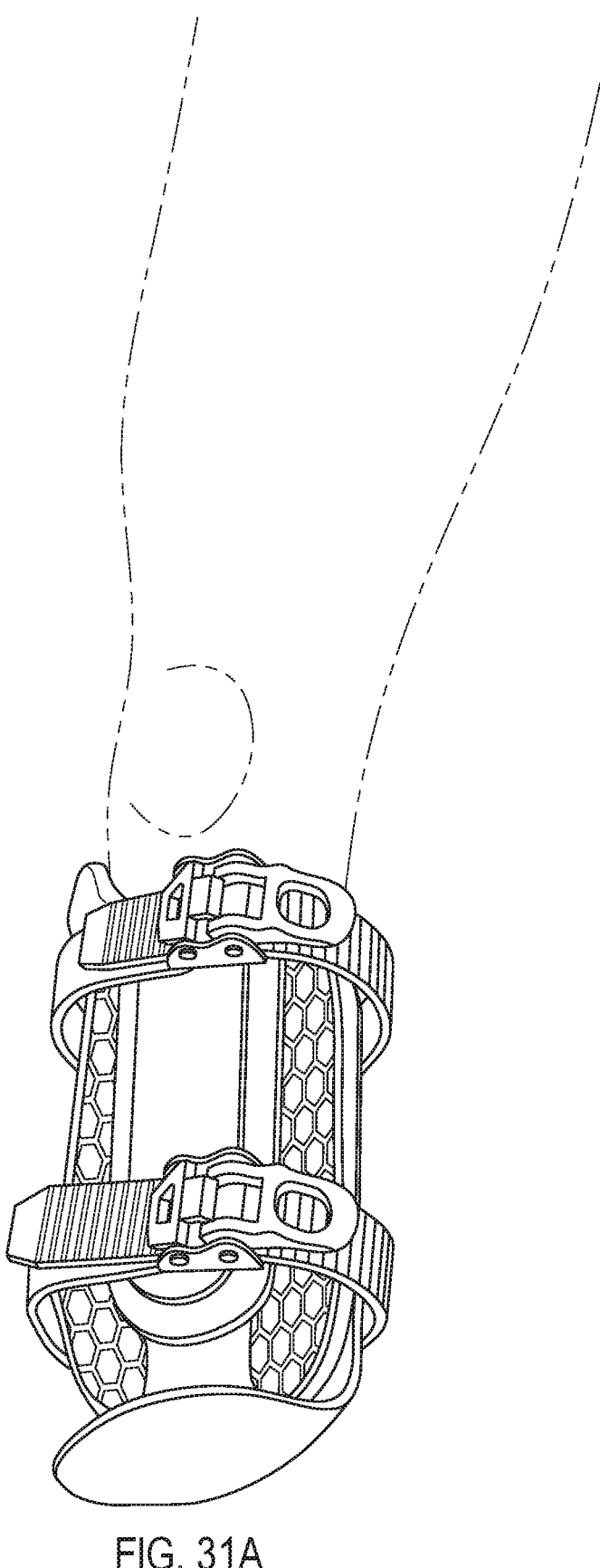

FIG. 31A generally illustrates an embodiment used in a transtibial application.

Figure 31B:
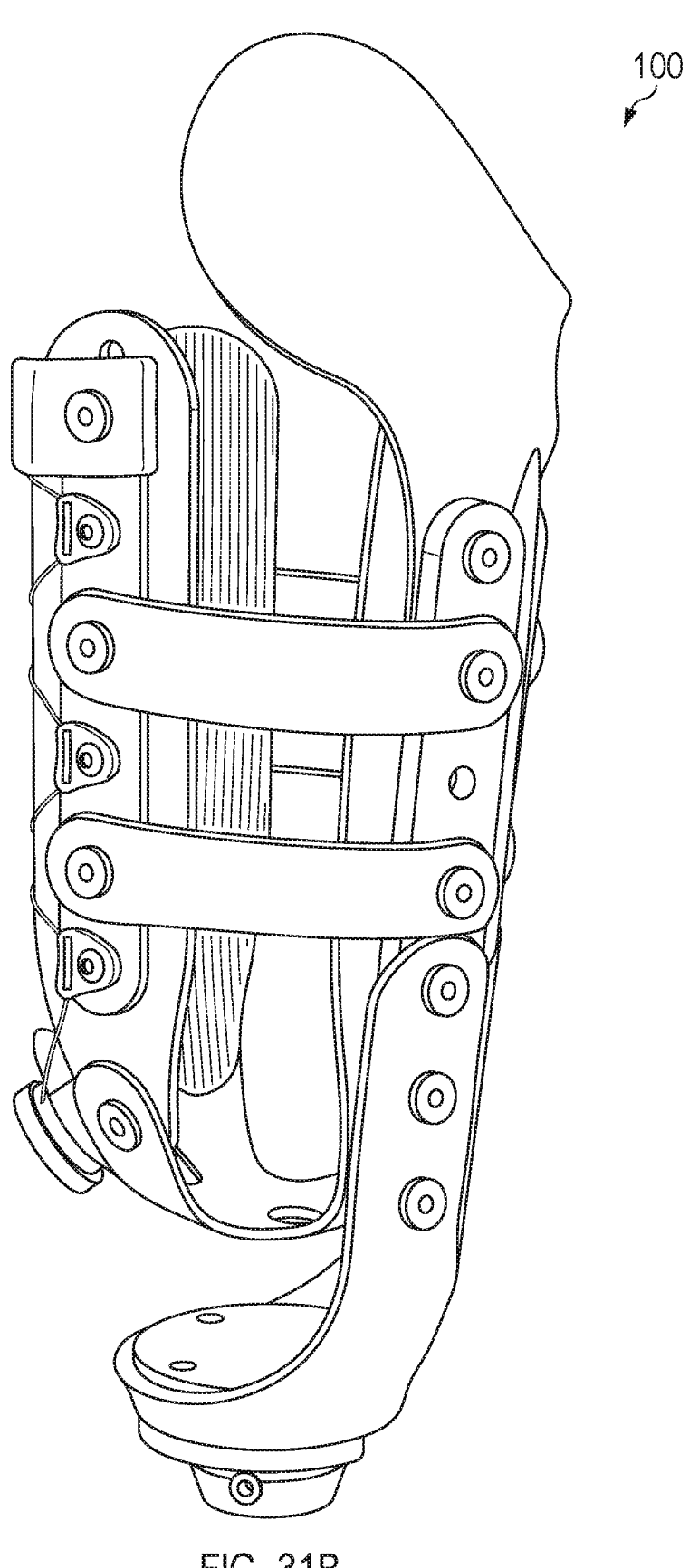

FIG. 31B generally illustrates an embodiment used in a transtibial application.

Figure 31C:
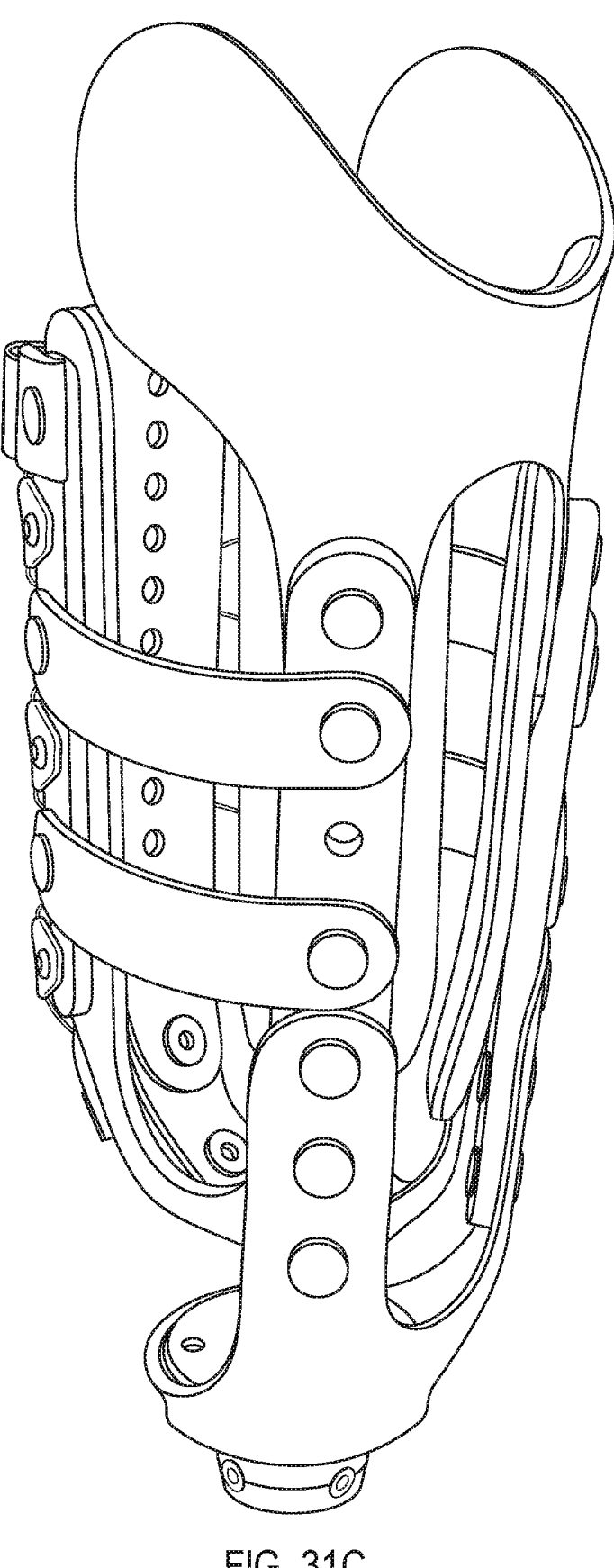

FIG. 31C generally illustrates an embodiment used in a transtibial application.

Figure 31D:
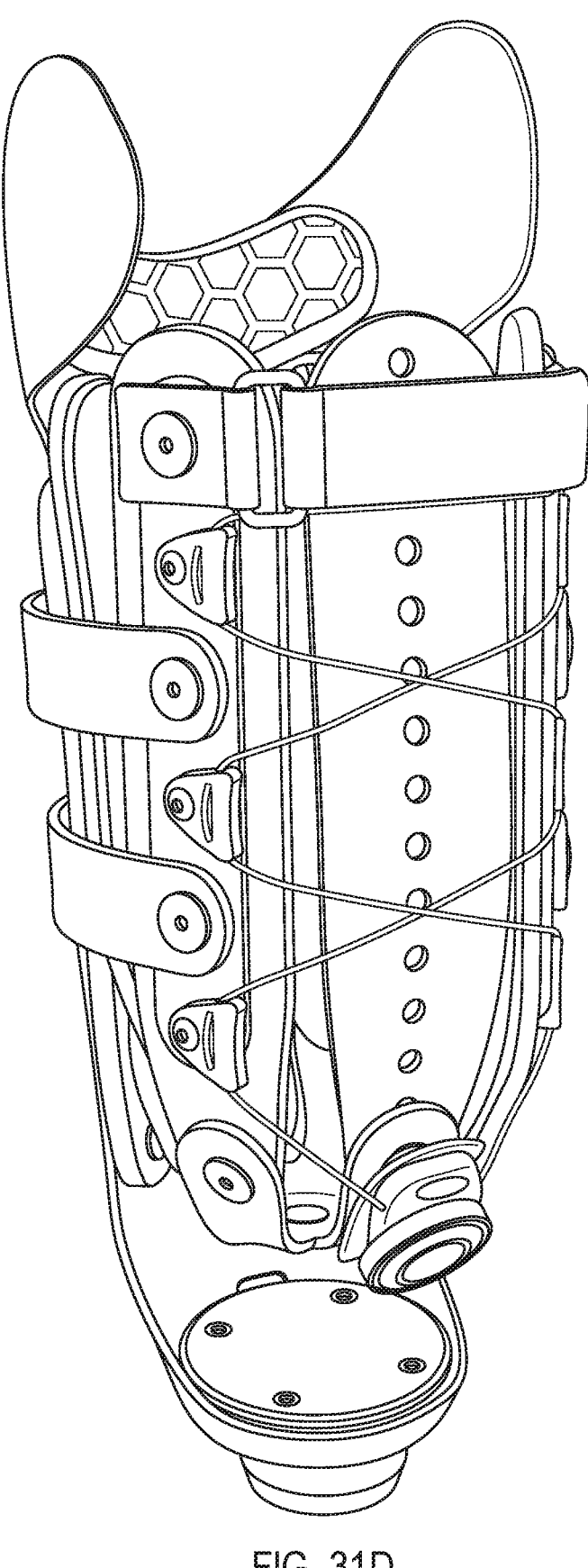

FIG. 31D generally illustrates an embodiment used in a transtibial application.

Figure 31E:
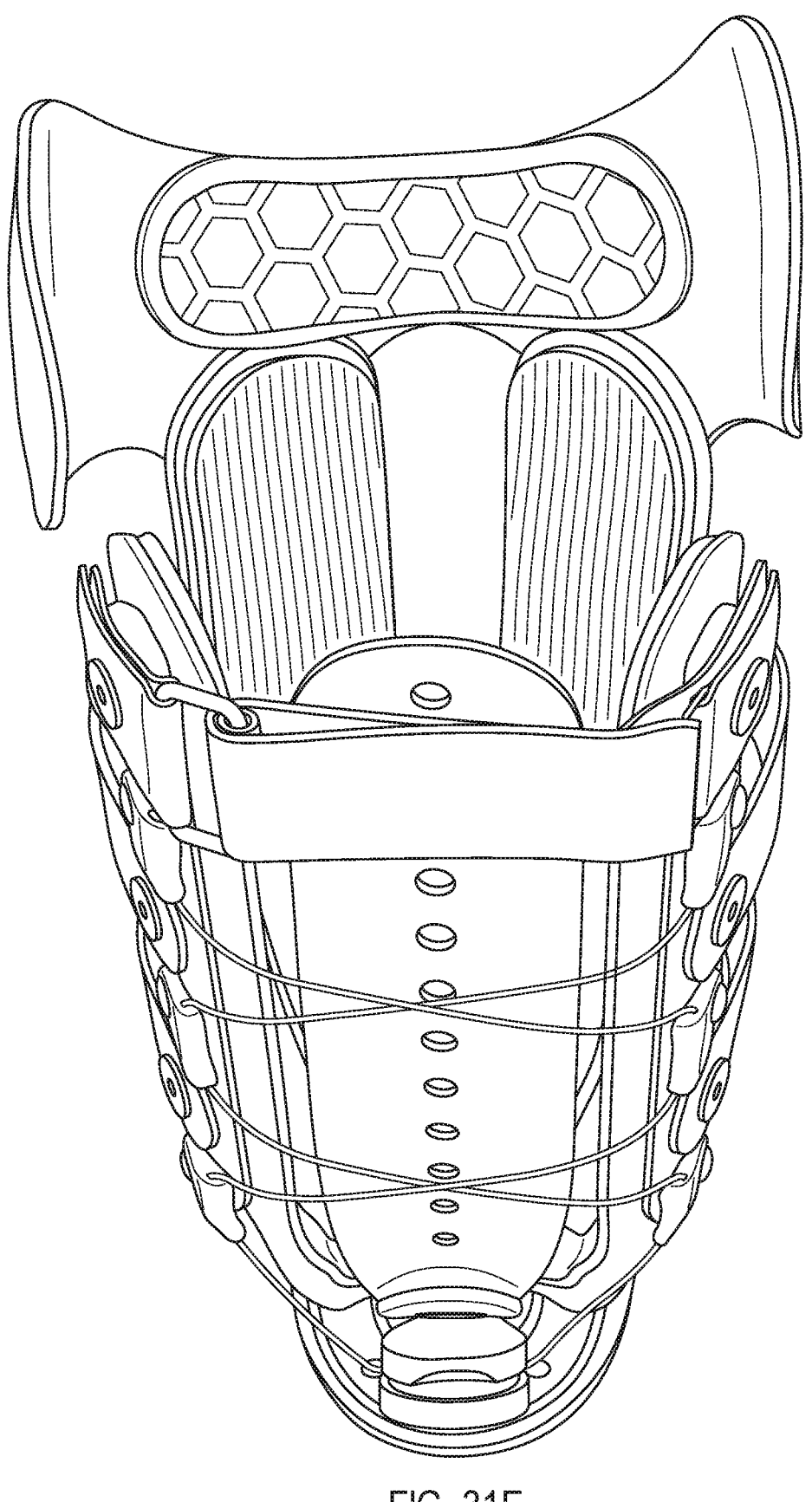

FIG. 31E generally illustrates an embodiment used in a transtibial application.

Figure 31F:
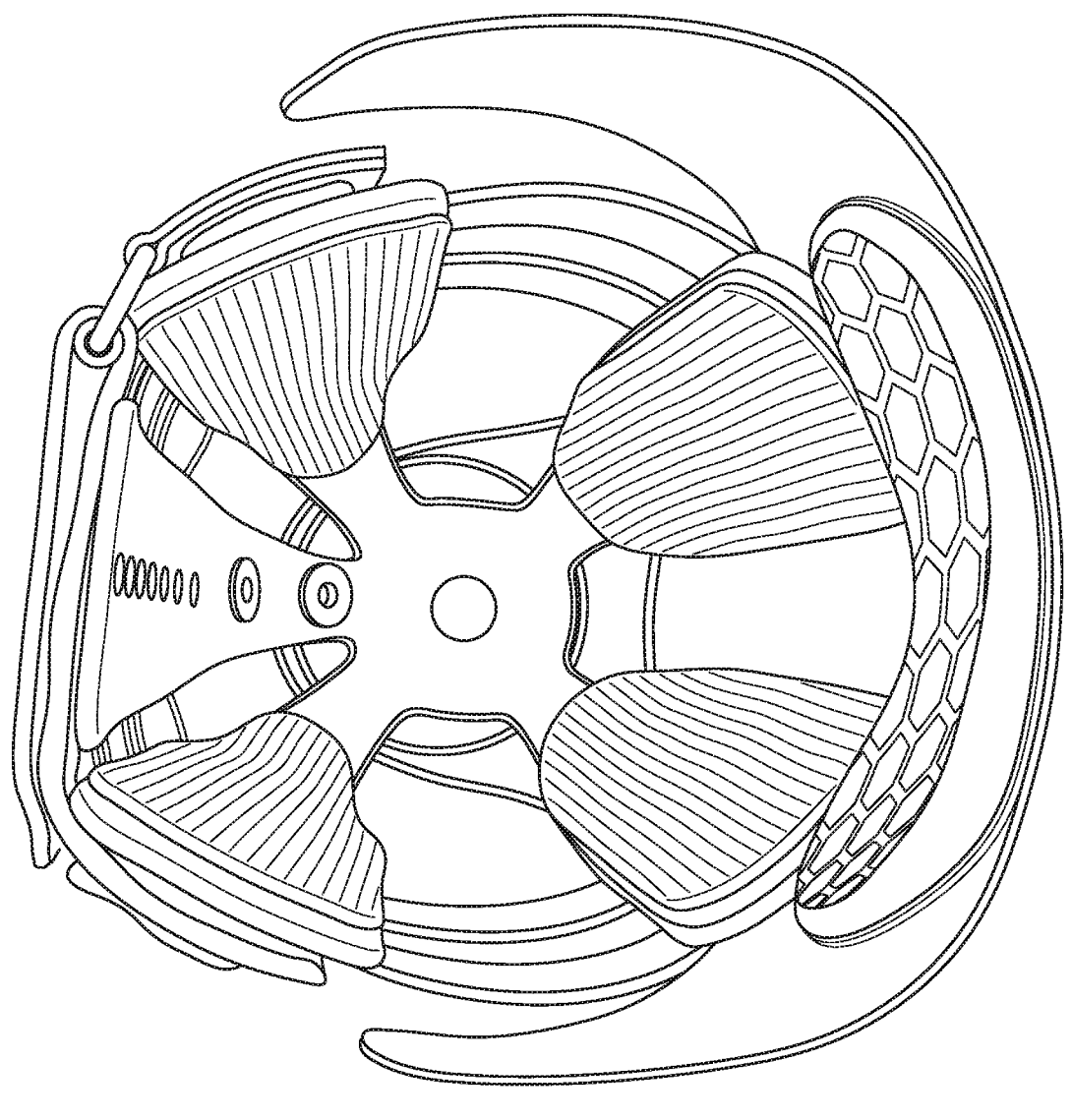

FIG. 31F generally illustrates an embodiment used in a transtibial application.

Figure 31G:
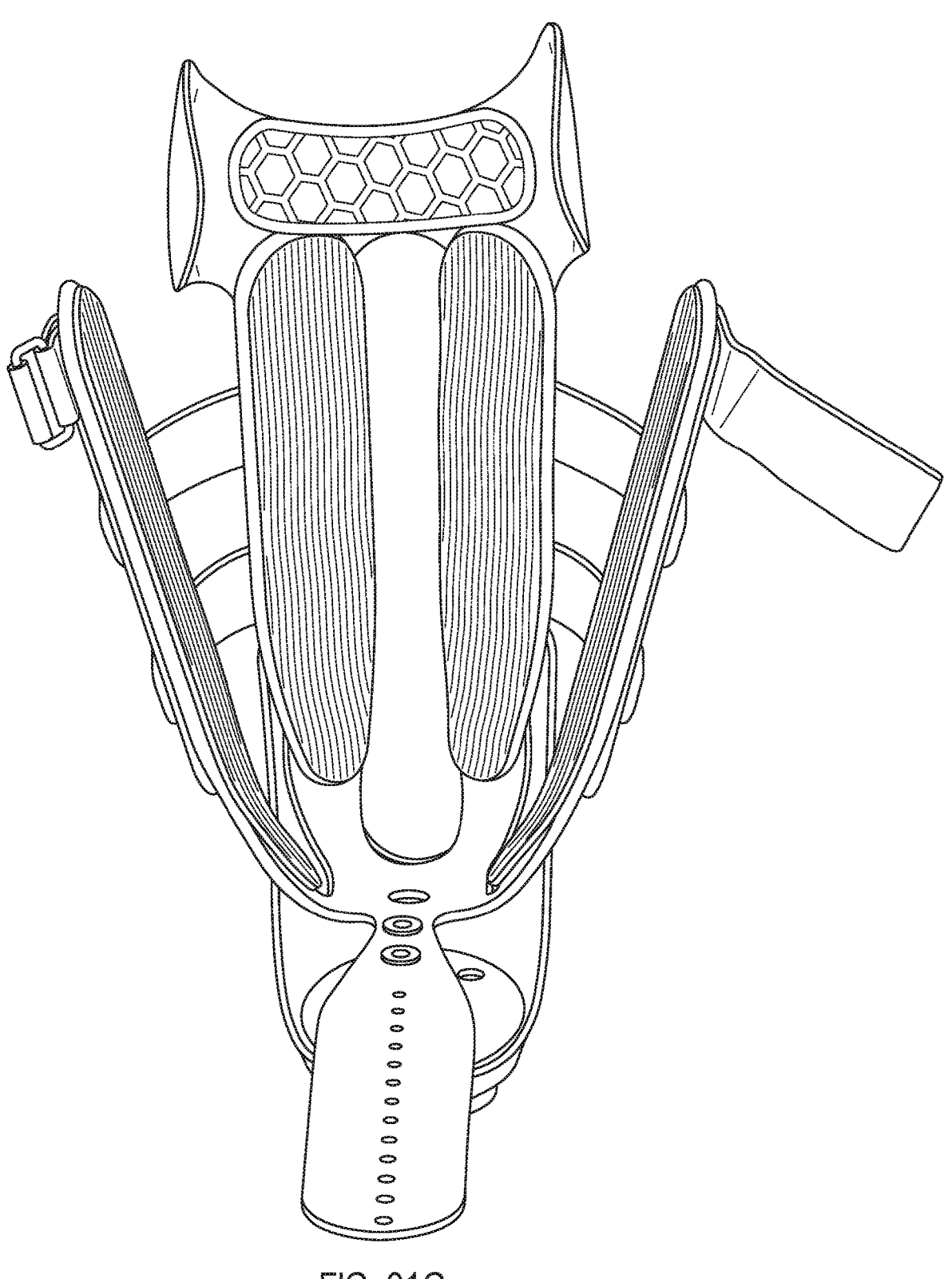

FIG. 31G generally illustrates an embodiment used in a transtibial application.

Figure 32:
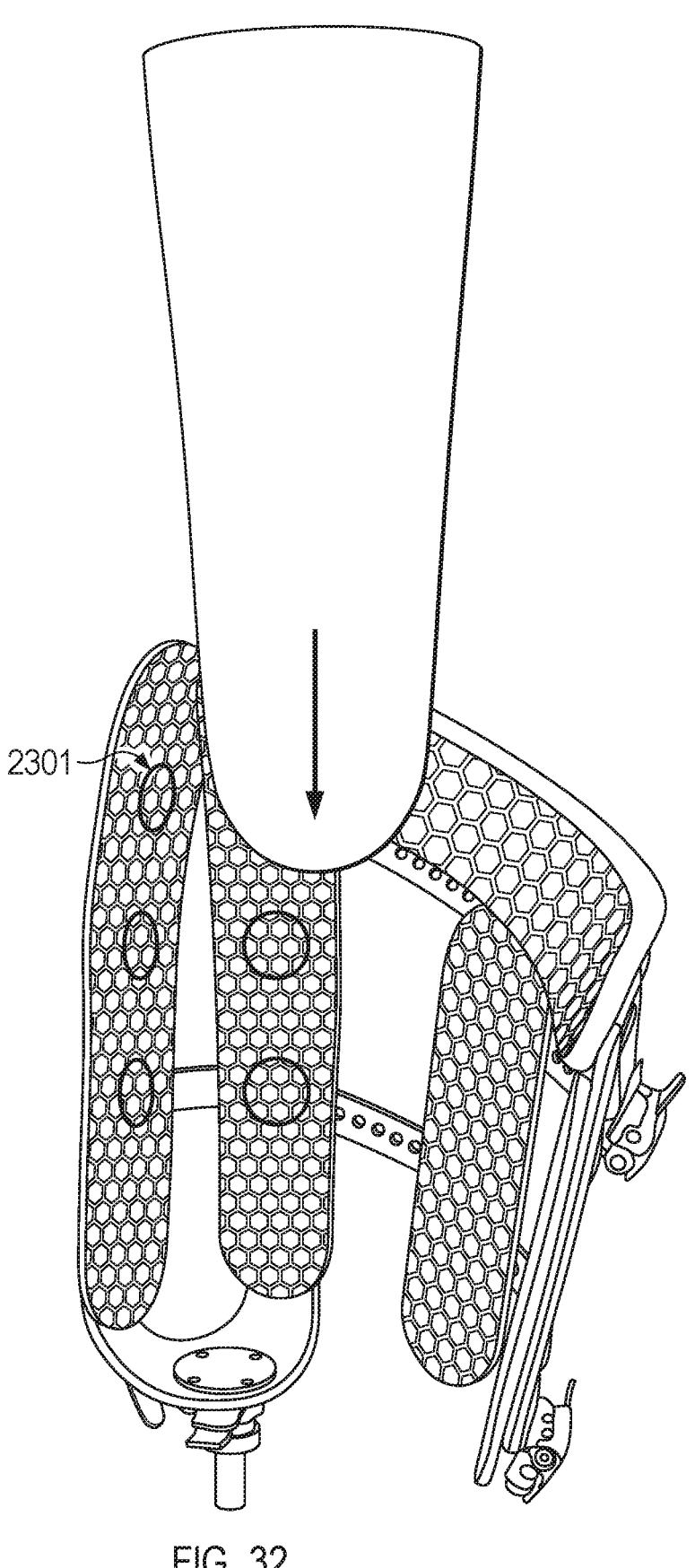

FIG. 32 illustrates the use of a gel liner or the like with an embodiment of a socket interface.

Figure 33:
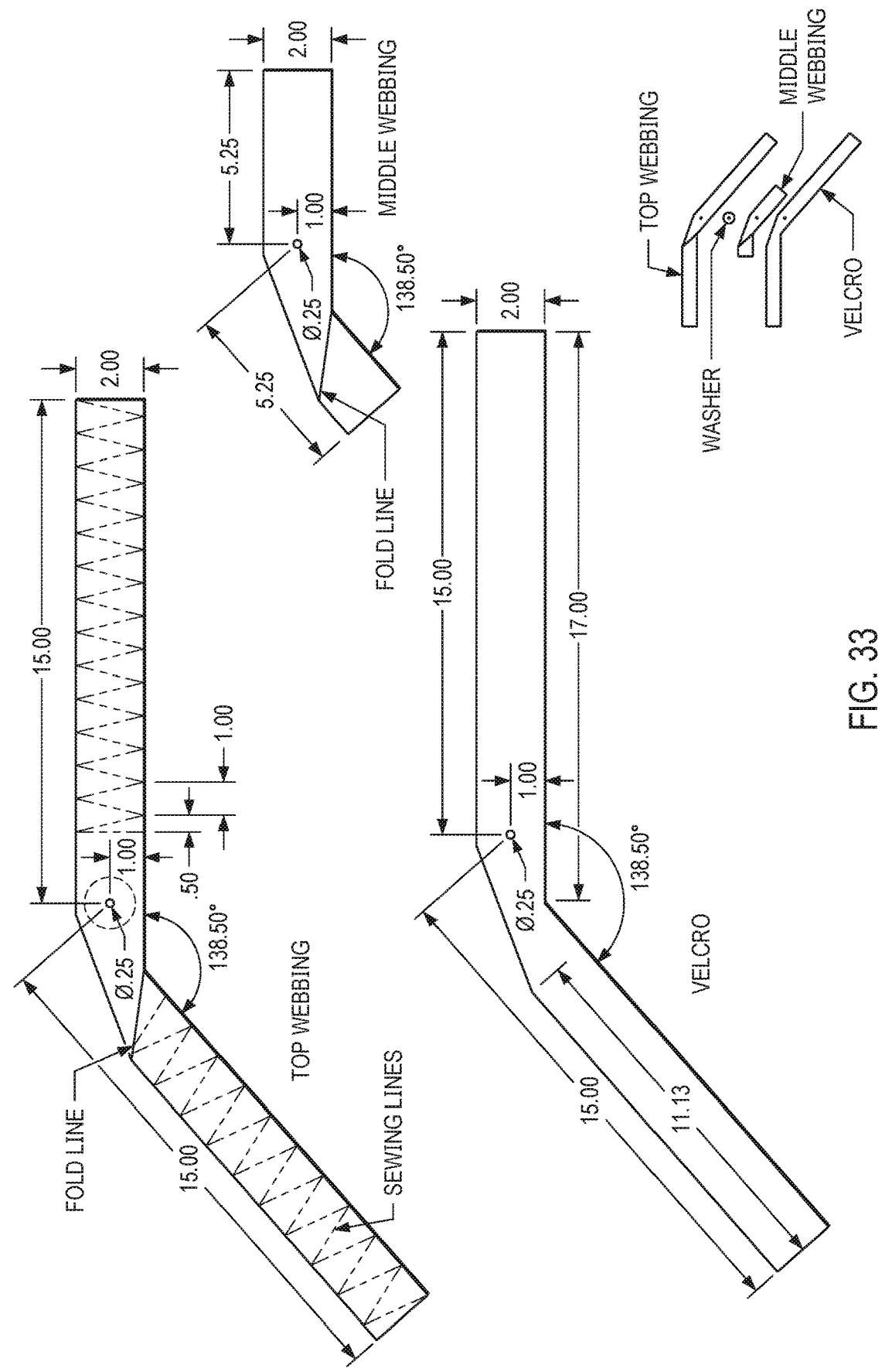

FIG. 33 illustrates a schematic of a swing brim webbing and materials for assembly.

Figures 34A, 34B, 34C, 34D:
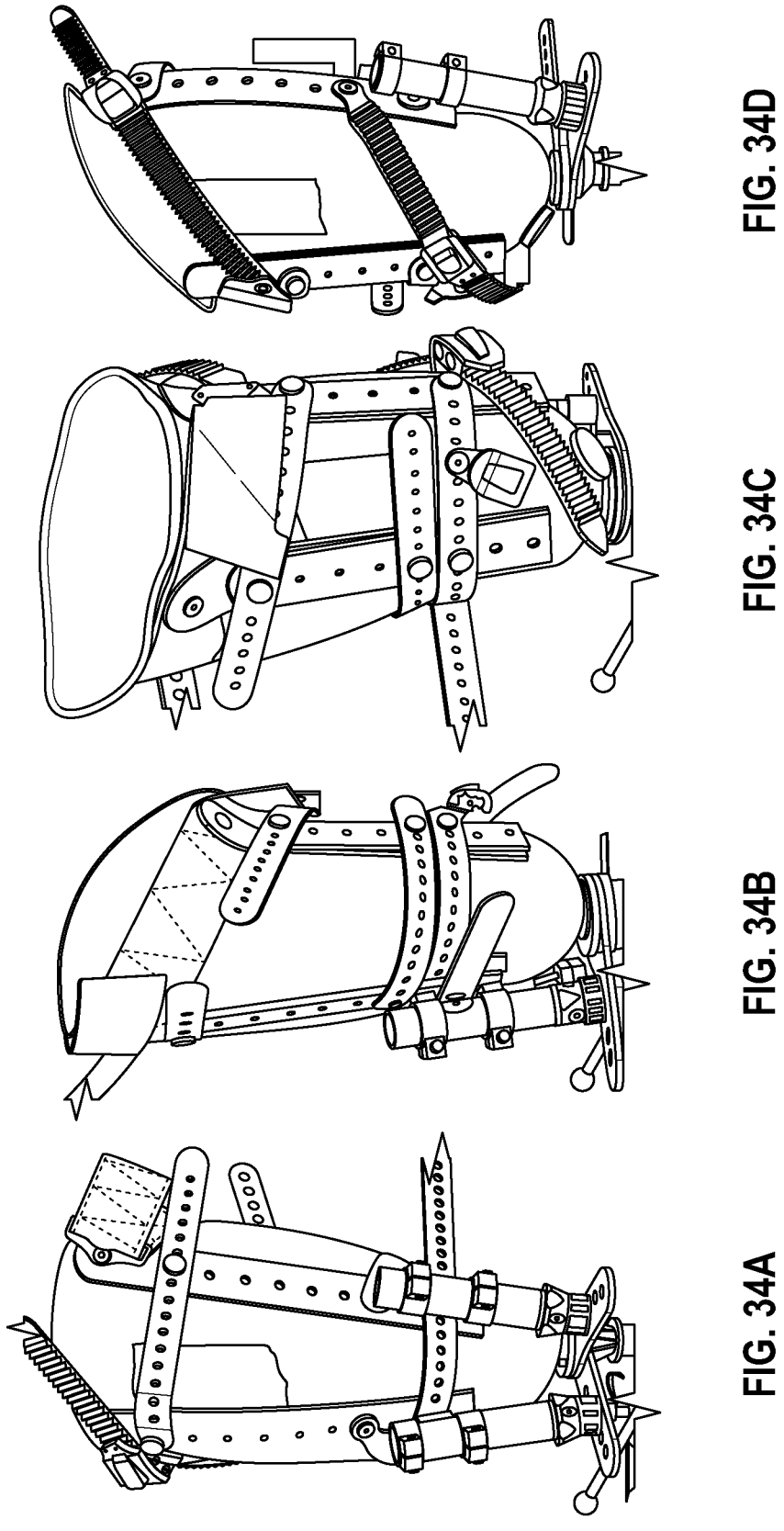

FIG. 34A illustrates lateral, posterior, medial, and anterior assembly of a socket less socket and swing brim around a conventional flexible inner socket to provide additional conformity for a user.

FIG. 34B illustrates lateral, posterior, medial, and anterior assembly of a socket less socket and swing brim around a conventional flexible inner socket to provide additional conformity for a user.

FIG. 34C illustrates lateral, posterior, medial, and anterior assembly of a socket less socket and swing brim around a conventional flexible inner socket to provide additional conformity for a user.

FIG. 34D illustrates lateral, posterior, medial, and anterior assembly of a socket less socket and swing brim around a conventional flexible inner socket to provide additional conformity for a user.

Figures 35A, 35B, 35C, 35D:

FIG. 35A illustrates lateral, posterior, medial, and anterior proposed trim lines of a flexible inner socket compared to conventional socket trimlines.

FIG. 35B illustrates lateral, posterior, medial, and anterior proposed trim lines of a flexible inner socket compared to conventional socket trimlines.

FIG. 35C illustrates lateral, posterior, medial, and anterior proposed trim lines of a flexible inner socket compared to conventional socket trimlines.

FIG. 35D illustrates lateral, posterior, medial, and anterior proposed trim lines of a flexible inner socket compared to conventional socket trimlines.

Figures 36A, 36B, 36C, 36D:
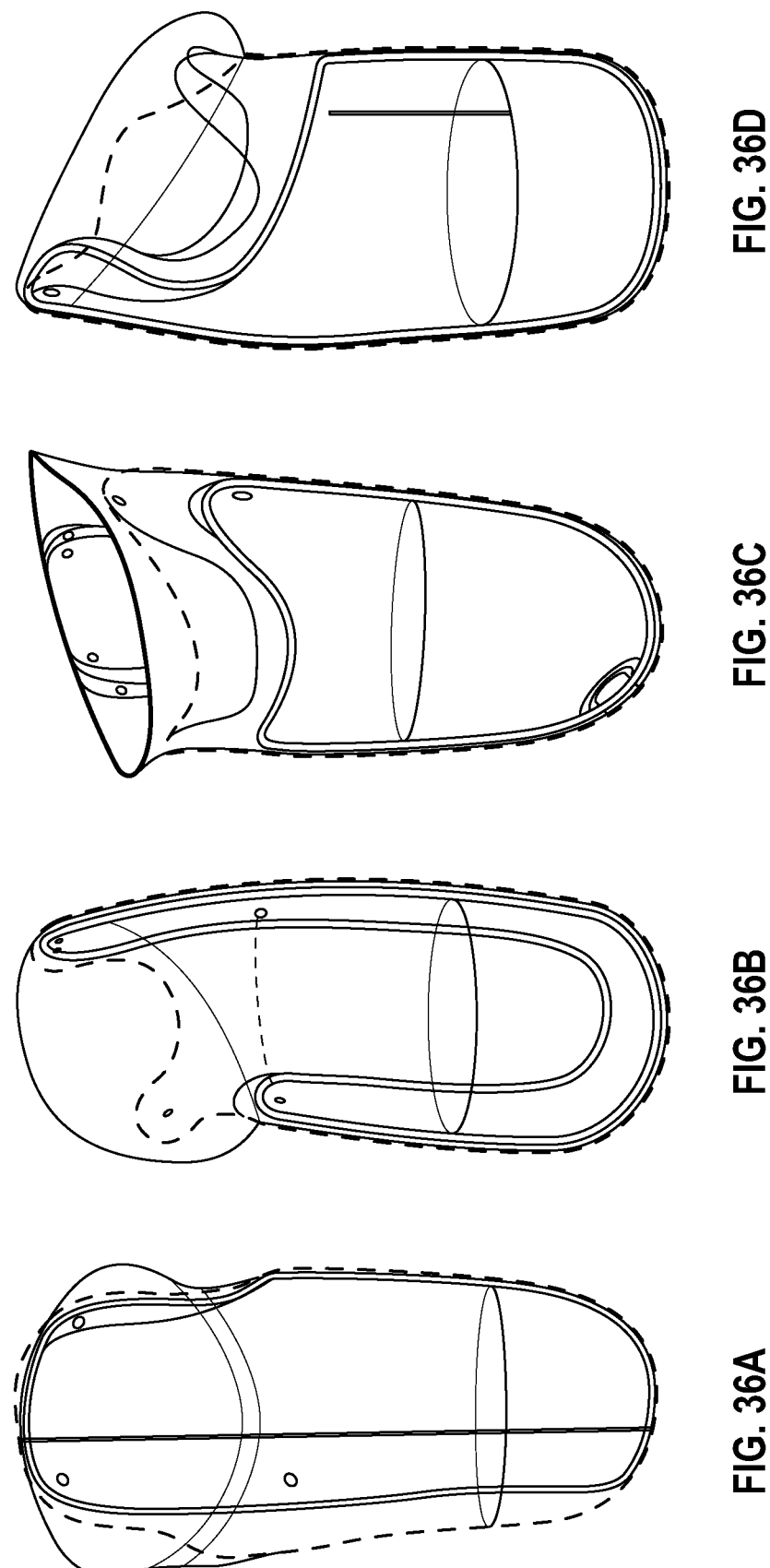

FIG. 36A illustrates lateral, posterior, medial, and anterior proposed trim lines of a conventional frame as trimmed down to accommodate a swing brim.

FIG. 36B illustrates lateral, posterior, medial, and anterior proposed trim lines of a conventional frame as trimmed down to accommodate a swing brim.

FIG. 36C illustrates lateral, posterior, medial, and anterior proposed trim lines of a conventional frame as trimmed down to accommodate a swing brim.

FIG. 36D illustrates lateral, posterior, medial, and anterior proposed trim lines of a conventional frame as trimmed down to accommodate a swing brim.

Figure 37A:
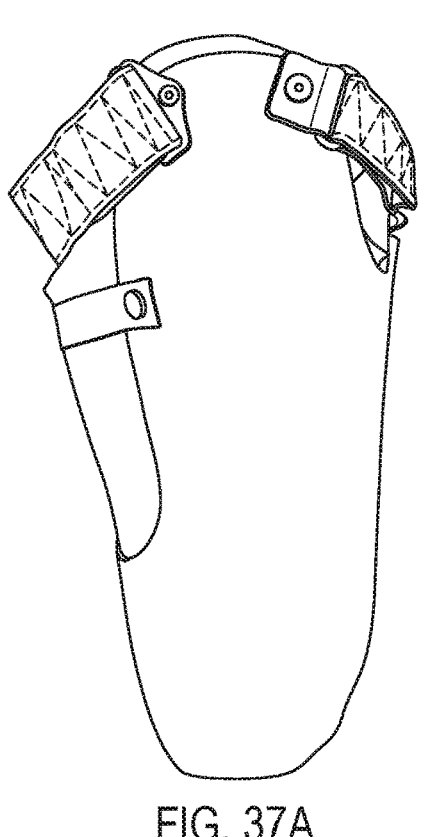

FIG. 37A illustrates lateral, posterior, medial, and anterior proposed assembly of a conventional socket with integrated swing brim after trim lines of the conventional inner socket and conventional frame to accommodate a flexible swing brim.

Figure 37B:
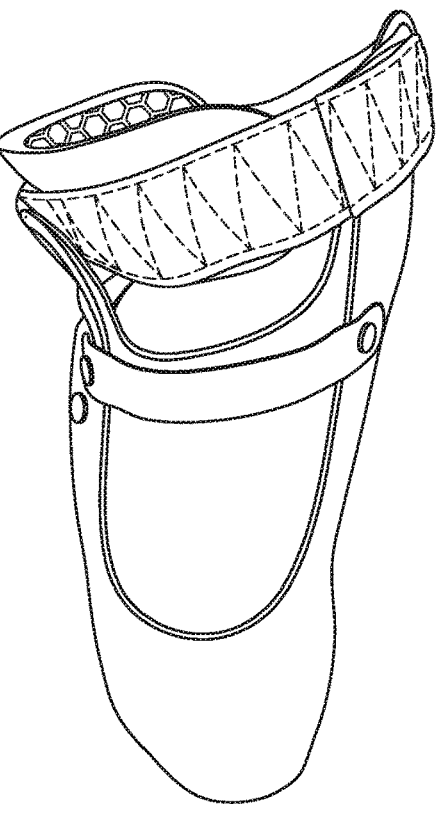

FIG. 37B illustrates lateral, posterior, medial, and anterior proposed assembly of a conventional socket with integrated swing brim after trim lines of the conventional inner socket and conventional frame to accommodate a flexible swing brim.

Figure 37C:
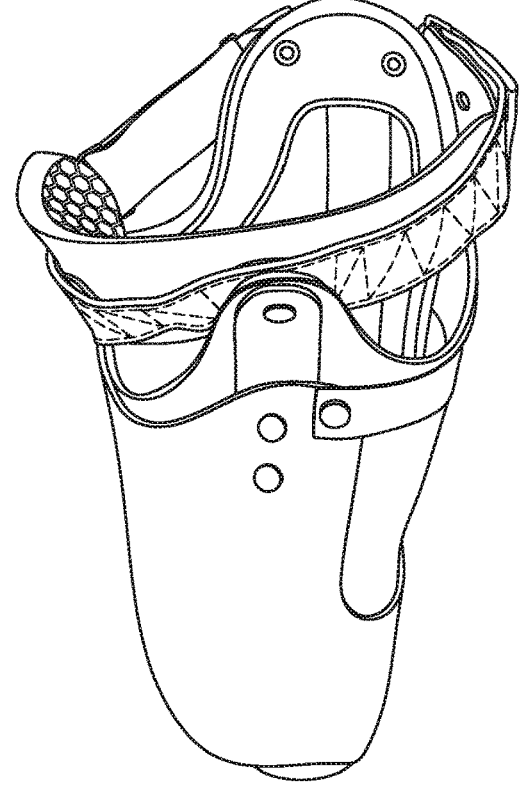

FIG. 37C illustrates lateral, posterior, medial, and anterior proposed assembly of a conventional socket with integrated swing brim after trim lines of the conventional inner socket and conventional frame to accommodate a flexible swing brim.

Figure 37D:
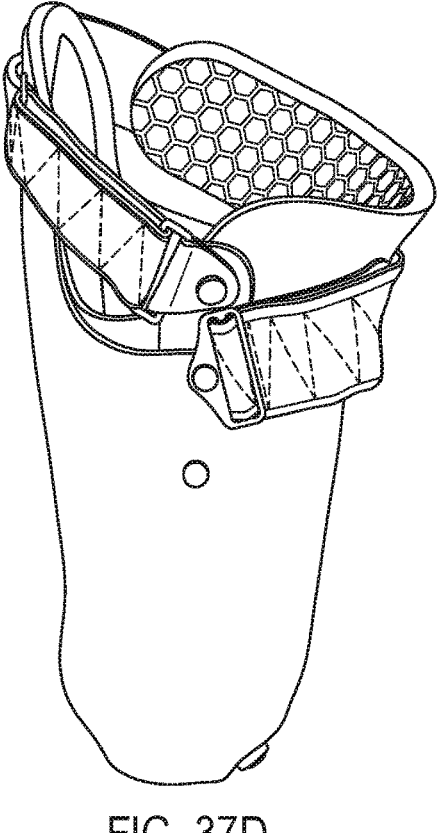

FIG. 37D illustrates lateral, posterior, medial, and anterior proposed assembly of a conventional socket with integrated swing brim after trim lines of the conventional inner socket and conventional frame to accommodate a flexible swing brim.

Figure 38:
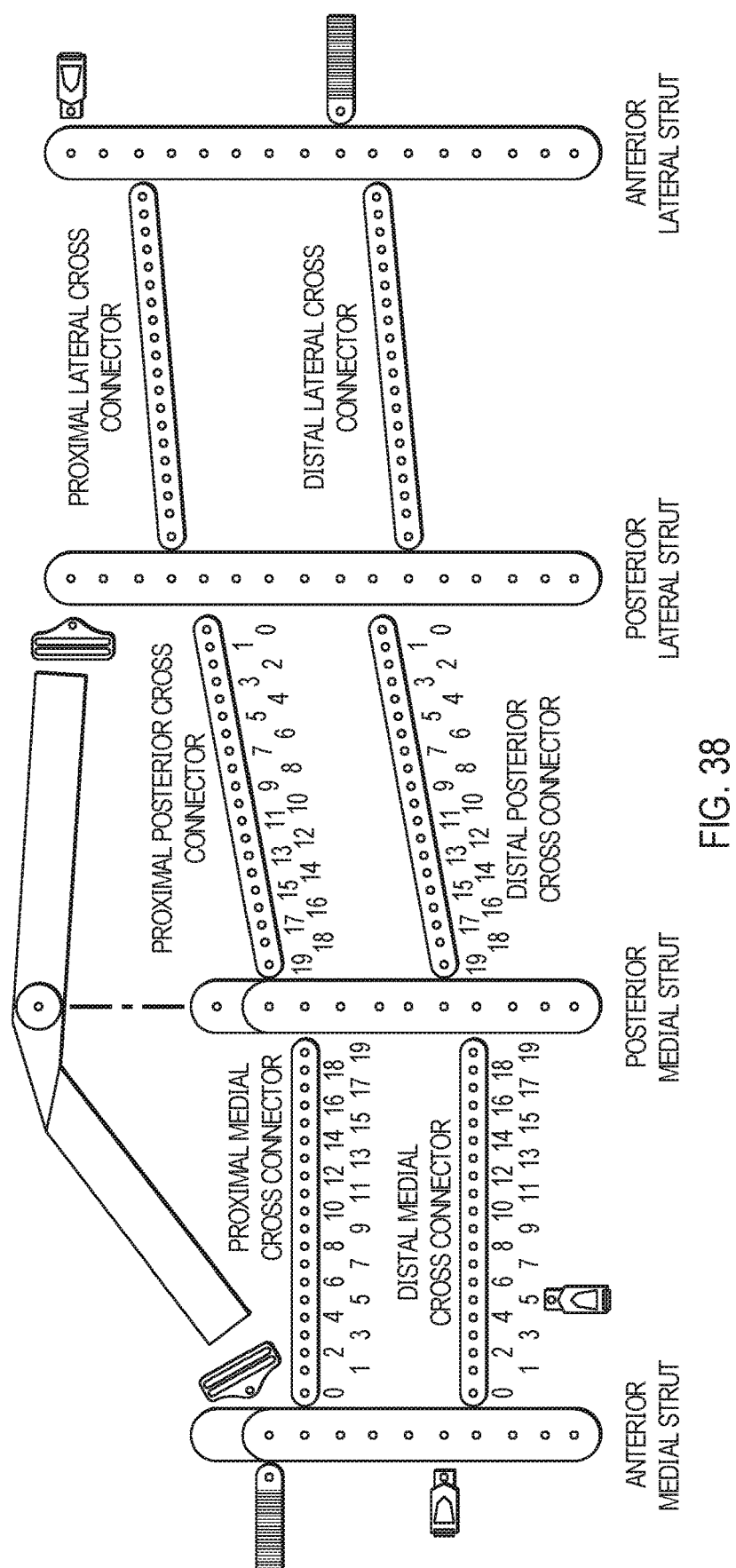

FIG. 38 illustrates a general schematic of an embodiment of a modular prosthetic socket in which sub-components may enable defined configuration assembly.

Figure 39A:
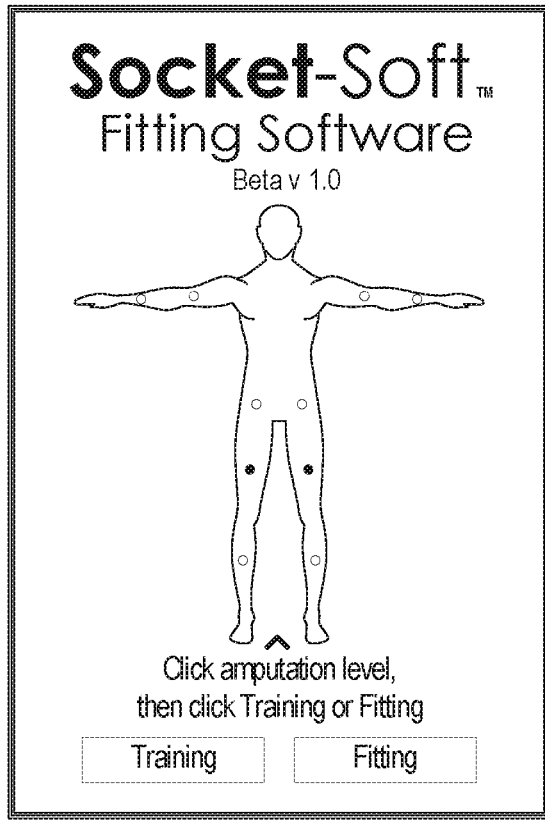
Figure 39A:
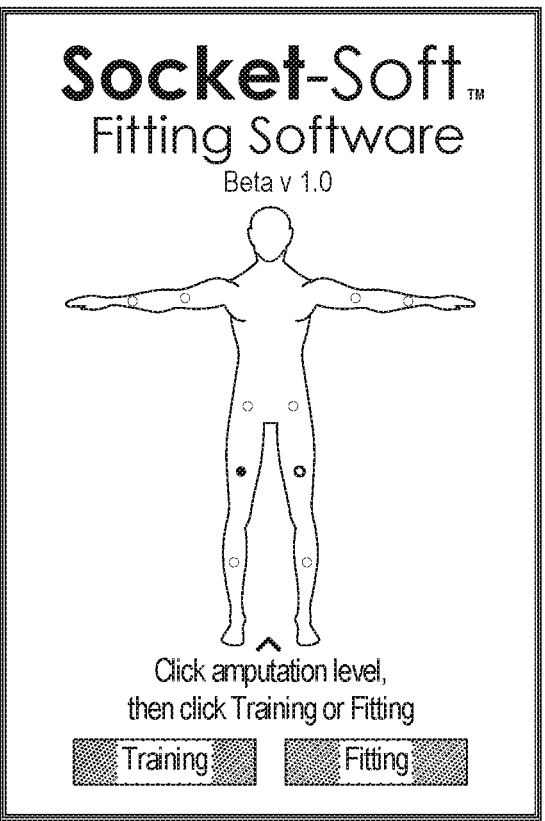
Figure 39A:
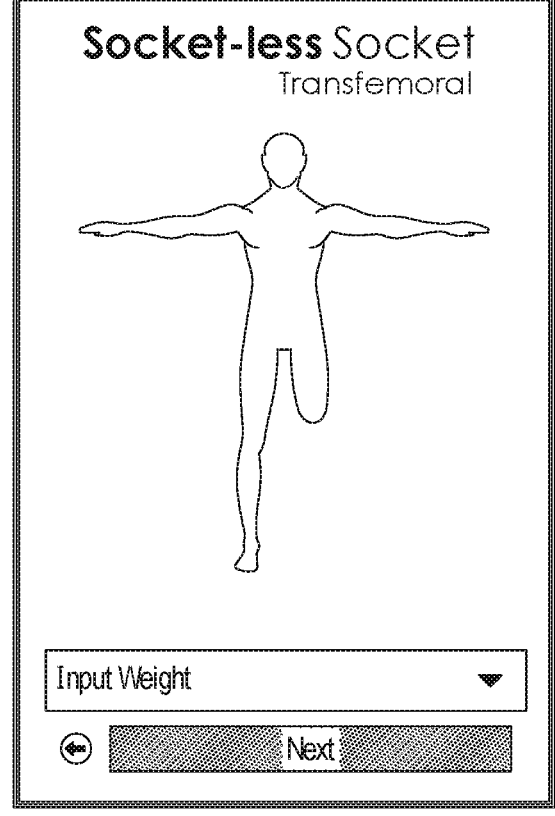
Figure 39A:
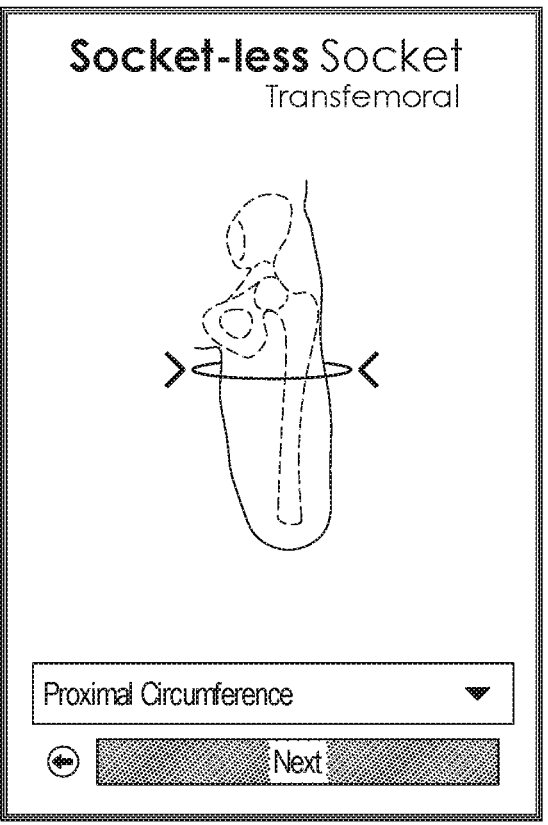
Figure 39A:
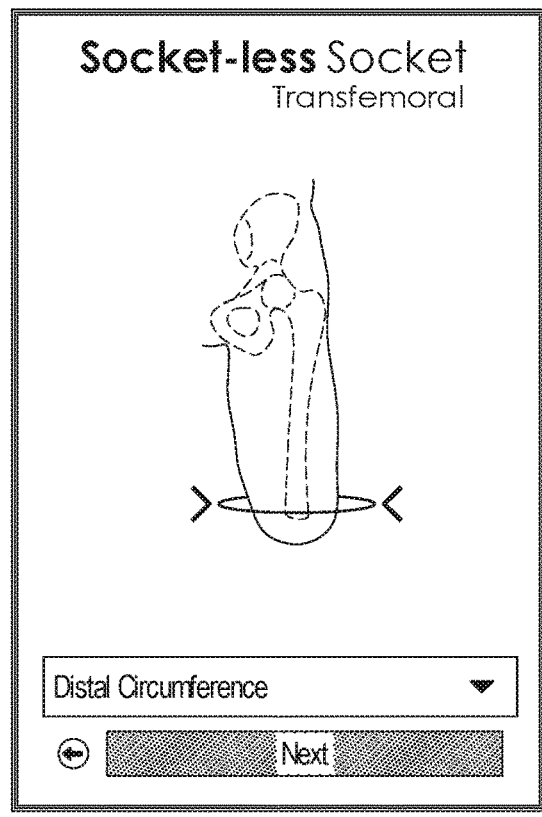
Figure 39A:
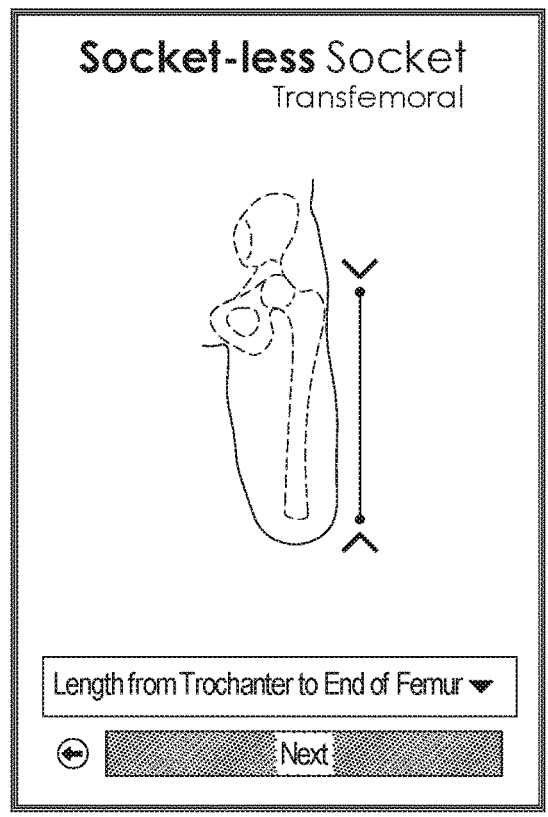
Figure 39A:
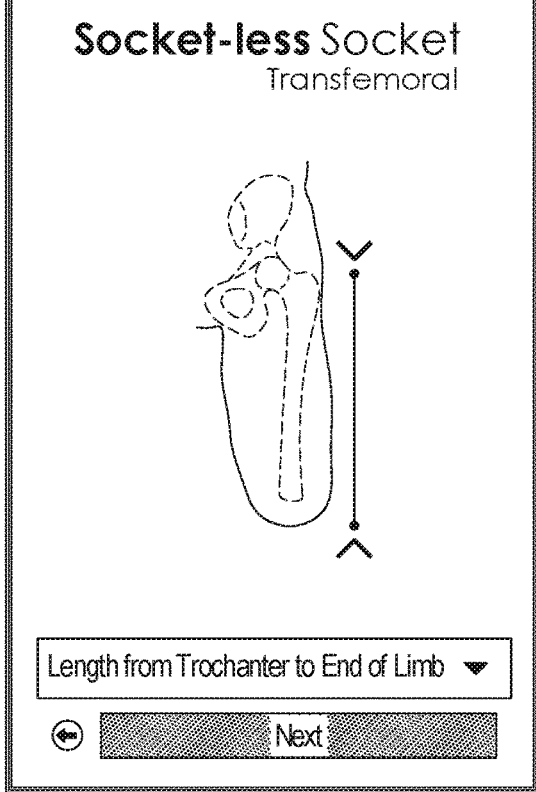
Figure 39A:
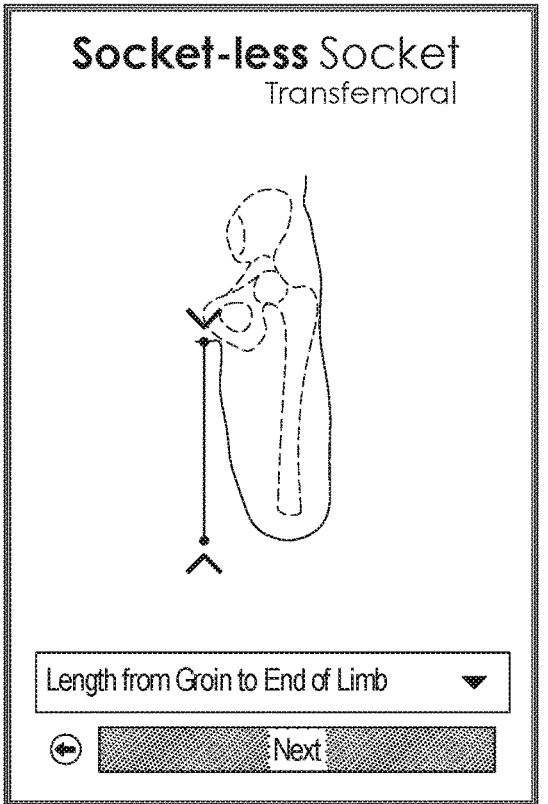
Figure 39A:
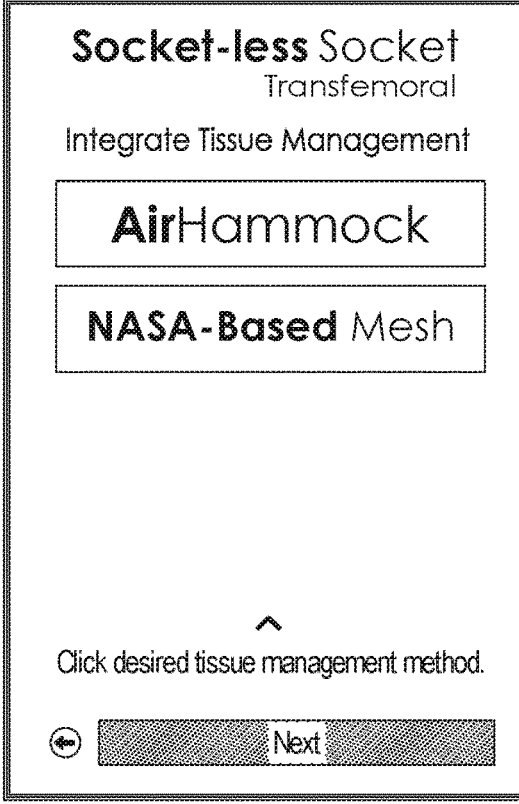
Figure 39A:
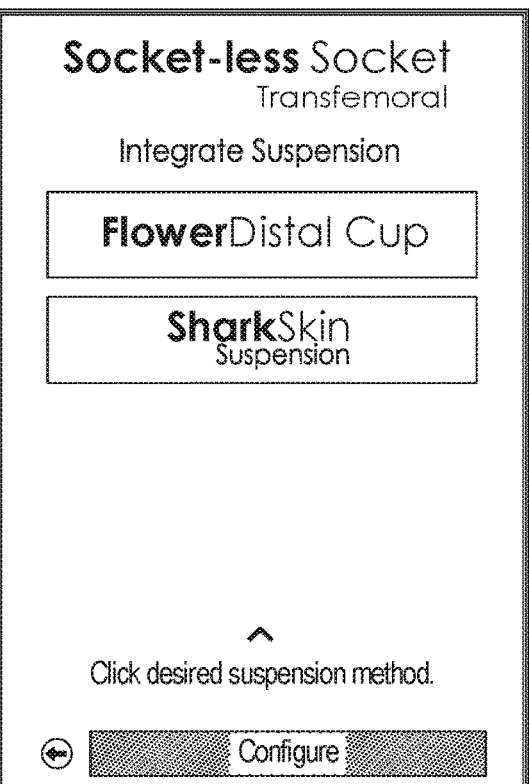
Figure 39A:
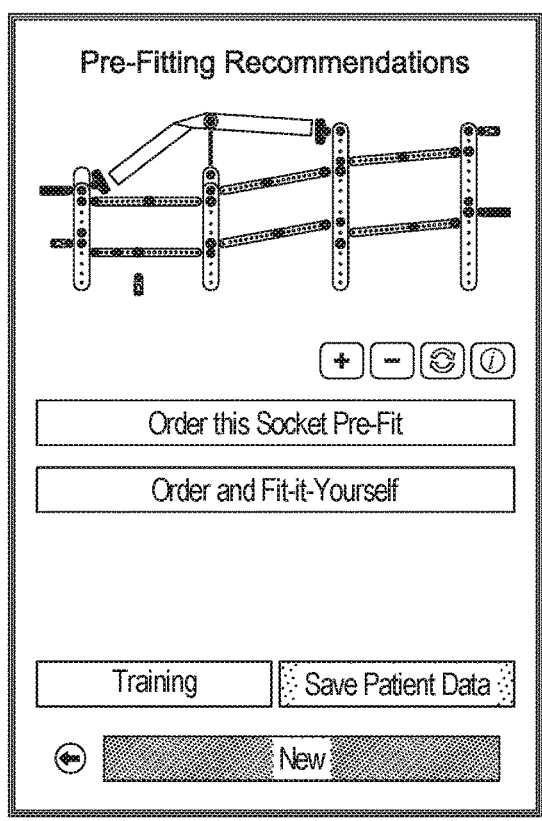

FIG. 39A illustrates a possible workflow of software, which may be used to input limb measurements and output a defined assembly configuration.

Figure 39B:
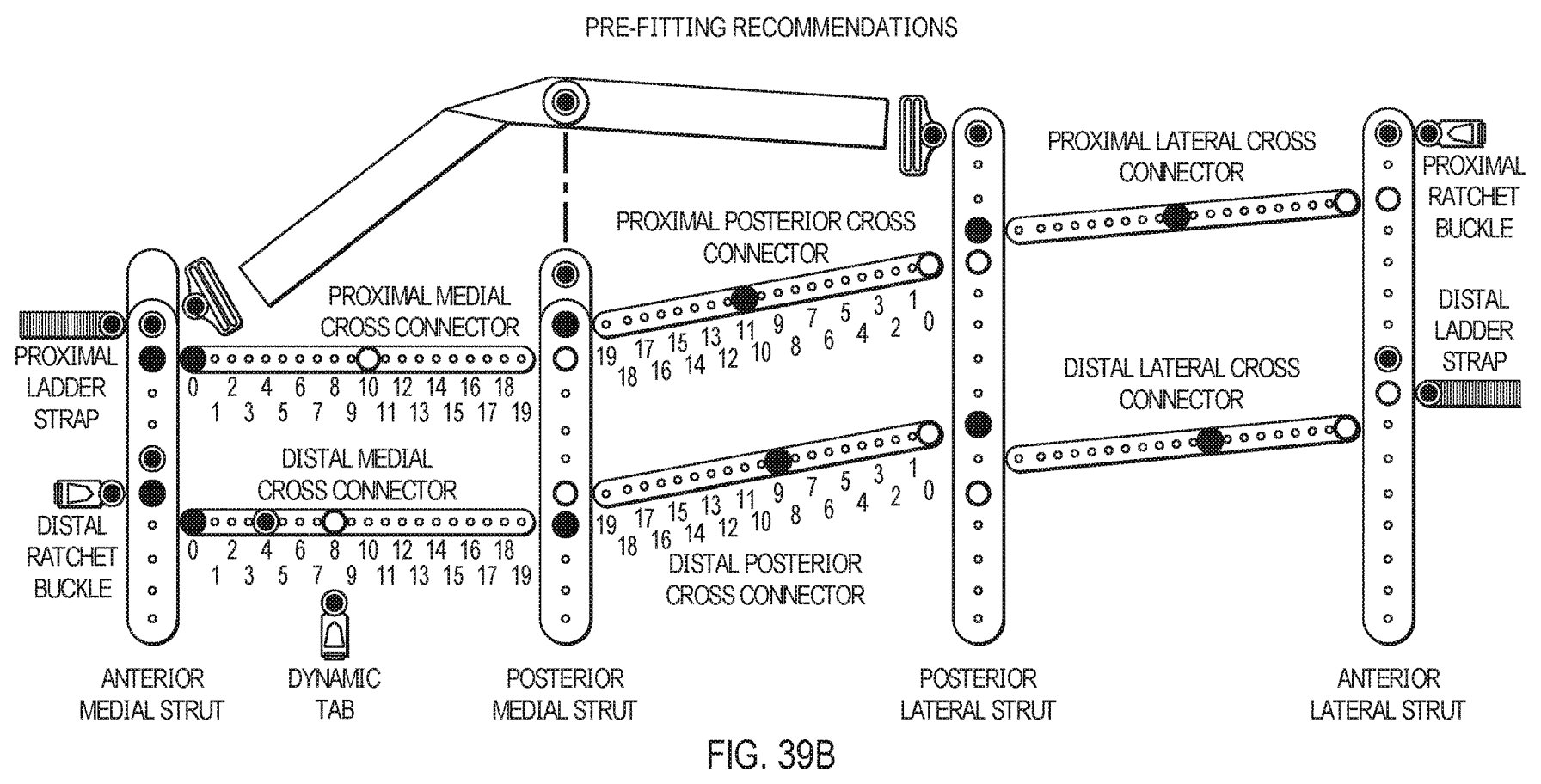

FIG. 39B illustrates a possible workflow of software, which may be used to input limb measurements and output a defined assembly configuration.

Figure 39C:
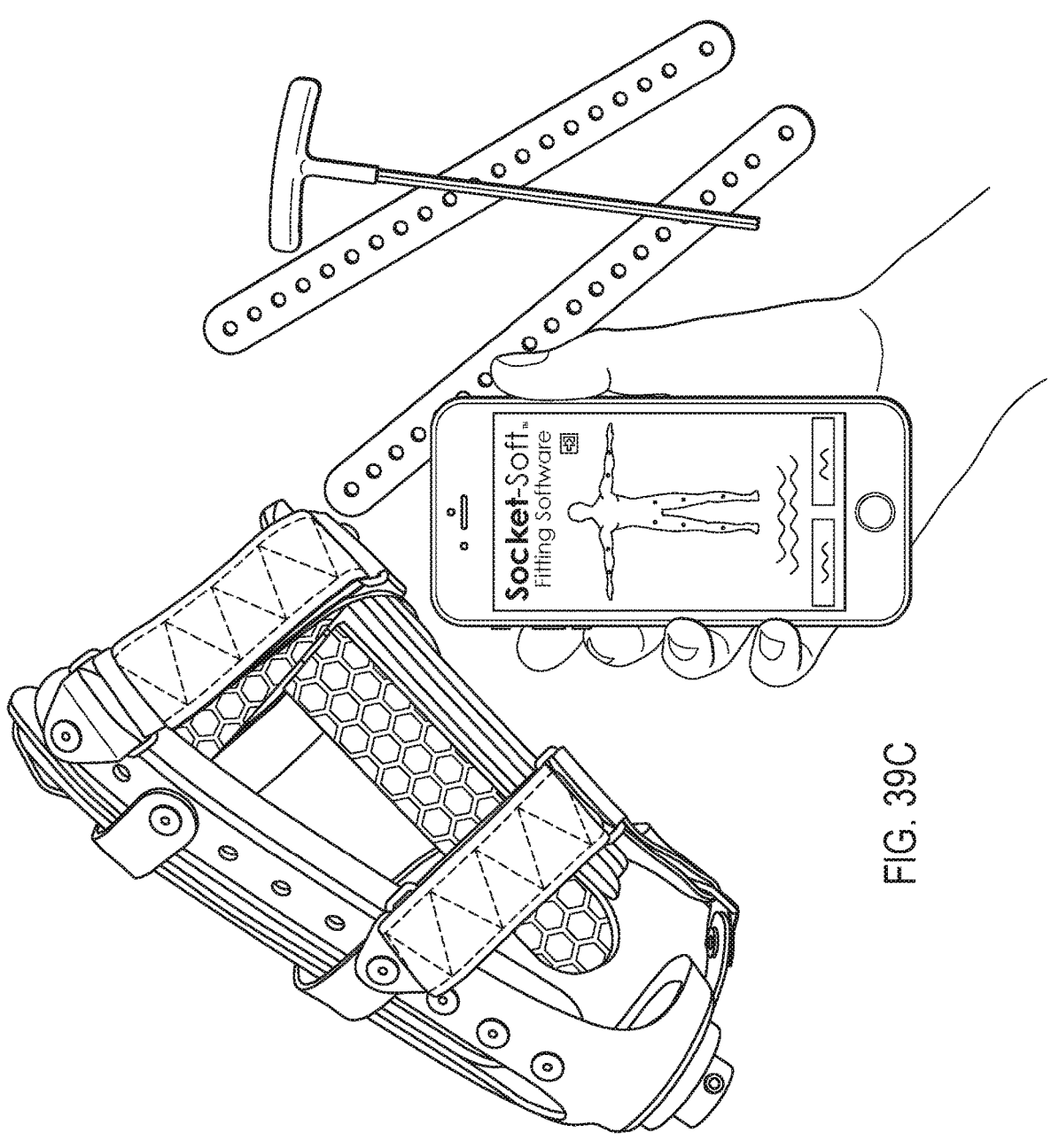

FIG. 39C illustrates a possible workflow of software, which may be used to input limb measurements and output a defined assembly configuration.

Figure 40A:
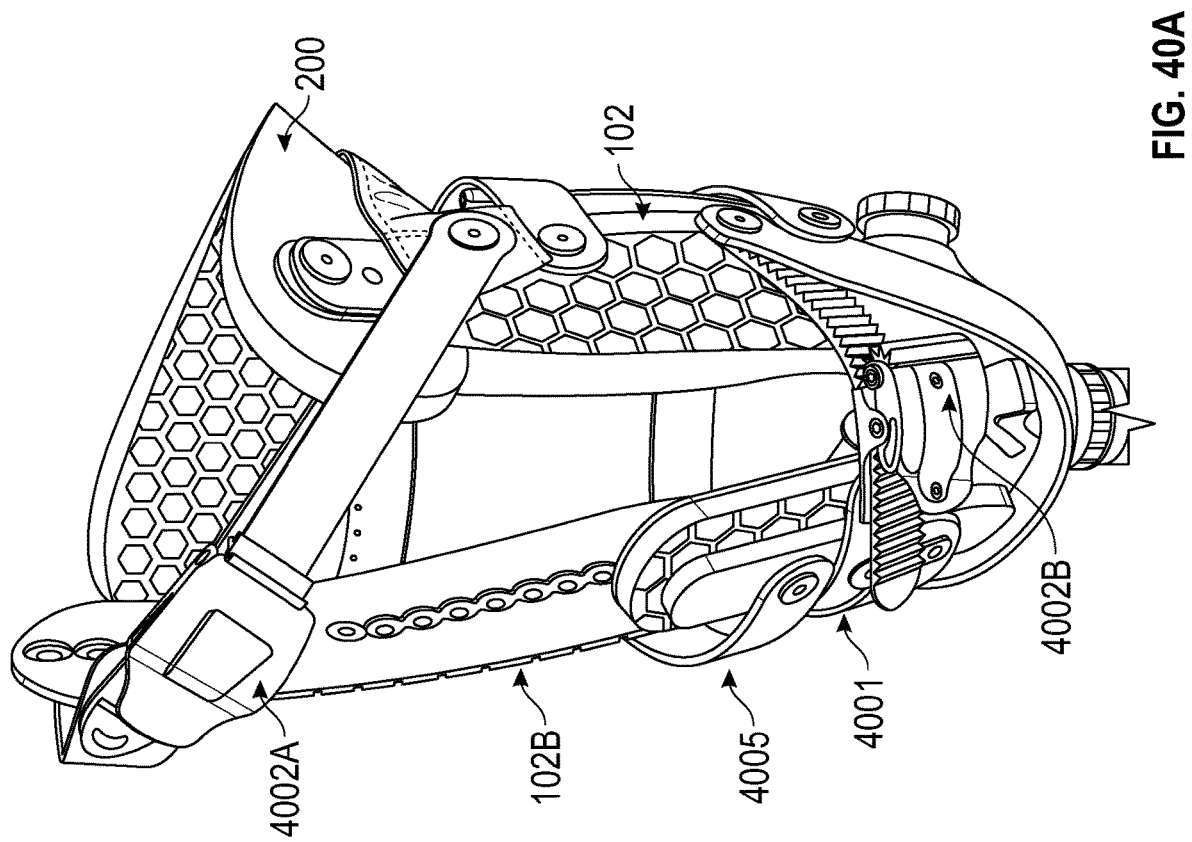

FIG. 40A generally illustrates another preferred embodiment in accordance with the current invention.

Figure 40B:
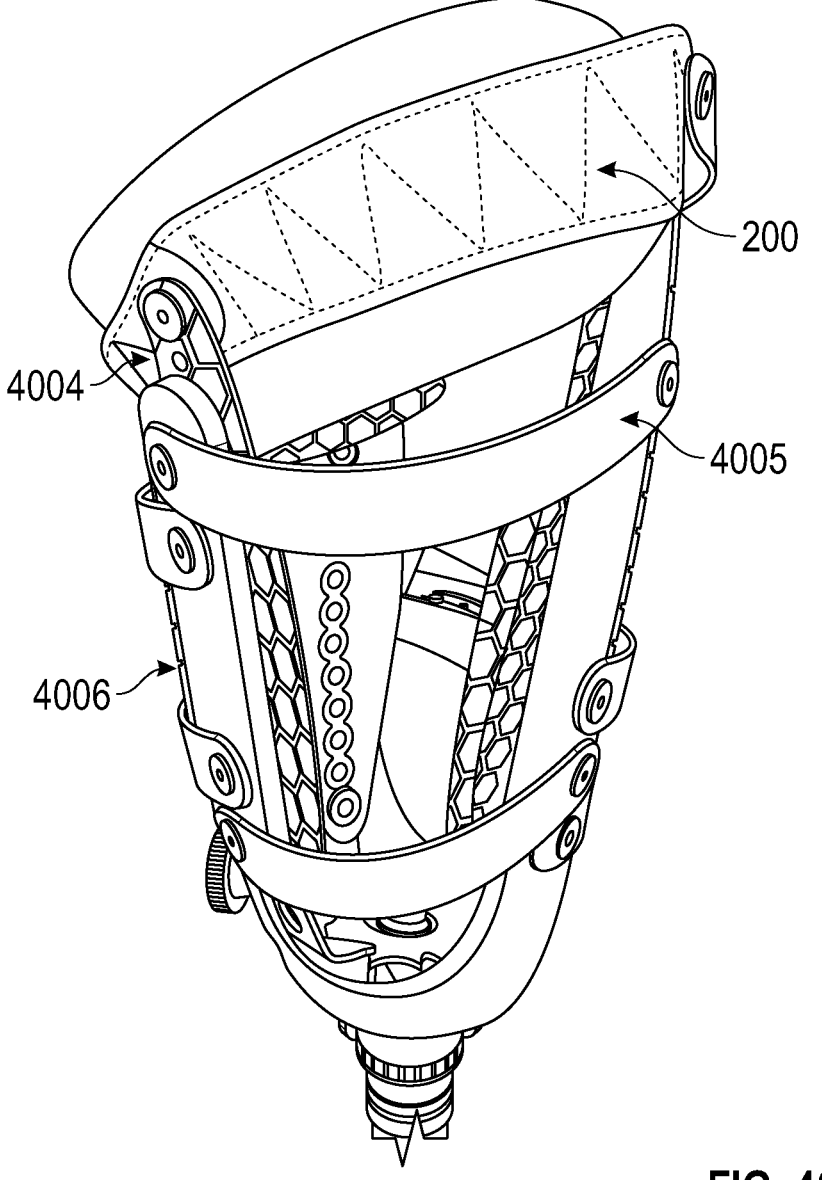

FIG. 40B generally illustrates another preferred embodiment in accordance with the current invention.

Figure 40C:
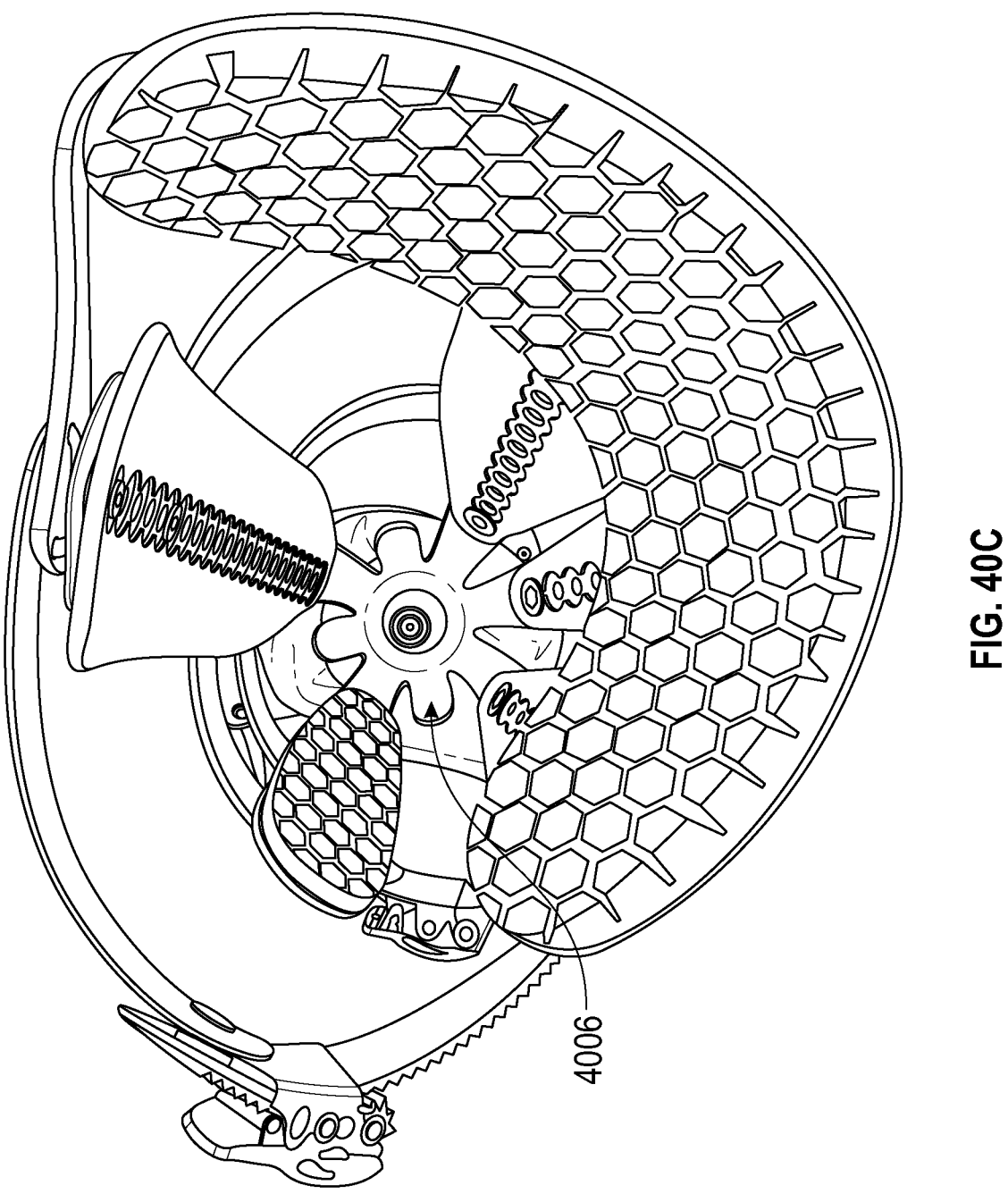

FIG. 40C generally illustrates another preferred embodiment in accordance with the current invention.

DETAILED DESCRIPTION OF THE PREFERRED EMBODIMENTS

Referring now to the drawings, wherein like reference numerals designate corresponding structure throughout the views, and referring in particular to FIG. 1A, numeral 100 generally refers to a new and improved compliant based transfemoral level prosthetic socket apparatus, assembly and/or system, hereinafter referred to generally and collectively as invention 100.

Of note, invention 100 may be generally shown by example in a configuration for an individual missing a right or left leg or portion thereof at a knee disarticulation or transfemoral level. It is understood that such configuration is for example purposes only and that such should not be considered limiting and a left or right side configuration is also considered. It is further understood that invention 100 may be used where the level of amputation may dictate a different configuration than transfemoral or knee disarticulation level, such as but not limited to transtibial, transradial, transhumeral, or other levels either prosthetically, orthotically, or with exoskeletal robotics—all of which may be considered as human/machine connectivity. The terms should not be considered limiting the invention nor the general shape and configuration depicted in the drawings. Invention 100 may encompass many embodiments, as generally illustrated in the various figures, and should not be considered limiting where any particular figure depicts one embodiment of invention 100, as there are various elements, embodiments, and user specific requirements.

In a preferred construction, there may be a distal attachment area or structure 101 for mounting other prosthetic components to, such as but not limited to knees, feet, stubbers, connectors, or other conventionally used components which are used distal to a socket apparatus. The particular attachment means may be any conventionally used means, including plates, screws, gunk, and others.

Extended from the general attachment area 101 may be a stabilizing unit(s) 102. The stabilizing unit 102 may be affixedly connected to the general attachment area, or may utilize elements floating in relation thereto. The particular contouring of the stabilizing unit 102 may be formed in any number of orientations and trim line cutouts, including various widths, heights, contouring, shape, attachment means, and other such elements. The stabilizing unit 102 may extend along any particular side of the limb, including but not limited to along the medial side, lateral side, anterior side, posterior side, or at an angle from one side distally, to a different side proximally.

Figure 5:
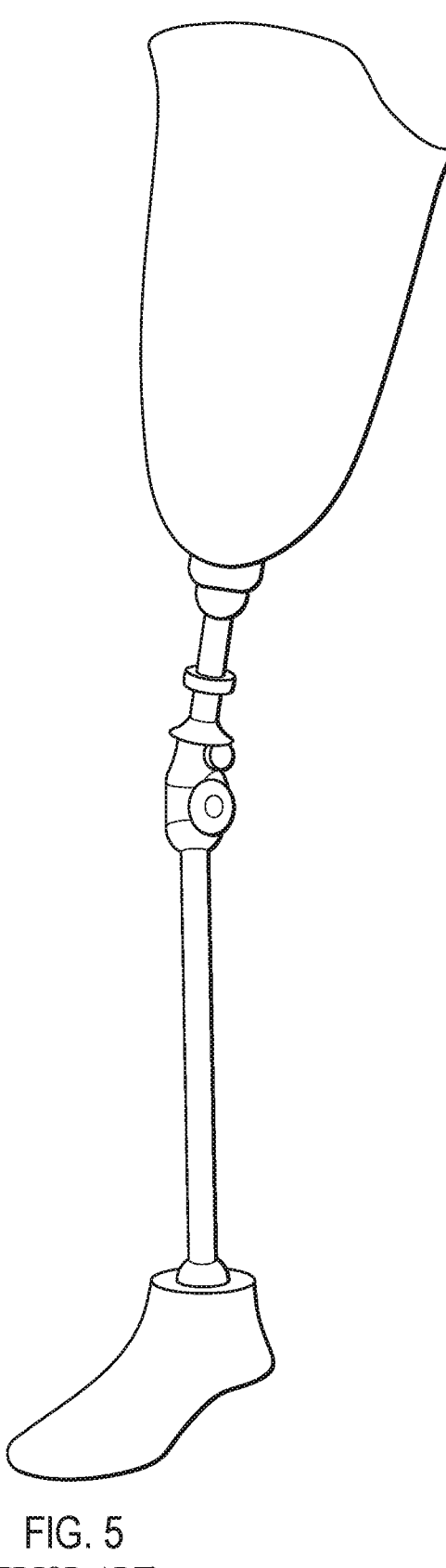

Conventional transfemoral interfaces typically largely circumferentially wrap around the limb, and provide a rigid support under the tuberosity area, as illustrated in FIG. 5. With invention 100 however, in a preferred embodiment, the stabilizing unit 102 may generally extend up the medial aspect of the limb near or between the quadriceps and hamstring muscle groups, or up the lateral aspect of the limb near or between the hamstring muscle group and the quadriceps muscle group, or along the anterior aspect of the limb near or between the hamstrings muscle group and adductor muscle group. The anatomical contouring between those groups may allow for a slight twist to the stabilizing unit 102 as it moves proximally up the limb, as is illustrated in FIG. 1C.

In a preferred embodiment, the stabilizing unit 102 may be relatively rigid to allow for support of the forces imposed through the device. The width of the stabilizing unit 102 may be tailored to individual user's needs, and those illustrated in the figures should not be considered limiting.

In a preferred embodiment, there may be an additional stabilizing unit 102B, which may generally run proximally from the attachment area up the relatively opposing aspect of the limb. Additional stabilizing units may be used, and should not be considered limiting. While this element may not be required to achieve the desired outcomes, it may provide for added stability. In such an example, this stabilizing unit may have a similar rigidity as the medial stabilizing unit 102. Each stabilizing unit may generally contour according to the shape of the underlying limb, or may be relatively generic in shape, contouring to a generic limb. The particular placement, shape, rigidity, number, material, and other characteristics of such a stabilizing unit may be modified on a case-by-case basis according to the particular user's needs.

While the material selection may allow for rigidity of the stabilizing units, because of their inherent shapes they may exhibit somewhat of flexibility in certain directions. To create a solid enough structure for supporting the user through the prosthetic interface, connector means may be used to attach either a stabilizing unit to itself, or to attach two or more stabilizing units to each other. This may be accomplished through using compliant members.

Instead of using an encapsulated socket as in conventional fitting approaches, the invention 100 may use fabric based or compliant based members to encapsulate portions of the limb, or may encapsulate a significant portion of the limb.

Figure 1A:
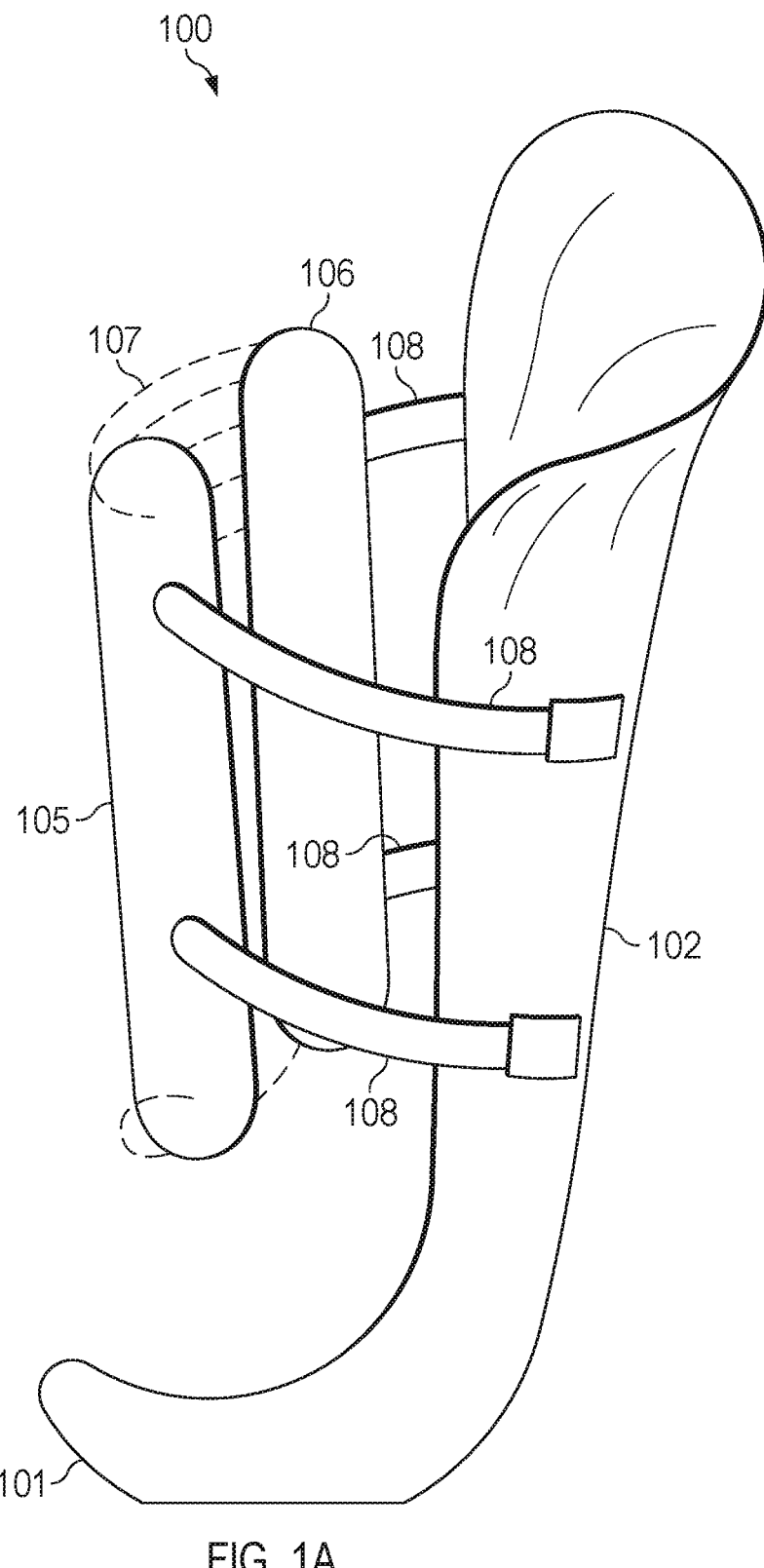

Referring specifically to FIG. 1A, stabilizing unit 102 may generally contour to a limb. In such an example, it may as well incorporate other elements such as padding or foam to help further contour to the specific underlying anatomy of a user. Stabilizing unit 102 may as well incorporate modular elements to modify its height, angle, length, or other adjustable aspects.

In general, stabilizing unit 102 may offer general or specific contouring for the ischial seat toward its proximal end, as in the use-case of it running along the general medial aspect of a transfemoral limb, or may utilize a sub-ischial design. It may as well wrap around the distal aspect of a residual limb, as illustrated in distal area or section 103, whereby a relatively small area is encapsulated to seat the residual limb into. Or, the distal area 103 may offer a larger area where the distal aspect of the residual limb may be encapsulated.

In a preferred embodiment, the predominant amount of force may be taken proximal to the distal end of the limb, and the distal end of the limb may have a relatively small amount of total force, or even no force, as illustrated in FIG. 1A. In such a case, the majority of the loading force through the system may be along the stabilizing unit, proximal to the distal end. Where minimal force may be encapsulated within the distal aspect of the limb, such an area may extend for a portion up the socket interface length, and may resemble the lower portion of a conventional socket interface in shape. Likewise, distal area 103 may extend the full length up the socket interface shape for a flexible inner socket as is traditionally used for such level of amputation, and may be able to be utilized on an existing flexible inner socket interface. Even further, distal area 103 may utilize compliant materials to encapsulate the distal end of the residual limb, thereby hammocking the distal end of the limb in a compliant material, which may include a fabric or other compliant materials.

Figure 1B:
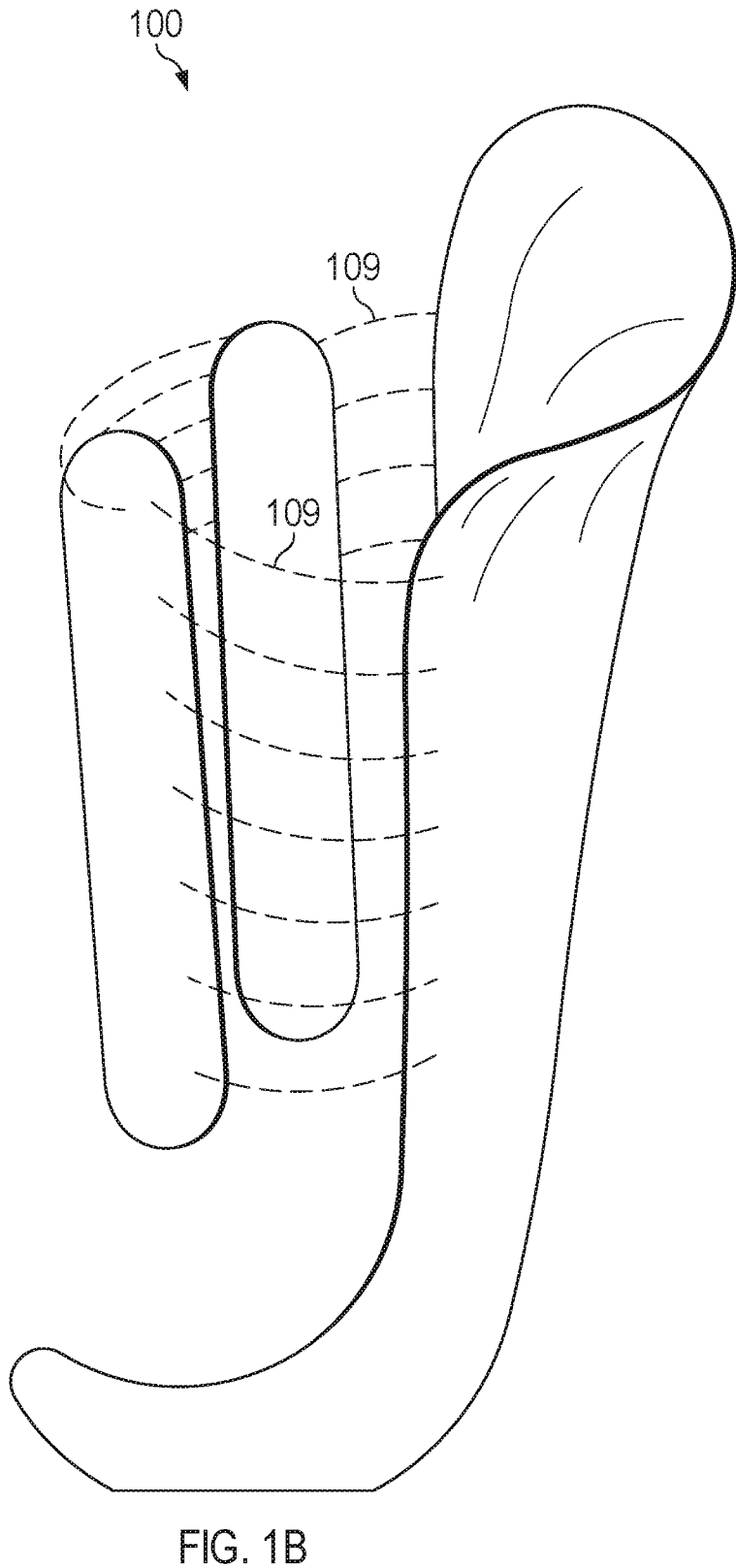
Figure 1C:
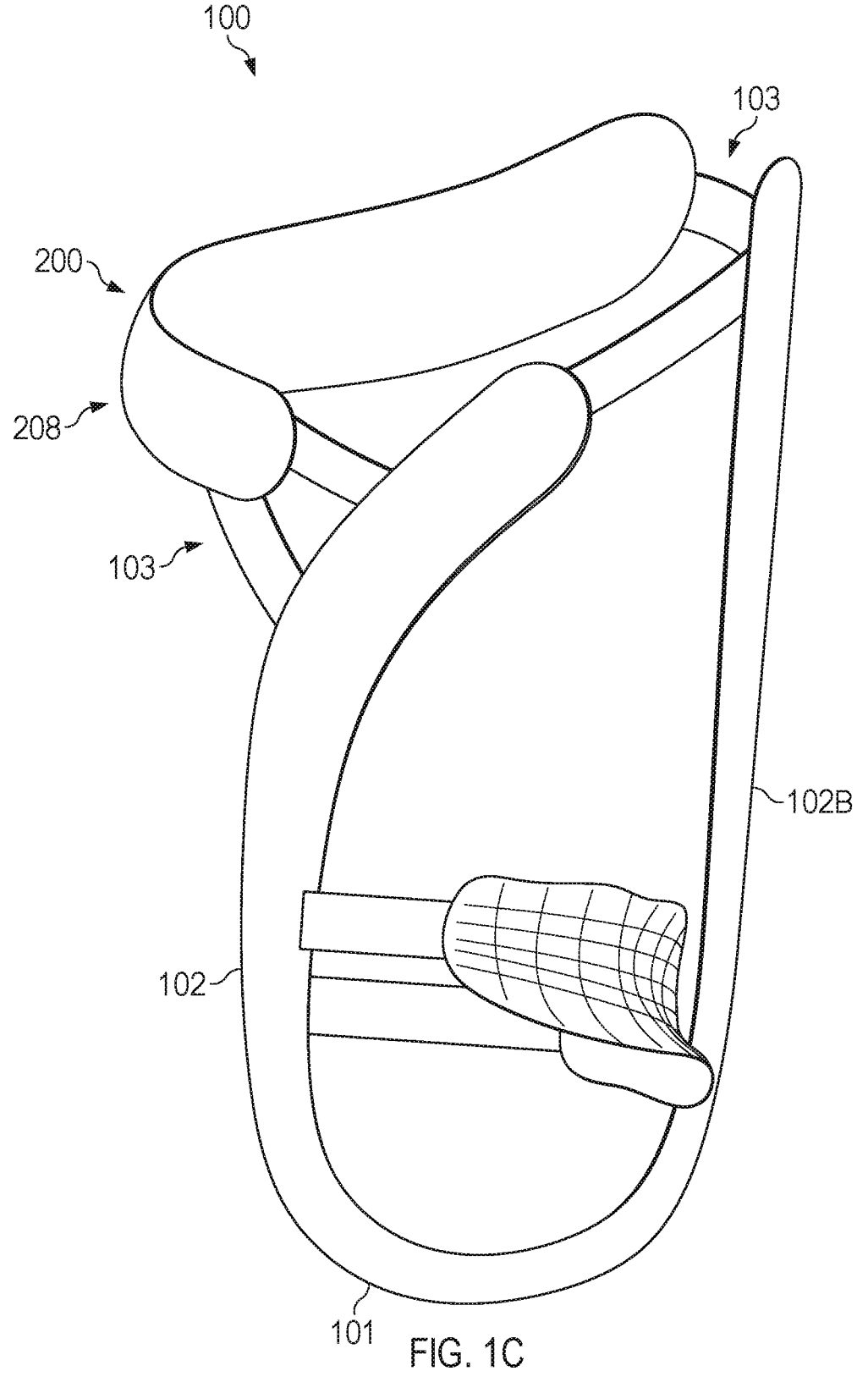
Figure 1D:
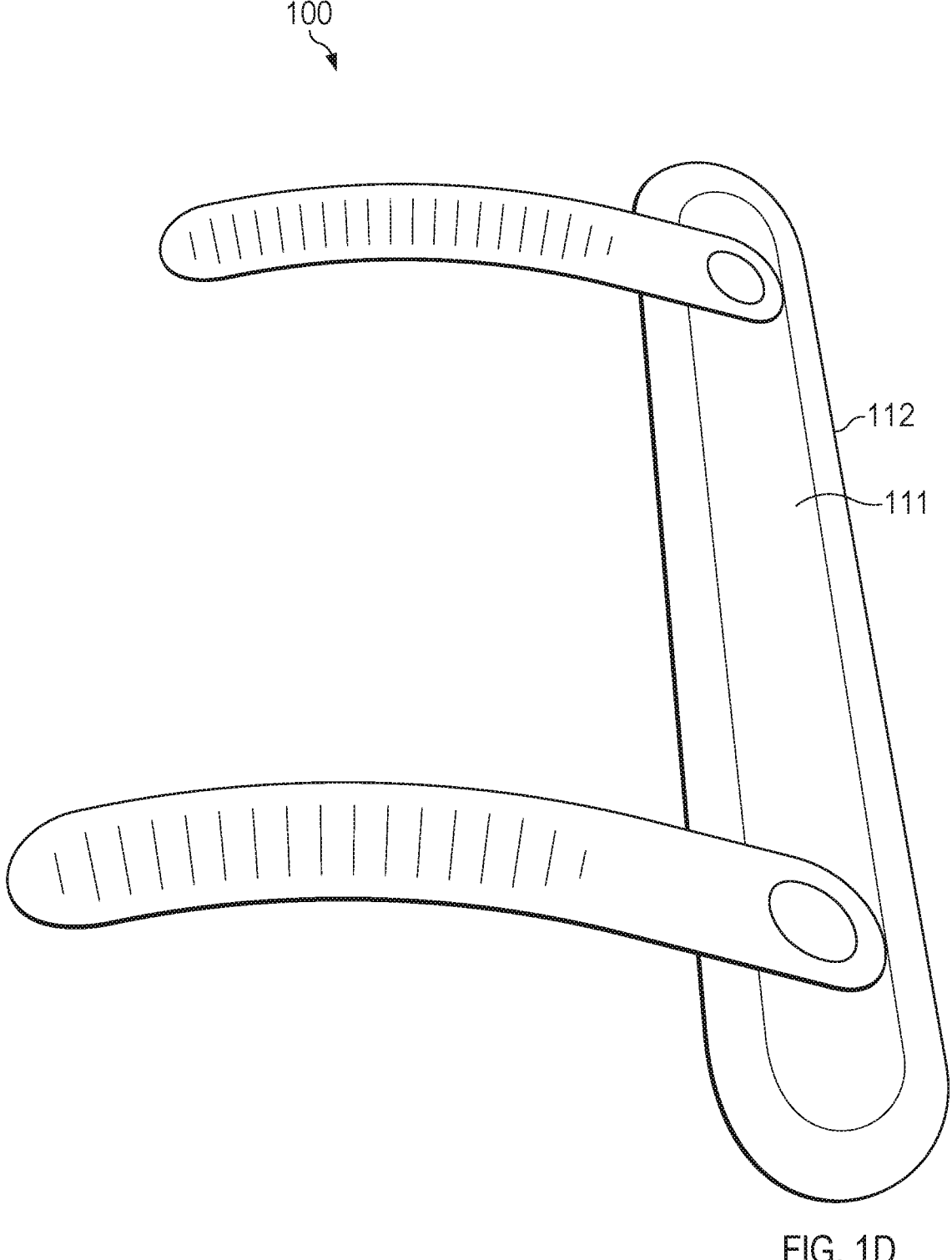
Figure 1E:
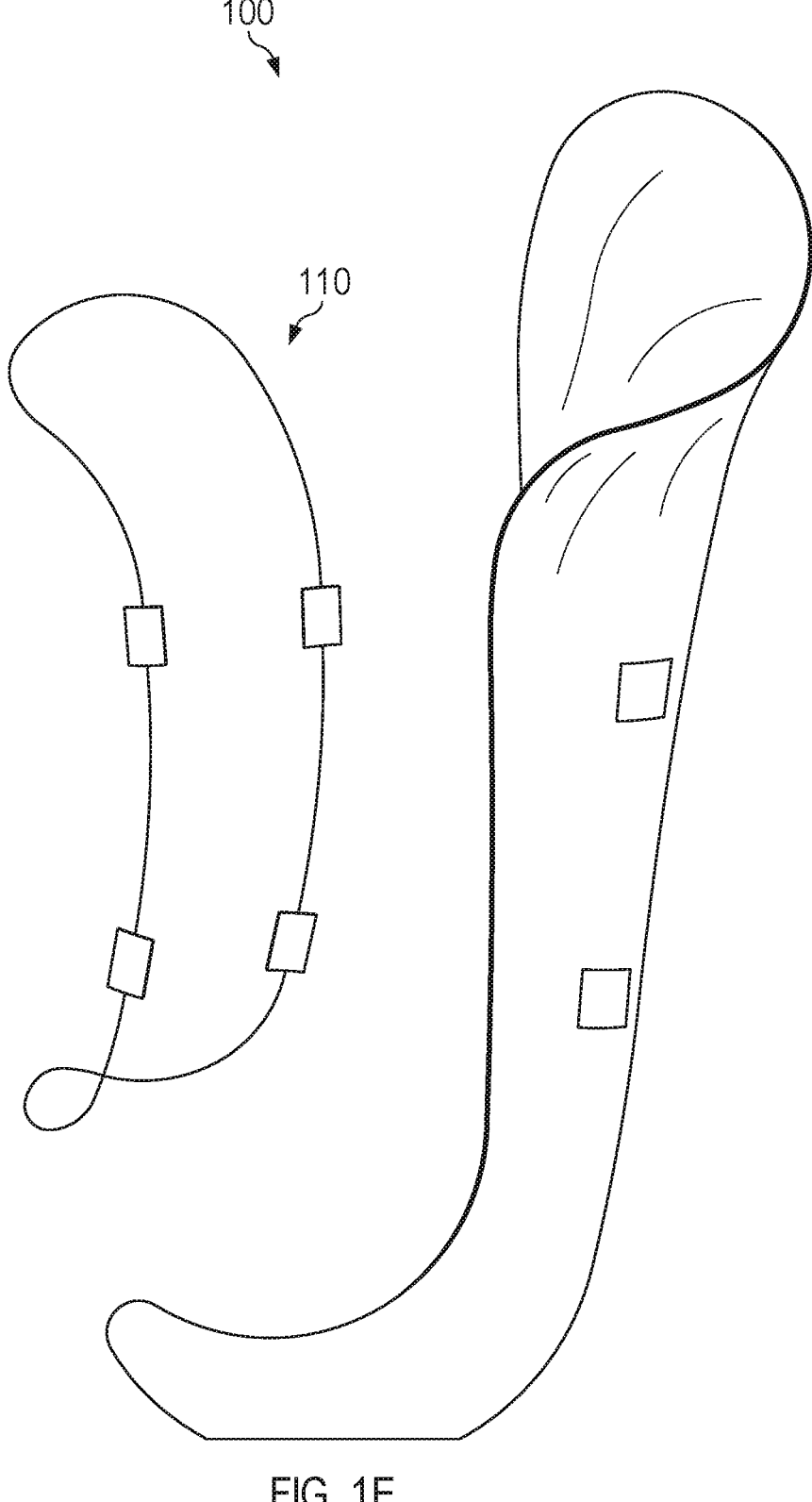
Figure 1F:
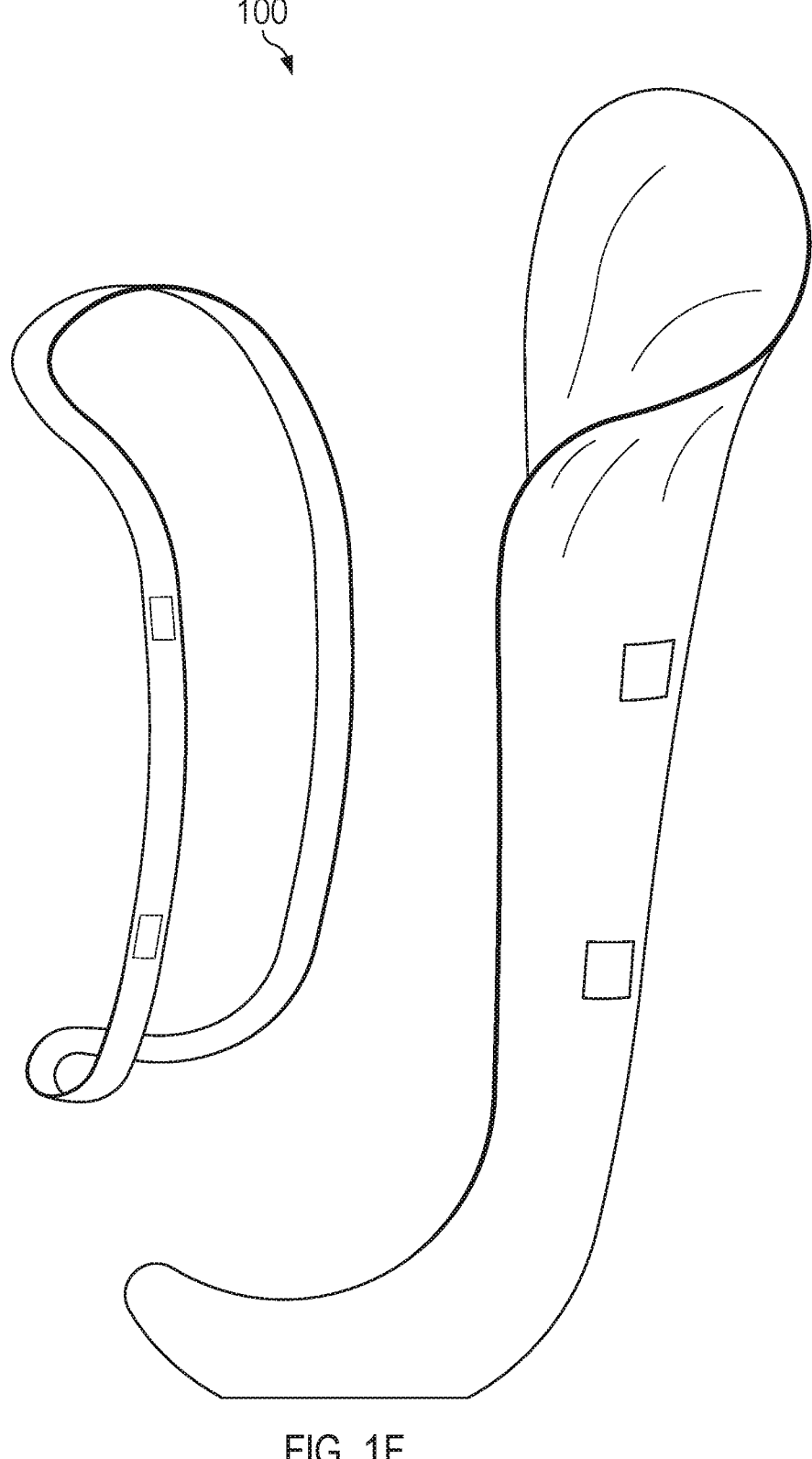
Figure 1G:
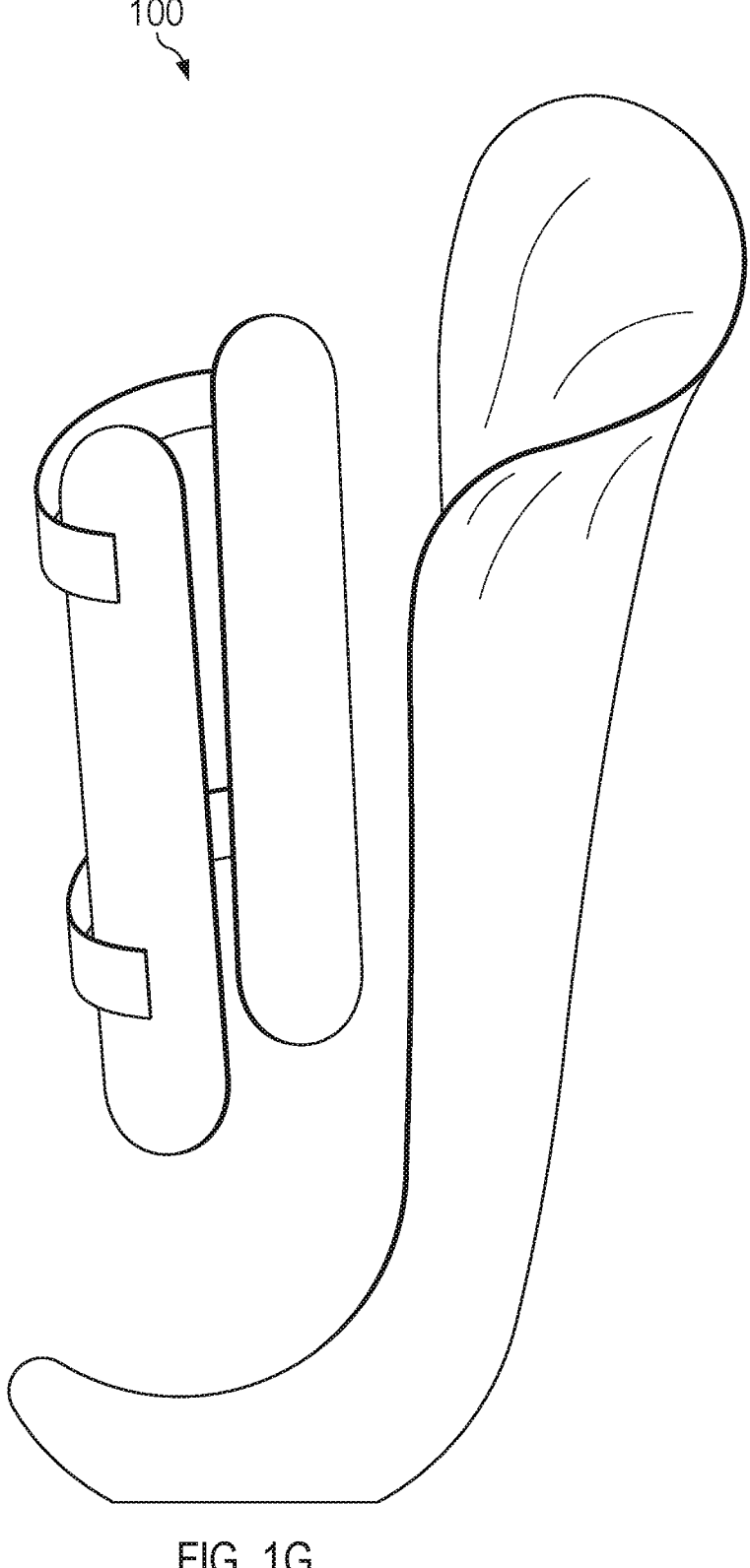
Figure 1H:
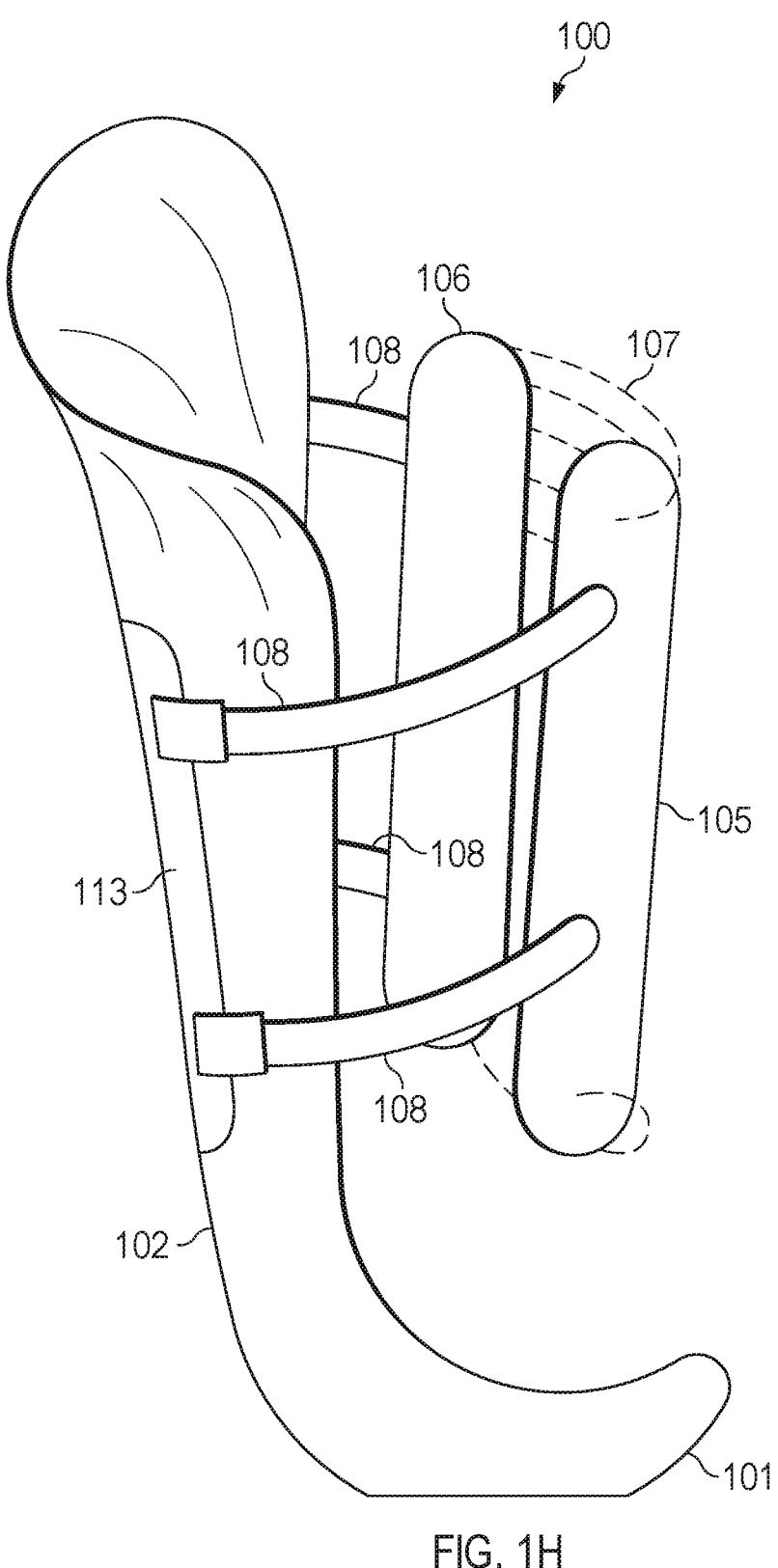
Figure 1I:
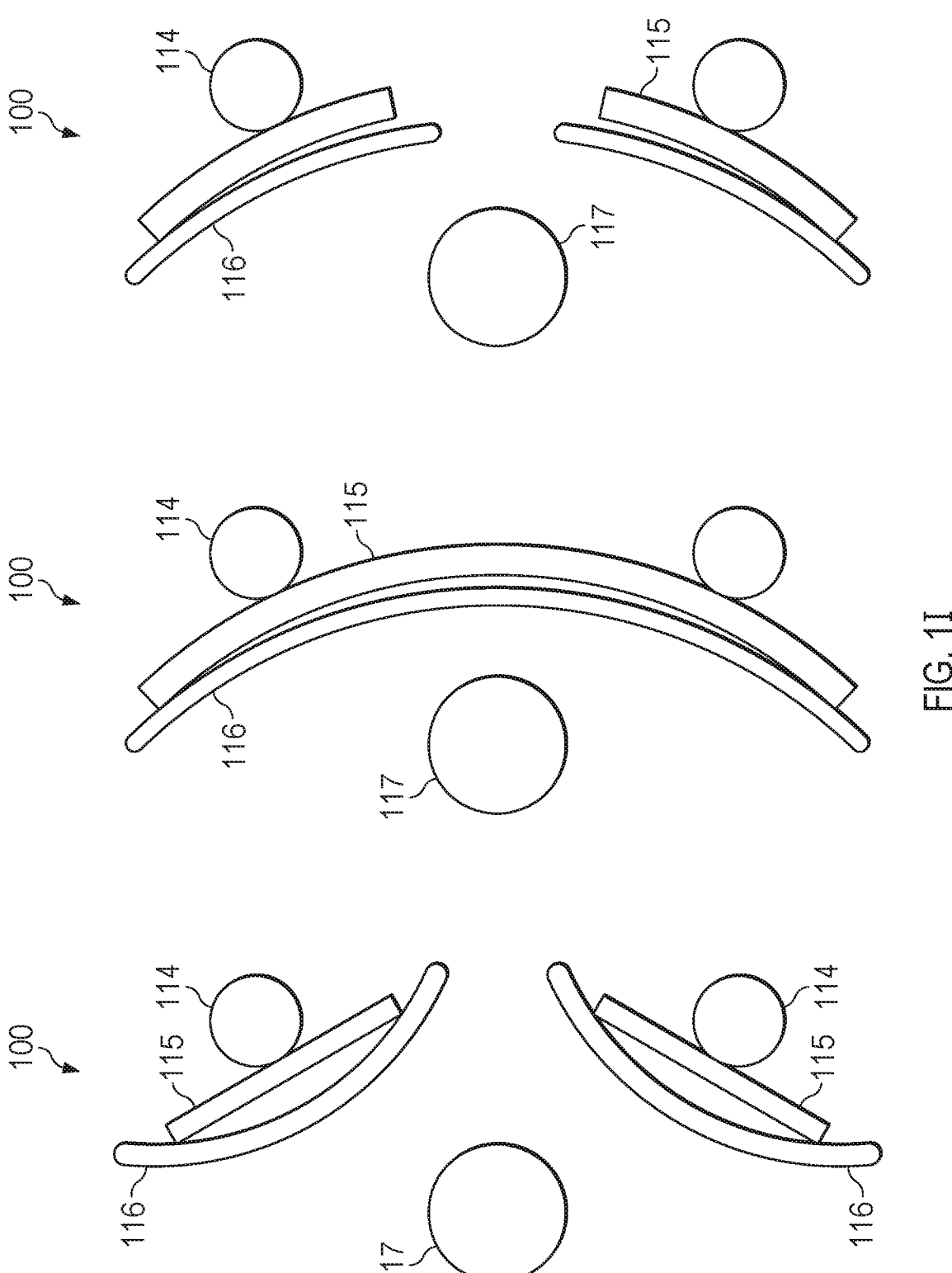

FIG. 1I generally represents various possible cross sections of a proximal top-down view of an embodiment of the stabilizing unit 102, as may be affixed to the medial or lateral aspect of the transfemoral limb for instance. Such stabilizing unit may utilize one or more components of the stabilizing unit to be affixed to the distal attachment area 101, which may be modularly adjustable or not modularly adjustable in angulation, length, or position, or other orientations as may be desirable. Extended from the distal attachment area 101 may be structural elements, which may include tubes 114, poles, struts 115, padding 116, or other such pieces, including any combination thereof, or may be custom fabricated as a single or multiple pieces, any combination of which used individually or together which may have enough structural integrity to support the necessary forces to generally support the user. Such pieces as a unit may help hold orientation about the limb, and may generally contour with respect to long bone 117, generally causing a portion of the stabilizing unit to reside anterior to the long bone (anterior lateral, or anterior medial as the case may be), and one portion of the stabilizing unit to reside posterior to the long bone (posterior lateral, or posterior medial as the case may be). By doing so, the long bone may generally be held in a certain orientation with respect to the stabilizing unit, as the force distribution anchors may be tightened toward it, generally reducing the medial/lateral dimension of the interface. Stabilizing unit may be constructed of at least one independent component(s), with any such various components connected to the distal attachment area independently, and as a total working together as a unit. One example illustrated in FIG. 1I demonstrates the use of two independent components attached to the distal attachment area. Another example illustrates a single component attached to the distal attachment area. And a third illustration demonstrates a hole cut out in a single component, so that the distal end of the long bone may be relieved. Such illustration examples should not be considered limiting, as one or any other number of the examples may be used, or used in combination through the length of the stabilizing unit.

Figure 10:
FIG. 10 illustrates another embodiment of a transfemoral socket interface, viewed from the perspective angle.

Force distribution anchor 105 and 106 may be positioned around the general opposing side of the limb, and may utilize a span of distance between their sub-components. The distance between force distribution anchor components 105 and 106 may be modularly adjustable, and may utilize a compliant material 107 between anchors 105 and 106. The term compliant materials should not be considered limiting and in general may include a range of compliancy. For example, this may include materials such as fabric or mesh fabric, as well as materials like foam padding, fabric straps, VELCRO, or thermoplastic ladder straps for typical ratchet mechanisms—each of which are compliant, and may offer appropriate levels of compliancy for different use-cases. Some use-cases require very flexible compliancy, whereas other use-cases may require a form-factor to be generally held, while still being able to be conforming under load. In general, the term compliant shall signify any material that is conforming to the body under the given load that is imposed on it, and which conforms an appropriate amount for the given use-case. Force distribution anchors 105, 106 may be fabricated of a relatively stiff material, or may be highly compliant. In a preferred embodiment, they may be stiff enough to hold their form with respect to the limb, and may be used as an anchor point for attachment means within the system. The force distribution anchors 105, 106 may be relatively narrow long shapes as illustrated in FIG. 1A or may offer other various shapes, such as but not limited to that which is illustrated in FIG. 10. Their specific shape should not be considered limiting, as they may be a modular component, or may be customized to fit a particular user, who may have particular shape dependent needs. Force distribution anchors 105, 106 may as well utilize markings to help a practitioner determine appropriate trim patterns or hole patterns for modularity. They may also offer spring response, so that during ambulation on the device, they may provide shock absorption for the user.

In another embodiment, the force distribution anchors 105, 106 may be fabricated from flexible materials, such as but not limited to wires, to manage the forces for their intended function.

Attached to the force distribution anchors 105, 106 may be adjustable or non-adjustable connectors 108 that may connect the force distribution anchors to the stabilizing unit. These connectors may allow the force distribution anchors position to be modularly adjustable with respect to the stabilizing unit. There may be any number of connectors, and connector types that may be utilized, and the particular use of connectors in the figures should not be considered limiting. The connectors may even utilize fabric spanned to accomplish the same.

In a preferred embodiment, the connectors may incorporate areas which may maintain a certain curvature shape which may generally resemble the arc around a residual limb, whereas to help prevent the connectors from roping across the limb. In such an example, the connectors may utilize incorporated more rigid elements which may as well provide some spring response during ambulation, or may be rigid enough to not allow spring response. In general, such features may help prevent the connectors from digging into or roping into the limb as they arc around the curvature of the limb. Likewise, a broader material may be used to help spread the load across, thereby preventing them from digging into the limb.

FIG. 1B illustrates such an embodiment, where broad compliant fabric 109 or other compliant materials may be used to connect the force distribution anchors to the stabilizing unit. Such span of compliant material may be attached with any conventional attachment means, and such material may utilize connector means that may be modularly adjustable to allow for ease of tightening to a desired length.

FIG. 1D generally represents an embodiment of a force distribution anchor with connectors attachments on one side, in order to give a representation of how they may integrate within such an element. In such an example, there may be various materials used on within the force distribution anchor to allow for certain areas 111 to be more rigid and certain areas 112 to be more flexible, to allow for an effective tapered transition of forces as it sits around the body. Additionally, as fabric or other compliant materials may be stretched from one stabilizing unit to another, and so forth, the fabric itself may create the soft transition from one structural element to another.

In addition, the connector means, which may be used to connect either force distribution anchors with each other, or force distribution anchors to stabilizing unit, may have semi-rigid elements or customizable elements to provide a set curvature. In doing so, it may help prevent the connector means from roping into the soft tissue as they curve around the limb. Further, the integration of other compliant materials such as fabric to span there between may be used to prevent roping, as it would effectively spread the forces over a broader surface area.

In between the force distribution anchors may be compliant fabric 107, which may or may not be modularly adjustable, to determine the span in between the force distribution anchors. Likewise, a rigid, semi-rigid, or other flexible means may be used to connect the force distribution anchors together, including forming the force distribution anchors together as a single continuous piece with like or dislike materials. It should therefore be understood the force distribution anchors may function as a unit, giving general opposing force to the stabilizing unit, and as such, may be considered a functioning single unit.

FIG. 1E generally represents an embodiment of how compliant fabric, fabric mesh, or other compliant materials may be spanned between a force distribution anchor system of one continuous piece. In such an example of embodiment 1E, the fabric may generally be bridged somewhat similar to a hammock between the force distribution anchor elements. Such assembly may utilize connection means to the stabilizing unit 102, or may use force distribution cabling run through such fabric to create a "paddle" of fabric. The perimeter outline shown in the figure may generally follow what becomes the curvature of the fabric paddle, as the force distribution cabling may be stretched there between in a certain configuration to cause the paddle to represent a pringle-shape, or other shapes may be utilized as well. The force distribution cabling may be complaint, though may cause the structure, which includes the compliant fabric stretched there between, to create a structural unit. Such structure may additionally include attachment means 110 to connect to the stabilizing unit 102. Additional fabric may be spanned between the paddle and the stabilizing unit 102. Additionally, other attachment means may be used to span to connect between as well.

FIG. 1F is similar to FIG. 1E, except that the force distribution anchors may be of a more structural nature formed as a continuous piece, or as a combination of multiple pieces configured to create a structure. FIG. 1E may represent a compliant continuous piece, or combination of pieces. Both examples may utilize fabric or other compliant material spanned in between to further spread out the load across the user's limb.

Still further FIG. 1G may represent an embodiment where the force distribution anchors may be connected together with a semi-rigid strut element, which may alternatively be semi-flexible, which may generally span away from the limb, so that as the force distribution anchors may be pulled toward the main stabilizing unit with their connection means (not shown in the figure), the force distribution anchors may press into the limb tissue. As such, there may also be fabric or other compliant material spanned between the force distribution anchors in addition, all of which may be modularly adjustable in their varying orientations, positions, and general effective contouring about the limb, to modify how they interact with the soft tissue of the limb.

Referring to FIG. 1C, and of which may generally be relevant to and embodied within other embodiments as well, on the proximal end of the interface, invention 100 may utilize a compliant structure to contour around the underlying anatomy, which may generally run from approximately near, at, or posterior to the adductor muscle group region toward the proximal end of the interface connecting at or near the stabilizing unit 102, and run generally around the posterior, or medial/posterior aspect of the limb toward the trochanter area of the lateral aspect of the upper thigh, which may attach to stabilizing unit 102B, or may continue further around the limb back to the adductor region connection point(s). In one embodiment, this element may simply connect the stabilizing unit to the posterior lateral force distribution anchor area, whereas it may generally be positioned near the gluteal fold region, to provide at least one of contouring, comfort, and control of the device.

FIG. 1H generally represents an embodiment where stabilizing unit 102 may generally extend from distal attachment area 101 proximally up the general lateral aspect of the limb, and whereas the force distribution anchor 105, 106 may generally extend across the medial aspect of the limb. As such, the anterior force distribution anchor may generally sit near or between the quadriceps muscle group and the adductor muscle group, while the posterior force distribution anchor may generally sit near or between the adductor muscle group and the hamstring muscle group. In such an embodiment, the femur may generally be pulled laterally toward the stabilizing unit, and such stabilizing unit may exhibit a general angulation similar to the desired femoral angle.

Embodiment 1H may generally utilize a load bearing compliant member or structure 200, which the user may rest into during load bearing. Such unit may be incorporated within the force distribution anchor assembly or may be independent from such. By being compliant, such unit may provide increased comfort for the user, versus the traditional rigid ischial/ramus/tuberosity shelf found in conventional transfemoral sockets. As such, this element may function somewhat similar to the medial/posterior aspect of a rock climbing harness, in that some of the weight bearing of the unit may be bore in soft compliant materials, versus rigid structures. The lateral orientation of the stabilizing unit may allow the compliant member 200 generally be supported in the correct orientation with respect to the body.

This compliant member 200 may be utilized with stabilizing unit alone, or may incorporate force distribution anchors to assist in managing the direction and orientation of the forces through the system. It has been found clinically that the integration of the force distribution anchors within such an embodiment may provide added control and comfort.

In such an embodiment, the stabilizing unit extended up the general lateral aspect of the limb generally may make it more conducive for more of a generic shape to fit to a wide variety of limbs, versus having to be custom fabricated.

In an embodiment where stabilizing unit may extend up the lateral aspect of the limb, an opening 113 may exist in such stabilizing unit to allow for the long bone and/or tissue surrounding the long bone to fit within. As such, the distal end of the long bone may have space to press into a space where there is no rigid structure. This space may be spanned with no material, or may be spanned with compliant fabric to further control tissue flow. It is understood that such opening may be in any width, height, contouring, or shape as may be best suited for the particular patient, or for human anatomy as well. Stabilizing unit may exist in various subcomponents to allow for such opening to be created, including but not limited to disconnected anterior and posterior support sections, each of which may be connected to a distal and/or proximal end together, or to other such structure, including structure 101. Such opening may also be used where the stabilizing unit resides along the medial aspect of the limb.

In general the term medial and lateral are in particular reference to a transfemoral use-case, and for other use-cases such as transtibial, transradial, transhumeral, or for orthotic applications, the particular orientation of the compression may best be utilized in an orientation other than medial/lateral, such as but not limited to anterior/posterior, and as such the general terminology should not be considered limiting, as the terms medial/lateral for the stabilizing unit and force distribution anchors general opposing force directions are for example purposes only for the transfemoral use-case, to allow one skilled in the art to better comprehend how they may relate with one another.

Amongst FIGS. 1A-1I general embodiments, force distribution anchors may generally float with respect to the stabilizing unit 102. By doing such, their circumferential position about the limb may be modularly controlled, allowing for full accommodation to the user's limb size and shape. Furthermore, if two force distribution anchor components are joined together as one unit, they may be positioned on either side of the long bone of the limb segment, allowing the more compliant material spanning in between, which may also be an area without material spanned in between, to be positioned over the long bone. By doing such, the force distribution anchors may effectively help lock the bone position such that the long bone is generally controlled during ambulation, through using the device. The compliant material, which may span between the force distribution anchors may allow for the sensitive distal end of such bone to be free of contact with any rigid or semi-rigid surface. One component of the force distribution anchor may generally reside on the anterior side of the long bone (anterior/medial, or anterior/lateral depending on orientation of the stabilizing unit being laterally or medially orientated), and one component of the force distribution anchor may generally reside on the posterior side of the long bone (posterior/medial, or posterior/lateral depending on the orientation of the stabilizing unit being laterally or medially oriented).

As the force distribution anchors may be tightened toward the stabilizing unit 102, it may generally shorten the medial/lateral dimension of the interface, as in the case of using this on a user with a transfemoral amputation for instance. In such a case, the long bone may be generally pulled toward the stabilizing unit, and maintained in such a position, as is referenced in FIG. 7 with the desired femoral angle. To accomplish this, the limb tissue may need to be displaced, in which the anterior and posterior dimensions may allow for the material to be displaced into, so that the medial/lateral aspect of the interface can be tightened to control the bone. The force distribution anchors may work in coordination with one another as effectively one unit locking the femur from the anterior and posterior sides, along with any material that may connect between the two, to control the position of the long bone.

It should be understood that while the invention is described in these configurations. Further, embodiments from FIGS. 1A-1I may be utilized on other levels including transhumeral, transradial, and transtibial levels with similar advantages as for a transfemoral level. Still further, embodiments illustrated in FIGS. 1A-1I may also be utilized in similar orthotics and exoskeletal robotics levels to control the underlying limb segments. The shapes of the stabilizing unit and force distribution anchors may embody many various configurations, and those illustrated and discussed should not be considered limiting. The general principles of how such pieces may connect together, and how the pieces may work together to control the limb can be accomplished with a variety of configurations.

Referring to horizontal section or attachment means 208 as illustrated in FIG. 1C, the compliant structure 200 may generally be used to support load bearing of the user within the device. This element may be utilized in any of the embodiments, and generally may be spanned near or as the proximal posterior connector, running along the gluteal fold region. Instead of solely supporting the user's weight volumetrically through the whole limb as in conventional devices, a sizable amount of the vertical loading may be bore through such compliant member, and specifically it may run near the gluteal fold region to help accomplish the soft tissue and anatomical contouring as loading. Through using it in the configuration where it may extend further under the medial aspect of the limb as well, it may utilize ischial loading as well. This may function similar to how a rock climbing harness suspends its user, though may be accomplished here for use in prosthetics interfaces. This compliant member may further extend to or past the ischial area, so that such area may be supported by a compliant member, similar to how a rock climbing harness may function, instead of using a rigid or semi-rigid seat as in conventional socket interface designs.

Figure 2A:
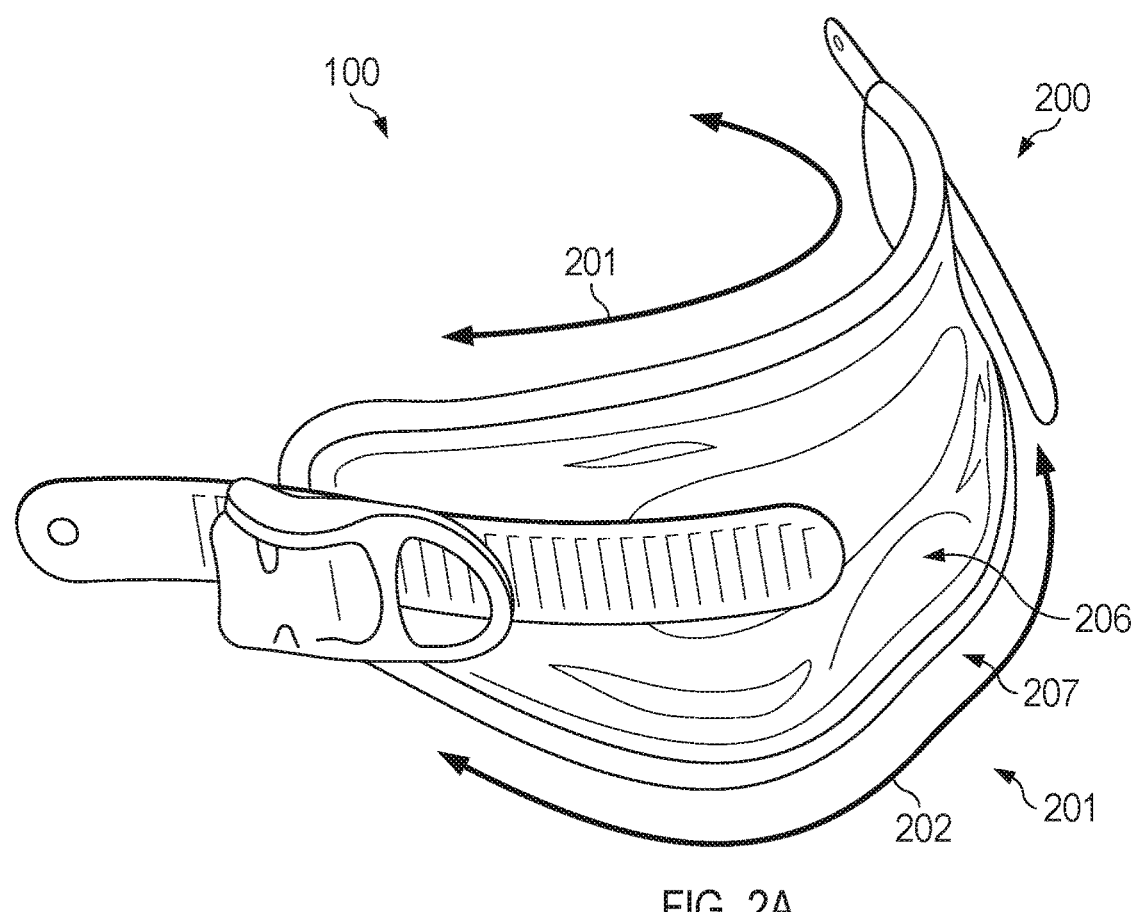
Figure 2B:
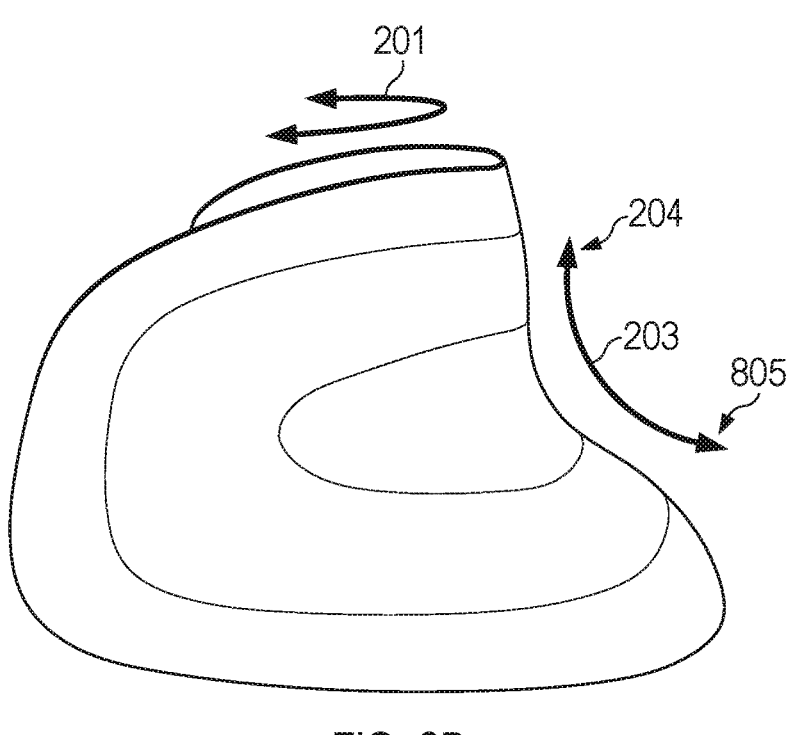

FIGS. 2A-2B generally show a preferred embodiment of such compliant structure 200, here specifically depicted as a gluteal stabilizer. The structure may encompass adjustable attachment means on its medial and lateral sides. These attachment means may be any commonly used in the industry, and those depicted should not be considered limiting, but may include user adjustable means, or non-user adjustable means, or a combination of both. The compliant nature of the compliant structure itself should, in a preferred embodiment, lend itself to a formed shape, while maintaining compliancy.

The attachment means may allow for adjustability in fit through tightening or loosening the compliant structure, changing the circumferential dimension of the interface. It may also be used to connect the stabilizing unit(s), which may provide added structural support of the interface unit.

It may encompass various materials of various degrees of compliancy to maintain such, including but not limited to fabric, foam, plastic, or other generally compliant materials.

In general, the compliant structure may conform around or near the gluteal fold area of the body on the posterior side of the body. It may also offer a level of arc or concavity 203, which may help to contour into the soft tissue between the hamstrings and the buttocks.

The compliant structure 200, in a preferred embodiment, may have asymmetrical contouring as depicted in curvature or section 201 versus curvature or section 202, and curvature or section 204 versus curvature or section 205. In such an example, the curvature or section 201 may be notably different than that of curvature or section 202 to contour over various users differently. Some users may benefit from curvature or section 202 positioned on the distal aspect of the structure. Conversely, other users may benefit from the unit being positioned 180 degrees, with the curvature or section 201 positioned on the distal aspect of the strap. Having a reversible design may allow for better user contouring and success.

Likewise, asymmetrical contouring of arc 203 may benefit various users. Positioning the unit with the broader curvature of section 205 on its distal aspect may benefit those patients with larger soft tissue areas, which positioning the unit such that section 205 is positioned on its proximal side may benefit users with other body shapes.

The compliant materials of invention 100 may as well benefit from accessory elements such as integrated nanotechnology or other technologies to provide various characteristics that benefit the functional or user performance or experience with the device. These may include, but are not limited to, sensors, hygiene elements, antimicrobial elements, water repellency, or others.

This structure may as well integrate in purposed contouring to fit around the tuberosity and ramus areas of the body. This area may offer differing degrees of conformity or rigidity, in order to provide the necessary support for the user's needs.

There may be a generally similar compliant structure connecting the medial stabilizing unit 102 to lateral stabilizing unit 102B, as well as others as integrated. This may be used to help provide added structural stability of the interface unit, as well as provide sufficient comfort for the user on the proximal anterior aspect of the interface.

Figure 3:
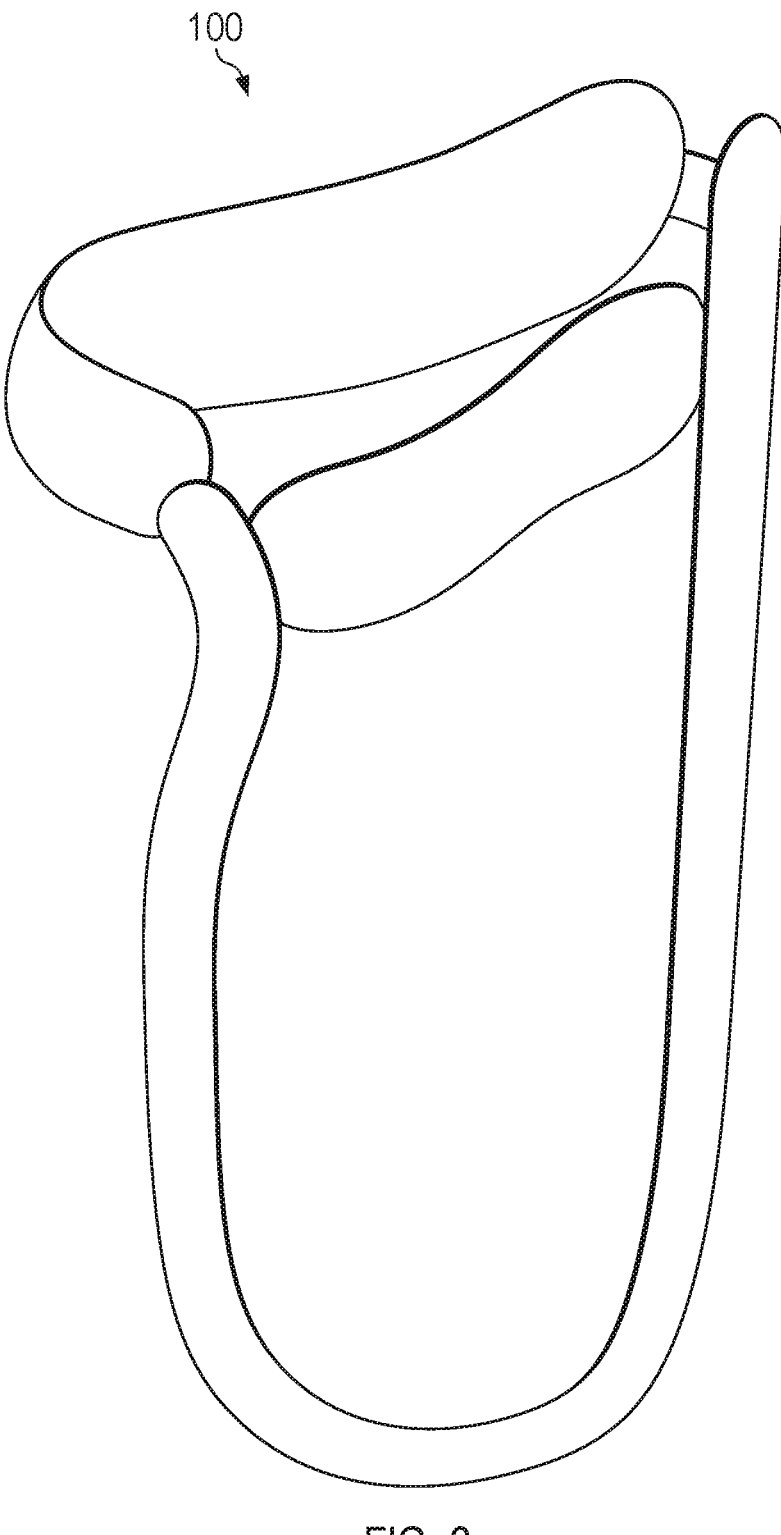

FIG. 3 generally illustrates an alternative embodiment of the invention 100 where the medial stabilizing unit may generally contour up the medial aspect of the limb, and may further contour around or near the tuberosity area, providing support through the stabilizing unit 102, versus directly through the compliant structure 200. There may also be another connector means running along the anterior connecting the various stabilizing units. Additional compliant material may be spanned in between across and around the general circumference of the limb, to help control tissue and connect to the stabilizing unit(s).

Figure 4A:
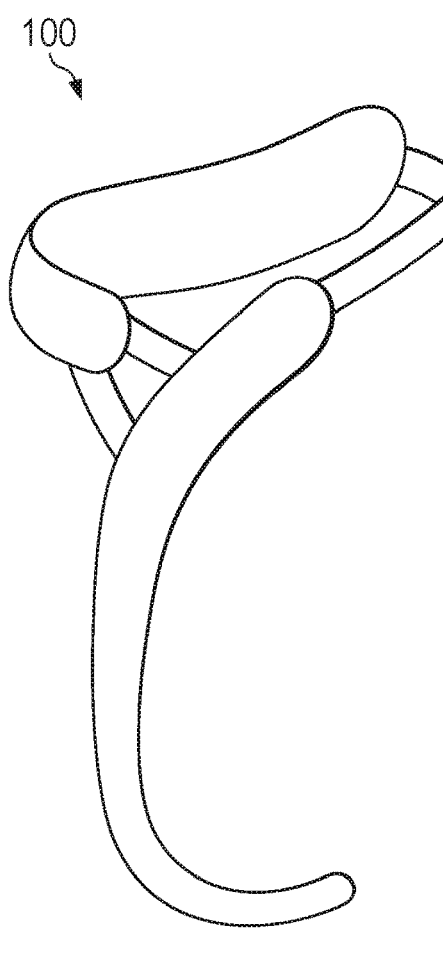
Figure 4B:
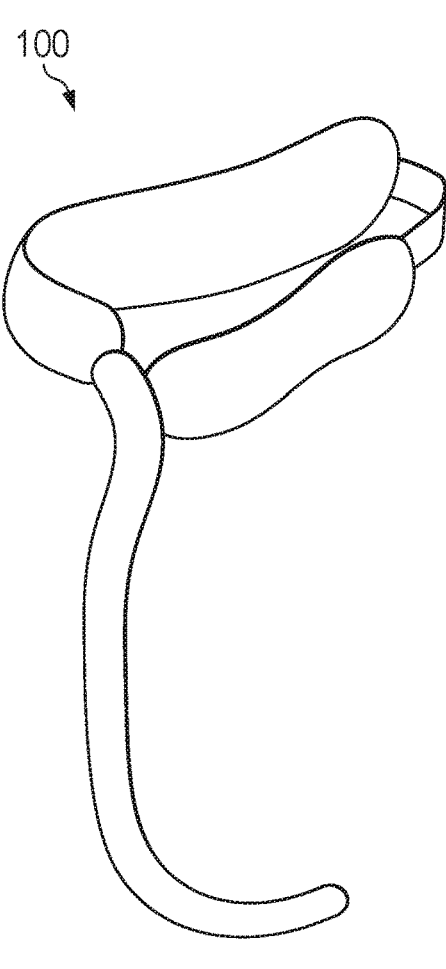

FIG. 4A and FIG. 4B generally illustrate similar configurations as shown in FIG. 1A and FIG. 3, although utilizing just medial stabilizing unit 102, versus in combination with a lateral or other numbers of stabilizing units. In such an example, other compliant members may additionally be integrated to prevent user movement within the device in certain orientations of movements. One such example of such may be to connect the proximal lateral aspect of the proximal circumferential unit as show, to the distal lateral aspect of the anchor stabilizing unit to prevent the circumferential unit from migrating proximally. This can be controlled with a compliant strap, versus a rigid element. Further areas of the open areas may be spanned with other compliant materials, including but not limited to compliant fabric mesh. These other materials may be used to provide control of the tissue of the limb. The use of such circumferentially spanned fabric may help to encapsulate and control the limb tissue through stretching it tighter or looser in certain areas and directions about the soft tissue. The illustrations in FIG. 4 may as well utilize force distribution anchors as illustrated in other embodiments as well. These are not shown in this figure for simplification purposes, and therefore should not be considered limiting.

FIG. 6A generally illustrates the integration of a femoral stabilizer unit 600 integrated within the invention 100. In such an example, the general dynamic characteristics of the femoral stabilizer unit may be similar to the compliant structure 200, though may contour specifically around and proximal to the distal aspect of the femur bone. Its contouring may generally utilize 3-dimensional contouring sections to best contour around the underlying anatomy. It may offer lowered sections or attachment means 208A and 208B to post either side of the femur bone, and a raised section 209 in between to allow the actual distal femur to not be impinged.

Adjustable connectors 210 may be used to allow for user adjustable tightening of the femoral stabilizer. The purpose of such a compliant structure may be used to not only post the sensitive distal aspect of the femur from the interface, but just as importantly, may help maintain femoral stability and femoral angle, thereby providing for a greater biomechanical stability of the femur within the interface. This will lead to greater control and stability for the user, as their bony structure within the residual limb will be more closely locked to the prosthetic movement. Such a femoral stabilizing unit may be used independently from, or in combination with force distribution anchor structure.

This femoral stabilizing unit structure may be attached at more than one location on each side, and may utilize other attachment sections (not shown in the figures) to provide increased positional stability of the unit with respect to the user's limb orientation. It should be understood that the illustration described in FIGS. 6A-6B may be functionally similar to that described in FIGS. 1A-1I, whereas the long bone may be more advantageously controlled by a connected, yet floating, element, which may contour around the long bone in a way as to control its movement within the device.

Figure 7:
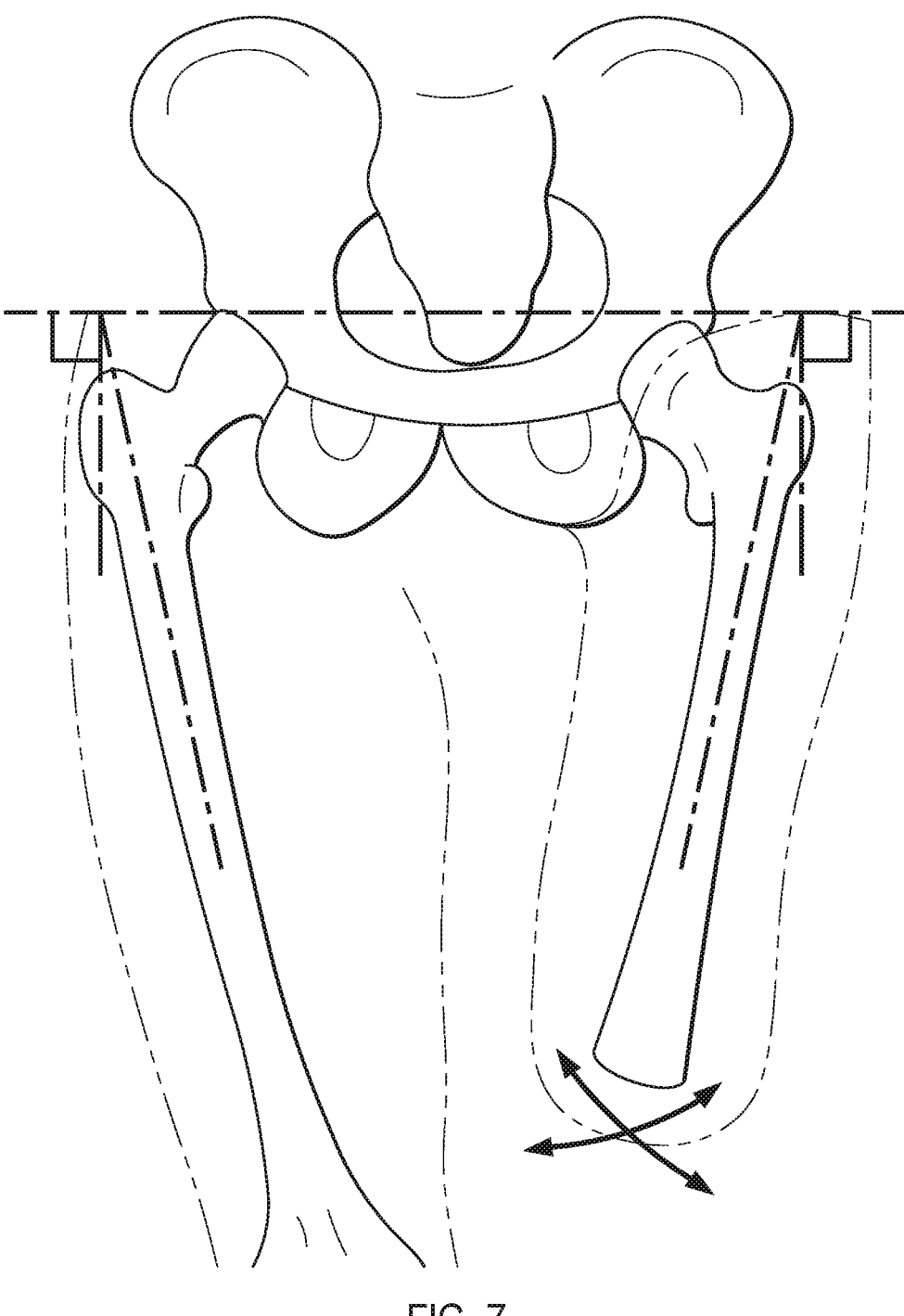
FIG. 7 illustrates the human anatomy and the desired femoral angle in particular.

Such an element may help maintain femoral stability within the design. FIG. 7 illustrates the femoral angle that should be maintained within a socket interface device. However, due to the cut end of the femur bone not being connected to the rest of the limb, the femur tends to move anterior/posterior, as well as medial/lateral during walking. This movement decreases stability and gait efficiency.

Figure 8:
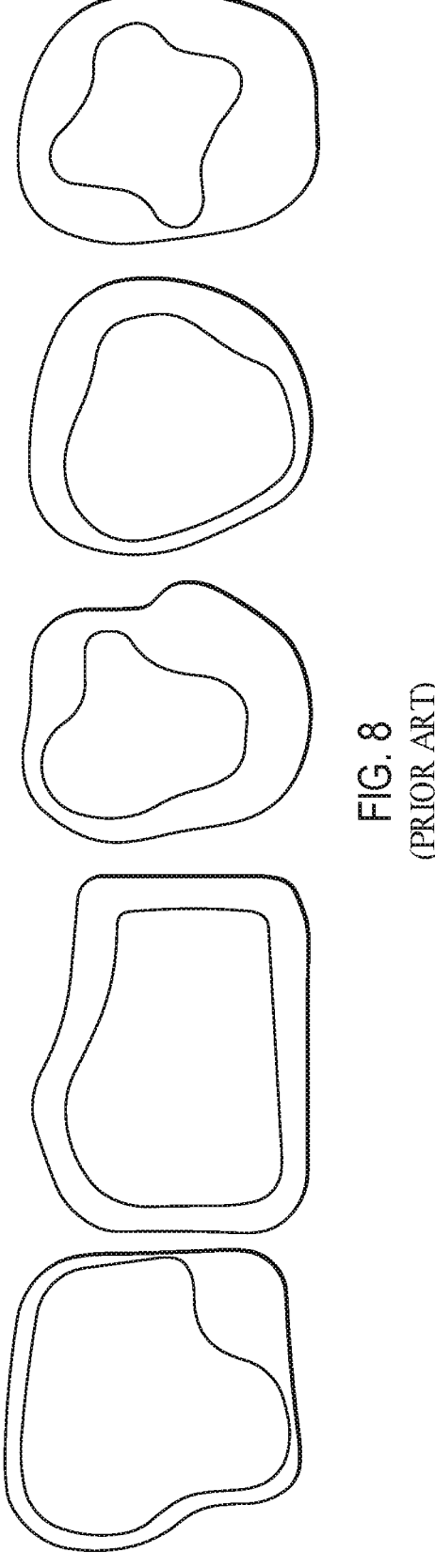
FIG. 8 illustrates various embodiments of prior art showing the evolution of transfemoral socket interface designs.

FIG. 8 demonstrates several of the evolutionary iterations of transfemoral socket design that have been used to help maintain femoral stability, as well as comfort and provide control of the limb. From left to right, these include: Plug fit socket, quad socket, Sabolich socket, MAS socket, Hi-Fi socket. Besides the Hi-Fi, each uses a hydrostatic fit, and all versions rely on enclosing the limb within an encapsulated thermoplastic socket, and none provide volume accommodation. Of these, only the Hi-Fi socket does an adequate job controlling the femur within the soft tissue. As one can see, the same anatomy of the human thigh can fit within many different shapes, and all of which may allow a user to effectively walk on their prosthetic device. This large variety of fitting methods is somewhat due to the compliant nature of the soft tissue of the thigh; however, each design offers different degrees of comfort and bony control. This may also suggest that the stabilizing unit as generally illustrated in FIG. 1 and others may be an off-the-shelf shape, which may be somewhat customizable to the user either through adjustment means or compliant materials incorporated within such as padding, to allow for a conforming and comfortable fit.

Figure 9:
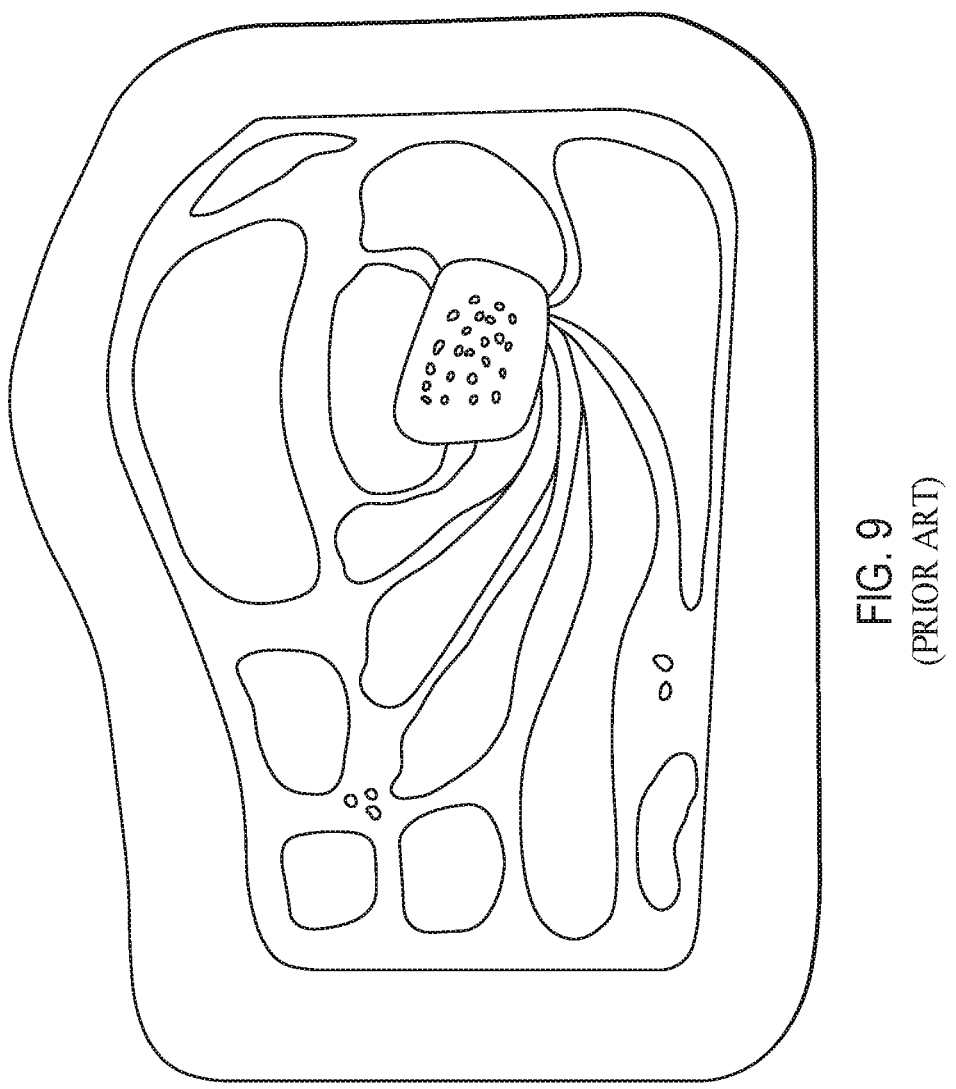
FIG. 9 illustrates the human anatomy as it fits within one embodiment of conventional prior art socket interface designs.

FIG. 9 generally shows how the muscles and bone fit within one version of a conventional socket design, in this case, showing an antiquated quad socket.

FIG. 10 shows an embodiment of invention 100 wherein the femoral stabilizing unit may be integrated within a vertical oriented force distribution anchor unit. Additionally, it may be integrated within a stabilizing unit or may be generally floating and connected to a main stabilizing unit via connectors. In such an example, there may be a main medial stabilizing unit, connected to floating anterior and/or lateral force distribution anchors. There may also be other numbers or locations, or contouring of such stabilizing units and force distribution anchors, and the illustrations should not be considered limiting.

In between the various force distribution anchors and stabilizing unit sections within the various embodiments may be a compliant fabric, which may include, but not limited to a mesh material. Such a material may offer breathability, coolness, lightweight, and durable design. In such an example, it may help encapsulate the limb tissue, providing for increased comfort and control. Even further, such compliant material may help post the distal femur and may allow the distal femur to contact only compliant fabric, versus rigid structure.

Figure 11:
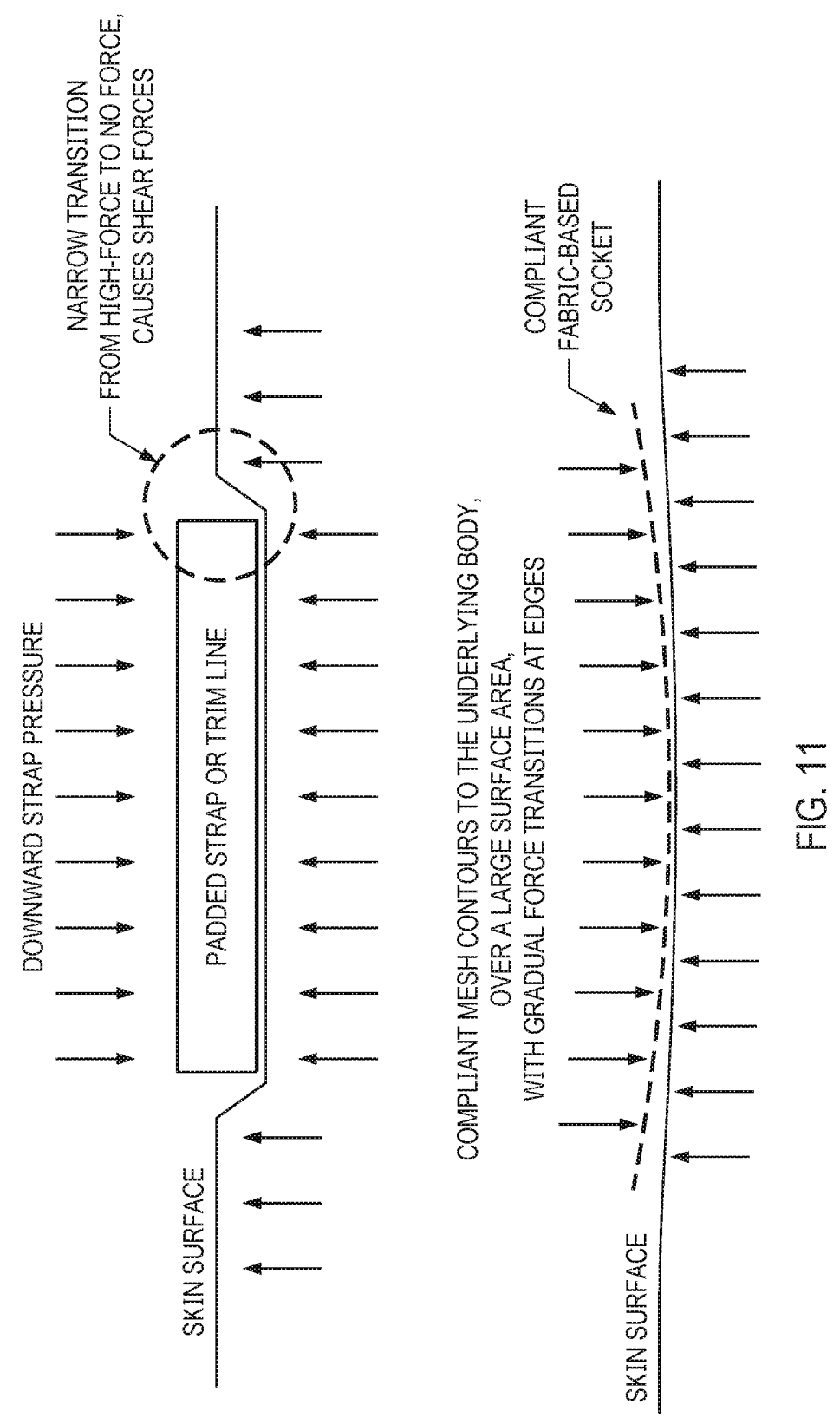
FIG. 11 illustrates the benefits of distributing forces through using compliant materials.

FIG. 11 demonstrates the benefit of integrating compliant fabric within the interface design, as it allows for a gradual transition from high forces to no forces. The fabric is not specifically illustrated in the figures for simplicity, though would reside between the various stabilizing elements, as may be integrated within the compliant fabric-based socket element. As a fabric may extend from a stabilizing element, the underlying tissue may be controlled at the transition points, allowing for gradual transitions of pressures, versus typical sharp transitions as is typically found in conventional fitting methods.

In addition to the socket contouring as depicted in the various illustrations, there may as well be a distal cup or distal socket area, which the limb may reside (not shown in some of the illustrations). This may allow for any portion (from partial to full) of the limb to be encapsulated, allowing for suction or vacuum suspension to be achieved. This element may be fabricated with conventionally known methods and/or materials. Still further, the user may use a gel liner or other compressive sock or the like in conjunction with invention 100, which may allow for suspension, and tissue encapsulation and control as desired. The gel liner for example may be used independently or in conjunction with other flexible inner socket elements.

Invention 100 may be used in coordination with an existing socket design, or with a conventional flexible inner socket integrated, such that the force distribution anchor assembly may advantageously be used to improve the fit of an existing socket, as well as minimize the complexity of fitting a conventional socket, as invention 100 may help to improve modularity and adjustability of the fit around a user.

The compliant force distribution socket may encapsulate the limb with compliant materials, such as but not limited to fabric mesh, and may eliminate the non-breathable hot and heavy thermoplastic socket. It may utilize isolated regions of compliant, yet stabilizing zones, and a broad distribution of forces to support the limb and minimize point pressures.

Each may be connected with adjustable connectors to allow the user to tension the tightness to a preferred comfort. The stabilizing unit segments and the compliant fabric may be adjustable-allowing for the clinical fitting process to be modularly customizable to the user, as well as user-adjustable for preferred security and comfort.

The medially oriented stabilizing unit may key into the soft limb tissue generally near or between the hamstrings and adductor muscle groups, and a lateral oriented stabilizing unit may generally position near or between the hamstrings and quadriceps muscle groups, and an anterior stabilizing unit may generally position near or between the quadriceps and the adductor muscle groups. The various stabilizing units along with opposing force distribution anchors together may provide opposing forces, locking the limb in relation to the interface, and hence providing an improved link between the intended musculature and bony structure movement of the body with the movement of the prosthetic limb. The less the bone moves within the soft tissue, the better biomechanical and neuromuscular control will be achieved, reducing energy expenditure of ambulation.

As each of the stabilizing units and force distribution anchors may be separate, yet linked, there is an infinite amount of modularity and user adjustability, creating a fully customized fit, and ability to accommodate for residual limb volume change. The predominant surface area of the interface may be open, or mesh fabric, allowing for breathability and heat dissipation. It may, but not necessarily be, generally utilize conventional socket shape contouring, with the added benefit of adjustability between the various stabilizing unit segments.

This design may also allow for significantly lower trim lines at the proximal brim, and may not necessarily require specific brim elements as in conventional socket designs.

Figure 12A:
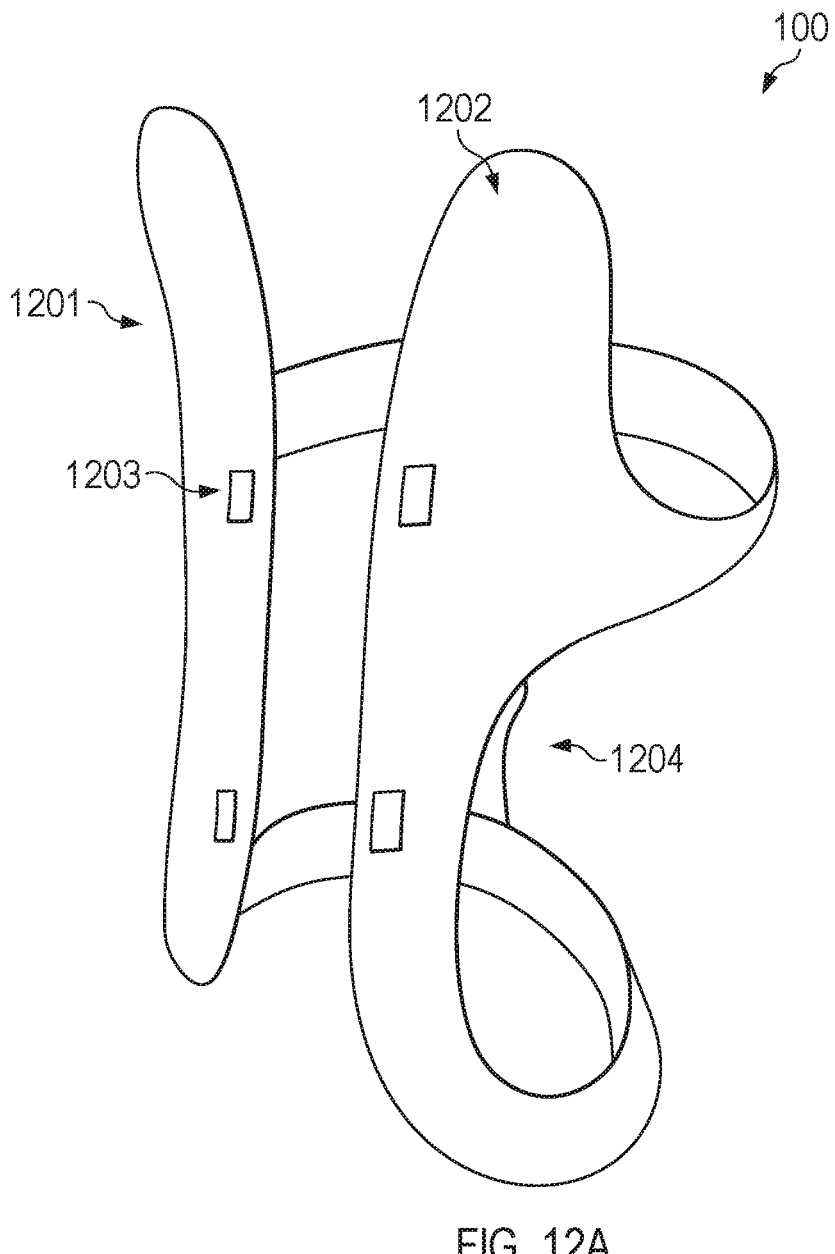
FIG. 12A illustrates another embodiment of an interface, viewed from the perspective angle.

FIG. 12A generally illustrates an embodiment where the force distribution anchors may not float, but rather may be structurally connected. In such an example, force distribution anchors 1201 and 1202 may generally run in an orientation along the long bone. In between them may be modularly adjustable connector means, which may also include compliant fabric. Connector means 1203 may allow the force distribution anchors to be pulled toward each other, tightening the interface about the limb. As fabric may be spanned or stretched in between the anchors, any long bone movement that may tend to press lateral, as in the case of a transfemoral amputee, may tend to push into the soft fabric, versus a rigid structure. In this embodiment, the interface may be fabricated to be slightly undersized for the user, thereby allowing it to have inherent compression about the limb, and inherent bony control. As the system may be tightened to the user, it may provide added compression. In general, a tight medial/lateral compression may be used, to help control the bone, and allow the tissue to bulge out the other areas. Not illustrated in FIG. 12A, but is in FIG. 12B, at the distal end may be a connector means to attach to other typical components used along with such a device. Such an embodiment may also utilize a vertical anchor stabilizer 1204 along its general medial side, as illustrated for a transfemoral use-case, to prevent flexing of the structure. Additionally, padding, or other compliant materials may be integrated to add comfort and conformability to the user.

Figure 12B:
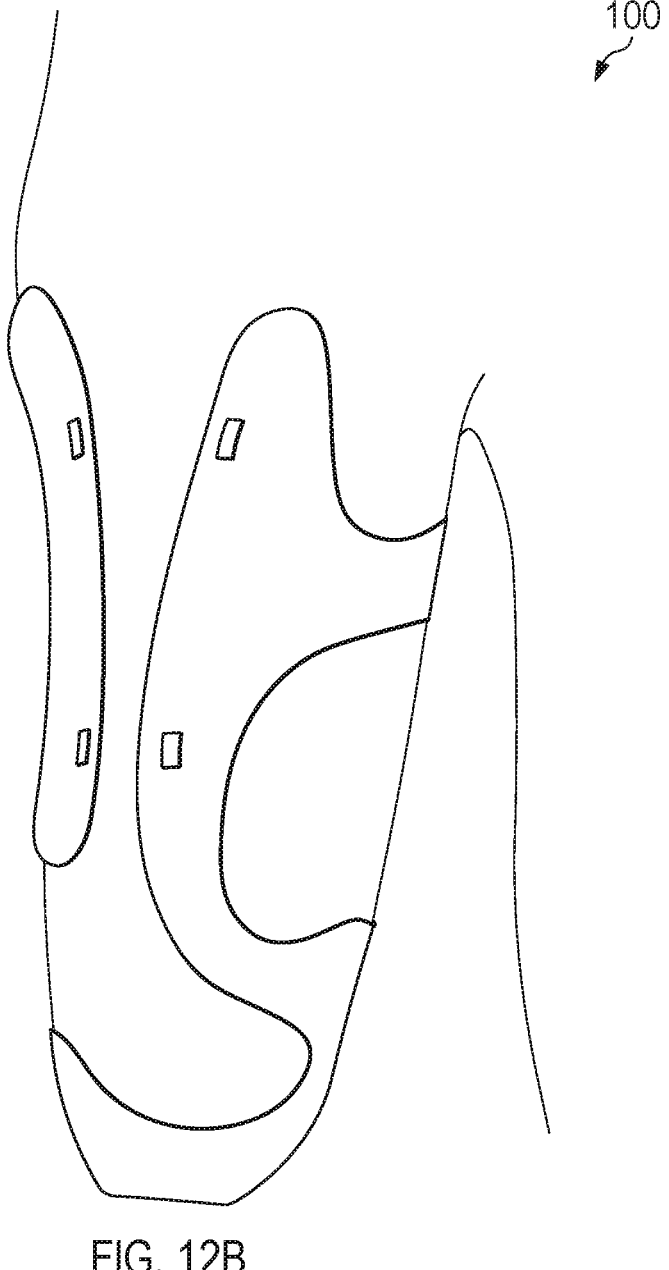
FIG. 12B illustrates another embodiment of a transfemoral interface, viewed from the perspective angle.

FIG. 12B represents an embodiment as donned onto a transfemoral use-case. This illustration does not show the connector means, but it should be understood that they may be integrated into such a system.

26

Figure 12C:
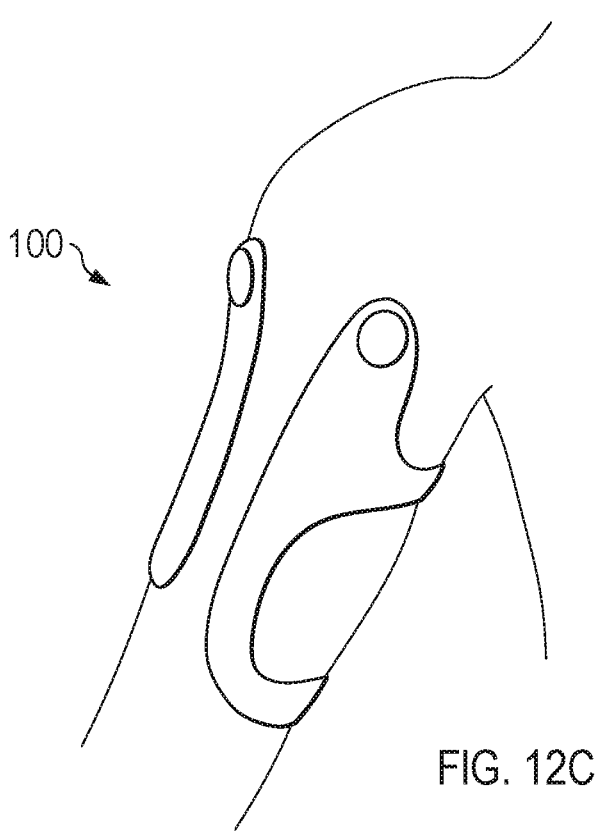
FIG. 12C illustrates another embodiment of an interface, viewed from the perspective angle, for use in upper extremity.

FIG. 12C represents an embodiment as donned onto a transhumeral use-case, and as may be used for non-prosthetic man/machine interface connectivity.

Figure 12D:
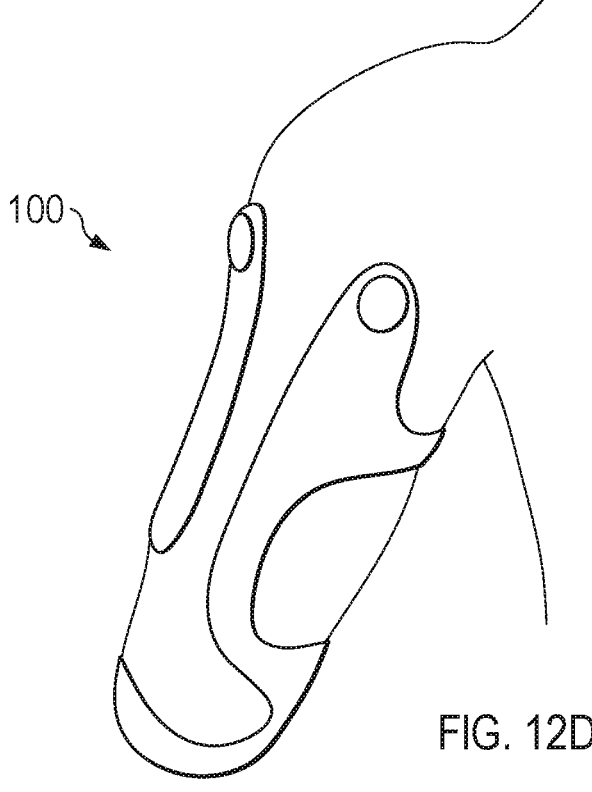
FIG. 12D illustrates another embodiment of a prosthetic interface, viewed from the perspective angle.

FIG. 12D represents an embodiment as donned onto a transhumeral use-case.

In each such case, the connector means 1203 may be used to draw the force distribution anchors together, tightening the interface around the limb, and providing control of tissue and bony anatomy.

Such embodiments may also be used on other use-cases including transtibial, and transradial levels, and all such corresponding orthotics levels to control the limb segments. In any such orthotics use-case obviously an open end may be used, as the limb may extend past the end of the device. Furthermore, any such embodiments in this disclosure may be used in exoskeletal robotics, as they are merely advanced orthotics devices.

FIG. 13 represents invention 100 donned onto a transfemoral amputee use-case. This illustration shows how the distal end of the interface may be contoured to the distal of the residual limb. This illustration also shows the proximal end of a flexible inner socket, gel liner, or other compressive sock 1301 to control tissue, as may be worn with the device.

FIG. 14 represents invention 100 donned onto a transfemoral amputee use-case. This illustration shows how the distal end of the interface may purposely be in non-contact with the distal end of the residual limb structure. In such an example, the distal end of the limb may be suspended with compliant fabric 1401 to give a similar effect as a rigid structure's support, but with compliant means. This fabric section may be spanned from the stabilizing unit(s) and force distribution anchor(s) distally to their corresponding components proximally to provide an anchor for its attachment.

Likewise, such a system may be used for casting of a custom medial or lateral anchor, whereas the remaining elements of the invention 100 may be integrated to such a casting jig, in order to cause the plaster which may be wrapped around the residual limb to be specifically contoured to the underlying anatomy as the force distribution stabilizing units are tightened down to the user. Integrated fabric may assist in capturing the contouring of the distal end within the casting process. Similarly, the fabric may be spanned around much of the limb, creating a hammock containment of the limb within fabric, replicating, or replacing a rigid interface that is conventionally used to hydrostatically manage the limb shape.

In an expanded modular embodiment, the stabilizing unit may be of a fully modular or modular semi-customizable component, which may either attach directly to the limb components, or may attach to a customized distal connector, which may attach to the limb components, as illustrated in FIG. 15. It is also understood that other numbers of force distribution stabilizers or anchor stabilizers may be used, and their shapes, sizes, orientations, and configurations illustrated in the figures should not be considered limiting.

In such example, attachment means 1501 may be any attachment method to known in the field, which may provide a structural attachment, and that in the figure is meant for illustrative purposes only. In such an example, the distal end of socket 1502 may be customized by the clinical practitioner, and modular stabilizing unit 1503 and force distribution anchors 1504 may be modularly connected within the system to make a complete interface, along with other subcomponents. As described previously in FIG. 8, over the years there have been a number of socket design iterations which the human above knee limb can fit into, and all of which have radically different socket shapes. This tells us that the human thigh can fit within many different shapes, where the stabilizing unit may reside. As such, an off-the-shelf stabilizing unit may come in various sizes, or may offer other compliant means such as padding, and may generally offer a shape that resembles that of the underlying anatomy, in which it may contour around. Likewise, there may be any number of stabilizing units, which may be modularly connected to a common customized distal attachment.

The embodiments represented may be custom fabricated, or may be pre-fabricated and sized to fit a variety of users, or may utilize a combination of both. Since they offer so much inherent modularity, a select few sizes will fit a variety of sizes of users. Additionally, conventional suspension systems available within the field may be used in conjunction with this design, including but not limited to distal cup or full length socket to provide vacuum or suction suspension, and which may be integrated into the invention.

Invention 100 may utilize at least one, possibly two, or more, stabilizing unit(s) to be modularly connected to distal base. In one embodiment as illustrated in FIG. 16, stabilizing unit may have a rigid or semi-rigid section 1601, which may extend up the length of stabilizing unit, or may attach to a separate stabilizing unit section, which may resemble the force distribution anchors in general shape or characteristics. Such base of the stabilizing unit may be connected with adjustable base 1602. Such adjustable base may utilize any adjustment means known, and those illustrated should not be considered limiting. In one embodiment, adjustable base may utilize a male to female pyramid setup 1603, where stabilizing unit section may be modularly adjusted in angulation. The opposing pyramid section may be modularly connected to a base plate such that the pyramid section may be adjusted in XY position on the base plate so that the desired femoral angle, weight line, and general biomechanics of alignment may be realized for the particular user. Connected to such base plate may be a mounting point 1604 for other prosthetic components. Alternatively, other attachment means may be used, and should not be considered limiting. Such base plate may be fabricated from metal, carbon fiber, or other such materials that may be sufficiently strong enough to support the user's weight and forces. Holes may be placed in the material to modularly adjust the mounting positions of the various components.

Pads:

As is generally illustrated in FIG. 17, in a preferred embodiment, such force bearing elements including but not limited to the struts, connector pieces, adjustable connector sections, gluteal span, or others, may utilize padding on their inner side to provide a more comfortable and gradual dispersion of forces about the limb.

In a preferred embodiment such pads may be modularly removable, in order to modularly replace the pads. The pads may utilize any conventional attachment means including but not limited to VELCRO, sticky material, fasteners, mechanical means, slots, or others.

Such pads may be available in various characteristics such as but not limited to thickness, durometer, flexibility, combination of durometers, combination of flexibility in various areas, width, tapering, attachment, or suspension methods, with varying surface characteristics, material selection, surface tension, surface friction, or other such characteristics.

In such an embodiment, by way of example, a thicker, wider, or stiffer pad may be used for a patient with a considerable amount of soft tissue, whereas a thinner or narrower pad may be used with a patient who is more muscular.

As may be generally illustrated in FIG. 18, in a preferred embodiment, the pads may utilize one or more durometers, or other characteristics as mentioned above. In such an example, a pad with more than one durometer may utilize areas of higher durometer 1801 and areas of lower durometers 1802. Such areas may be uniform across the pad, as may be layered, or may not be uniform across the pad. In such an example where there may be two or more durometers for example, a higher durometer for instance may be across the outer surface of the pad in order to increase durability against an external supporting member, and a softer area of the pad may be on the inner surface to allow for comfort and conformability to the user. In addition, other layers of various durometers or other characteristics may be used such as but not limited to, for example, yet another area of slightly higher durometer on the inner side of the pad to help disperse the forces more broadly by a middle softer section's compression. Similarly, the pad may utilize surface coatings or other materials adhered to its surface to accomplish the same. By way of example, fabric, VELCRO, plastic, nanotechnology, gecky-inspired technology, or other materials may be bonded or adhered to at least once side of a pad in order to provide such varying characteristics of the pad assembly, including suspension capabilities. The pad may be connected to a supporting or medial member by VELCRO or other commonly used connector means 1803.

Likewise, external materials or pad materials may have varying degrees of surface tension, friction, or sticksion. Materials may be used that have a high coefficient of friction against the underlying limb or liner, or it may have a low coefficient of friction to prevent tension against the limb or liner. In a preferred embodiment, it is contemplated that higher tension between the pad and the limb or liner is more advantageous to prevent the limb or liner from moving with respect to the pad.

In another embodiment, VELCRO or the like may be applied to the inner surface of such pad, or supporting members, in order to increase the coefficient of friction, or mechanical lock, to the underlying liner or the like. By doing such, the limb may be mechanically held within the socket by way of a mechanical lock. In conventional socket designs, this would be a limiting factor as doffing the device would be challenging. However, within this disclosure, the design inherently provides a socket that can be detached in such a way as to allow the user to effectively doff the device in a user friendly way.

As is illustrated in FIG. 19, there may additionally be various stackable materials 1901 that may each be modularly connected or disconnected. By way of example, various pads may be applied in series to allow for a change in thickness, or even tailoring of contouring by applying additional inserts between such a supporting element and a pad, thereby changing the shape within such a system. Such an insert may utilize hook and loop on its two sides respectively to simply be applied between and attach to supporting structure 1902 and the pad, or may be connected with any other known means.

In a preferred embodiment, and as one possible embodiment may generally be illustrated in FIG. 20, such pads may utilize raised or depressed shapes across its surface, in order to help increase the surface tension or mechanical lock between the pad and the limb or liner. Such shapes may be formed in many different characteristics including thickness, width, geometric or non-geometric shapes, design, texture, or otherwise.

Such shapes may offer various orientations such that they may inherently prevent the limb or liner from shifting proximally or rotationally. As is illustrated in FIG. 21, and by way of example, such shapes 2101 may have a general angulation such that the limb or liner is preventing from slipping past them. Such shapes may compress in certain directions, but expand in others. By doing so, the limb may be allowed to seat into the socket, but may be prevented from pulling out of the socket.

Such pads may be fabricated from one or more of various types of materials including but not limited to foams, silicones, rubbers, urethanes, plastics, textiles, mesh, fabric, or other such materials utilized in the industry or for interface applications.

It should be understood that the term liner should not be considered limiting, and may generally refer to any number of materials that may be applied over a limb, including but not limited to a gel liner, gel sock, fabric sock, sleeve, any combination thereof, or any other material or configuration that may be applied over a limb within a prosthetic or orthotic device.

In an alternative embodiment as shown in FIG. 22, such pads 2202 may be applied within a conventional socket shape 2201 to help increase rotational stability and/or suspension. In such a case the existing or conventional socket may be, but not necessarily is required to be, split in such a way as to be adjustable so that the socket may be tightened or loosened to accommodate for volume change, fit, or simplicity of donning and doffing such a system. In such a case, the insertion of such pads may help lock the position of the bone of the limb into a certain orientation by virtue of compressing the soft tissue around it.

Such pads, materials, shapes, or surfaces may mate with opposing surface of a liner, in order to increase a lock of the socket to the liner/limb. If a liner or the like may be used on the residual limb within such a system, such a liner may utilize a surface material that may inherently mate with such shapes or surface structure of such a pad. Such material or materials on the liner may amplify the effectiveness of a mechanical lock or other bonding methods with the pads.

In order to increase the surface bearing area of the interface about the limb, while maintaining a compliant interface, in a preferred embodiment, the vertical and/or horizontal connection section pads may utilize a connection means to an underlying compliant member that may be donned over the limb, such as a liner/sock. By way of example, a gel liner may be donned over the patient's residual limb. Such gel liner may utilize a surface covering that may have surface tension or other connectivity means to the interfaces connection sections (such interface connection sections may include any number of vertical struts, horizontal connection members, or other such sections). In a preferred embodiment, such surface to surface connectivity may utilize hook and loop VELCRO or the like. In a preferred embodiment, utilizing such a connection across and around a proximal band of the interface, or any area of such vertical interface sections, or any combination thereof or other, may allow for the remainder of the limb to suspend in a hammock-like manner within its gel liner, as is illustrated in FIG. 23 with VELCRO patches 2301 placed along supporting members to connect a liner for instance to the socket. It is contemplated that a similar effect may be achieved with a fabric sock, donning sleeve, shrinker, or other such compliant members, which may fit snug over the residual limb. It is also contemplated that such hook and loop may connect such interface to an underlying member along such vertical strut sections—which may include 1, 2, 3, or 4 of such vertical members, with or without combination with any number of horizontal connection members as well.

In such an example, the liner or sock element may have a certain amount of elongation potential as such material may be stretchy, or may have inherent compliance. Such underlying limb may generally be supported by such material, and such connectivity of such material to an external supporting structure may generally result in a hammock-type effect, whereas the liner or sock material may act as a hammock, the supporting structure (such as sections of the struts of a socket) may resemble a hammock-stand, and the limb may resemble a person laying in a hammock. In such an example, as a person may lay in a hammock, their entire body weight is supported by the hammock itself, which is supported by the hammock stand. In such an example, the person's full body weight is distributed over a broad surface area and such hammock is conforming to the shape of such body, resulting in a comfortable interface. In the prosthetics equivalent example, the liner or sock may generally support the user's weight, as well as biomechanical lock about underlying anatomy. The liner or sock may help prevent expansion of the tissue in elongation, circumferential expansion, or other, or any combination thereof. Additional elements may be applied to the liner or sock to further help control and/or manage the tissue within the system. In one example, and as described in additional patent application by this same inventor, a flower shaped connector may be applied over the distal end of a liner or sock, eliminating, or reducing elongation or circumferential expansion of the liner, and creating a form fitting socket over the end of the limb. Likewise, it is contemplated that non-elongating hook VELCRO type strips, or other methods, may be connected to a liner or sock which may be not have integrated anti-elongation strips, and such combination may be used to prevent elongation of such liner or sock.

Alternatively, other methods may be utilized to quickly create a form-fitting socket about a residual limb such as impregnated at least a portion of a fabric sock or the like with a material in a general liquid form, which may then hold its form upon changing it state. By way of example, materials such as silicon, urethane, or other similar materials may be used. Such materials may get impregnated into at least a portion of a fabric sock (or functionally similar article) that is donned over a limb, and which is then able to set off, providing a form fitting socket to a user. The sock may give compression to tissue and conforming around the limb. The impregnated silicon for instance becomes the structure element, and setting off in the socket gives the shape.

Ladder Strap With Numbers:

In a preferred embodiment, a connector means may be used which may offer documentable increments of tightness. In one such embodiment, a ratchet and ladder strap may be used which may offer numbered or use other increments which may be used to alert the user or practitioner how tight such a connector piece is. In a preferred embodiment, such a ladder strap may utilize numbers listed on various ladder increments. Such numbers may be listed in order, and such numbers may begin at the mountable end of the ladder, such that the open end of the ladder may be cut to length, and allow the remaining numbers to remain in order starting with the lowest and working upward as it extends to the cut end of the ladder strap.

Such numbers may be listed on each ladder section, or may be listed by increments of two's, five's, ten's, or other. Such numbers may as well be linear along the strap, or may be offset at angles to enable the user to better read the position, without having to fully read the actual individual number. In such a case, the numbers of increments of fives may be on the far left side for example, and the following numbers may stair-step in position across the ladder. The same may be accomplished in sets of 10's. It is contemplated that only the fives or tens may be listed on the ladder strap, and the remaining rungs in between may not have numbers listed.

FIG. 24 generally illustrates one embodiment of such ladder strap with numbers along the rungs of the ladder.

Likewise, cross connector pieces may be used with numbers as well to alert the practitioner of the position of such connector between such interface sections.

FIG. 25 generally shows an embodiment of a cross connector strap with numbered holes. The hole at least one end of such connector may be offset by a certain amount to increase the number of possible positions of such a strap. For instance, if each hole is ½" apart, the hole numbered 0 may be offset by ¼" from the other holes, such that the entire strap may have ¼" increments with larger hole spacing, providing a more durable strap.

Components and Fit:

In a preferred embodiment, modular components may be used to alter the position and angulation of at least one, and preferably two, vertical supporting members.

Such supporting members 2601 may be fabricated from thermoformable or non-thermoformable materials. In a preferred embodiment, thermoformable materials may be advantageous to contour such members to the underlying anatomy, especially on the proximal end. It has been found that it is not necessary to contour any supporting member (or medial vertical member for that matter) at all and maintain full functionality and comfort. Thermoformable members may be made of thermoformable carbon fiber, injection molded plastics, or other materials. In a preferred embodiment, such members may be fabricated from injection molded plastics. Such injection molded materials may utilize nanotechnology to increase their strength and rigidity.

Such vertical supporting members in a preferred embodiment may generally be positioned along the lateral and/or anterior lateral aspect of a transfemoral limb for instance. One supporting member may generally be positioned between the hamstrings and the lateral aspect of the quadriceps, and generally run from posterior to the distal aspect of the residual bone to the pocket hollow area, just posterior to the proximal aspect of the residual bone. A second supporting member if used may run from anterior to the distal end of the residual bone to anterior or anterior/lateral aspect of the proximal end of the residual bone. By positioning such supporting members like this, the distal end of the residual bone may generally be positioned to float there between, leaving no structure in which the sensitive end of the bone may hit against.

Between the supporting members, toward the distal end, but proximal to the distal end of the residual bone, a compliant bridge 1708 may span there between, allowing for a pad to be placed to post the bone, and control its position and movement.

In such a system it is contemplated that the distal end of the residual limb may not need to be in direct contact with the distal end of a socket, and instead may generally float with no contact with any rigid or semi-rigid structure. Instead, the use of a sock or liner may be used as a "hammock" to support, manage, or control underlying tissue within the system, and functionally act like a conventional rigid socket may act about the limb.

It has been shown in conventional socket designs that encapsulate the limb that a lack of distal contact with the end of the socket may result in circulatory issues of that tissue, and is generally contraindicated. However, since this socket design does not encapsulate the entire limb, and since the hammock effect is utilized to control and manage the tissue, having lack of contact about various aspects of the limb including the distal end is found to be more comfortable by wearers. The underlying limb and tissue may be supported by a compliant hammock instead of being supported by a rigid socket.

The proximal end of at least one of the supporting members may be connected to a compliant band or swing strap 1704 (FIG. 17) that may span around the medial aspect of the limb and back to the other supporting member, or itself. By way of example, such compliant band may span from the lateral posterior supporting member around the gluteal area, under the medial aspect of the groin, around the anterior aspect of the limb, and connect back to the lateral anterior supporting member. In such an example, such compliant band may be functional similar to how a climbing harness may function in supporting the body.

The term compliant band should not be considered limiting and may encompass webbing, fabric, plastics, foams, laminates, or any other material. Such band may additionally include areas that are more compliant and areas that are less compliant, and may even have rigid areas within. In a preferred embodiment, the compliant band may be fabricated from fabric webbing material such as nylon webbing for at least part of its span. Such compliant band may utilize means for attaching a pad across it, such as a foam pad, and such means of attachment may utilize VELCRO or other attachment means. It is understood that such compliant band may not be in one piece, but may include various pieces to make up such band. Other sections of such band may include a length adjustability means, such as but not limited to a ladder strap, which may engage in a ratchet mechanism.

Any such ladder strap or cross connector sections may utilize a connectivity means across their back side, such as but not limited to VELCRO for example, which may then attach to a pad to help distribute the forces over a broader surface area.

Through using a section of the band, which may be disconnected, such as a ladder strap and ratchet mechanism, such socket design may be disjoined, allowing it to be opened up. By way of example, a limb shape is generally round. Socket shapes are therefore typically generally round to match the underlying limb shape. By opening up the socket, the socket may be splayed open, and may generally lay flat. This may allow the user to more effectively or easily donn such a device.

Such band may as well connect to other members. For example, a general medial vertical structural member may be connected to the band near the tuberosity area and generally run distally from there. Another medial vertical structural member may be connected to the band near the anterior aspect of the adductor longus tendon and generally run distally from there. Such medial vertical members may be connected together, as well as connected to the lateral supporting members at some more distal level. The medial vertical members may help prevent the proximal band from digging into or roping into the limb, by spreading the forces down the length of the limb by virtue of its connectivity. In addition, this compilation helps to control and manage the underlying bone more effectively.

In fabricating a conventional socket, great care is taken to custom tailor the shape of the socket shape for the user. The socket is typically hand sculpted to match the underlying anatomy, such as around the adductor longus tendon, around the ramus, at the distal end to provide space for the distal cut end of the bone, and around the muscle bellys and soft tissue. Since the human body is so dynamic, the custom tailored socket will likely no longer fit appropriately with just a small change in body weight. When a practitioner needs to make incremental changes to the shape or contouring of a socket, during the fabrication and fitting processes, they will likely use a heat gun to modify the thermoplastic socket, or grind part of the material away of the socket, or place pads within the socket. Each of these adjustments is time consuming, is inexact, and is not simple or often not possible to reverse.

Similarly, long ago the alignment of a prosthetic was equally as inexact and challenging, by requiring the socket to be cut off from the underlying components, repositioned, and bonded back on in order to make even small alignment changes.

In years past endoskeletal components were introduced to the prosthetics field, which use a male pyramid and female receiver to provide incremental, simple, and reversible adjustments to the alignment. This addition revolutionized the fitting process of a prosthetic, as even minor modifications could be done to the alignment in real-time. Those changes could be reversed. And those changes could be quantified, and documented.

In a similar way, the prosthetics field needs a method of documenting and quantifying the prosthetic socket fit. There is also a need to allow a practitioner to be able to simply, quickly, and easily modify the fit in each of the areas of interest in real-time, to test how a change may feel to the user, and be able to just as easily reverse that change. Current prosthetic fitting approaches do not allow for that to take place.

This disclosure allows for just that to happen. Through the use of the various cross connectors, adjustment mechanisms, and swing strap, every aspect of the fit of a prosthetic can now be adjusted in real-time-all of which are quantifiable, documentable, and reversible. Such cross connectors, swing strap, and adjustment mechanisms may be flexible, compliant, soft, or otherwise conform for the user with varying degrees of flexibility.

The cross connectors in this design may utilize incremental adjustment means to alter the distance between their connection points. In one embodiment, this may be holes in a strap, though this should not be considered limiting, as there are numerous embodiments that could accomplish the same.

Beginning with FIG. 17, the proximal medial connector 1702 connects the two medial floating members 1703. Each floating and anchor member may utilize methods of attaching cross connectors, such as incremental holes to provide anchor points, although other attachment methods are contemplated, and should not be considered limiting. As this section is tightened, it allows for the proximal medial swing strap 1704 to have more space, and hence can have additional room for the adductor longus tendon and related anatomy. In typical sockets, the socket shape is contoured around the anatomy as such, and the contouring of this disclosure can highly resemble a conventional socket contouring, by making this incremental change to the tightness of the cross connector.

Cross connector 1705 on the medial distal aspect of the socket may be used to adjust the angle and span of the two floating medial members. This may impact the available circumferential positioning of the medial members as well as the relative and available positioning for the anchor members.

The proximal posterior cross connector 1706 may influence the amount and shape of contouring of the swing strap. It may also influence the amount of suspension of the swing strap to support the users, as well as the relative positioning of the posterior medial floating to the tuberosity area. The distal posterior cross connect also may have influence on the circumferential positioning of the medial members as well as the relative and available positioning for the anchor members.

Lateral proximal cross connector 1707 may provide added system rigidity by preventing the anchor members from splaying apart under load.

Distal lateral cross connector 1708 may be positioned proximal to the cut end of the bone, such that a pad may be placed between it and the user if chosen, and may post the bone. By doing such, it may control the position of the bone within the socket, and provide increased bone control and comfort for the user.

Anterior connectors 1709 may be adjustable, and removable, such as ladder and ratchet straps. In such an example, incremental adjustments to the circumferential tightness of the system can be accomplished.

Each of the cross connectors, and ladder, may use markings to show relative positioning, such as numbering their ladder rungs, or holes within the cross connectors, or other means, so that a practitioner or user can compare and quantify relative positions, and document such positions. With so many adjustment means within the system, a practitioner can custom tailor an entire socket, in each and every area which a socket needs to be tailored, but in a quantifiable, documentable, and quickly and easily reversible manner. This allows a practitioner to test various fitting changes in real-time.

If padding is needed, pads may be applied between any such cross connectors or ladders and the user. Such pads may be attached in any number of methods known in the industry, including VELCRO, or bonding them.

In addition, the swing strap 1704 may be attached to its ends in such a way as to allow for incremental adjustability to adjust tightness and suspension. Such swing strap may be fabricated out of any number of materials, but in a preferred embodiment, it may be fabricated from nylon webbing or the like, which is very durable, very lightweight, and very flexible. Such swing strap may incorporate a means for connecting a pad, such as VELCRO. Such pad may be connected to the swing strap, and provide added cushioning and comfort to the user, as well as to control and manage tissue. Any such pads within such a system may be removable for washing, replacement, or adjustments, such as skiving the pad to a different shape to accommodate for contouring of the limb or comfort.

Such swing assembly may be connected to the lateral anchor members on their proximal ends. In one embodiment, the posterior aspect of the swing assembly may connect to the posterior lateral anchor member, and the other end of the swing strap may connect to the anterior medial floating member. That anterior medial floating member may then have an adjustable strap connected from it to the anterior lateral anchor member, providing a complete connection around the medial aspect of the limb, to both anchor members. By doing such, the proximal brim may act more like a swing or hammock, and the anchor members may act like a hammock stand.

A floating member may utilize a more flexible member 1710 attached to it on the user side of the member, such that the proximal end of such floating member may have gradual tapering of relative stiffness, preventing it from digging into the user on its proximal edge.

In such configuration of the swing strap and flexible members, the entire proximal brim may be flexible and compliant, lacking rigid or hard elements as are found in conventional prosthetics. Conventional prosthetics all use a rigid shelf to seat area to sit onto near their tuberosity area, which is uncomfortable for the user. In this disclosure however, such proximal brim may be entirely compliant, allowing for there to be no hard shelf, but rather a brim shape that more resembles a hammock or swing instead.

Toward the distal of the medial floating members, at least one of such members may be modularly connected to the main base, such as the mounting point where the knee may attach. This may be accomplished by a dynamic tab, which may allow for infinite 360-degree rotation at its attachment to provide optimal positioning about the limb. Such dynamic tab may allow for another connector piece to be attached, such as but not limited to a ladder strap. Such ladder strap for example, may then connect to a ratchet, which may be mounted on a medial floating member. Connecting the two together with a compliant strap such as this allows for the medial floating members to be pulled distally, which inherently tightens them against the limb as a 4-bar linkage operates. This may help to solidify the structure of the socket as a whole, even though many of the connectors may be quite compliant and flexible. This unites the socket and the limb into one functional element, providing a greater one-to-one connection between the limb and the socket, and hence underlying bone to socket.

It is contemplated that similar means may be used for other limb levels, such as transtibial limbs, and in such examples, the lateral aspect of the limb may not be the preferred positioning, as it would be for a transfemoral use-case. Such positioning may be custom tailored to the prosthetic level, and more specifically to the users' requirements. In addition, it is contemplated that the supporting members for a transfemoral design may as well be positioned in positions other than just the lateral posterior and lateral anterior aspects of the limb.

The use of any flexible contoured "socket" about the limb may be supported by such a system. If such underlying socket were fabricated from conventional or similar materials, the modularity of this system may allow for an end user to self-adjust the socket. Conventional fittings typically use a custom fabricated inner socket shape to the user. This disclosure certainly could become the frame around such inner socket shape, allowing for the benefits of using a conventional inner socket if the practitioner should choose to use such a device, and take advantage of the adjustability and simplicity of fitting this design around it.

To fit such a system to a user, the use of modular components may be utilized to fine tune the position of supporting members about the limb. In general, each supporting member(s) 2601 (and by example, one on the lateral posterior aspect of the residual bone, and one on the lateral anterior aspect of the residual bone) may be connected to an adaptor 2602 which may connect it to a modularly adjustable component. By way of example, such adaptor may be in the form of a through-hole tube clamp type of adaptor. Such adaptor may connect to the supporting member, and may connect to a pylon 2603, although other embodiments, and even more simple embodiments, are certainly contemplated, and such example should not be considered limiting.

This configuration may allow for such vertical supporting member to be adjusted in position up and down with respect to the body, as well adjusted in rotation so that it may lay flat against the body.

Such tube or pylon, which connects proximally to the through-hole tube clamp adaptor or the like, may then connect distally to a typical tube clamp or female adaptor 2604, which may then engage with a male pyramid 2605. Such intersection may allow for modular adjustability of the angulations of the vertical supporting member(s).

Such male pyramid may be connected to a horizontal plate 2607. Such plate may have various possible positions in which the male pyramid may be mountable, in order to alter the lateral positioning of the supporting member with respect to the limb. This may help accommodate for various size limbs.

As illustrated in FIG. 27, such horizontal plates may be connected together with through hole bolts, which may connect to a four-hole plate on the inside of the device, and may connect to a four-hole male or female pyramid on its distal aspect, which may be then be connected to a knee or other components.

If more than one horizontal plate may be used, it may utilize adjustable means to modularly adjust the position of one plate with respect to the other. Through such a slot configuration as is show in the illustrations, 360 degrees of adjustability may be realized for each plate. It is contemplated that 1, 2, 3, or 4, or more plates may be utilized within such a system. Such plates may be marked to quantify their relative positions.

Such components may be used for in-office fittings, to allow a practitioner to set the position of the supporting struts to the user, and establish general alignment of all aspects of the device. They may also be used for definitive use as needed.

Various methods of connectivity for any such components are contemplated, and those described should not be considered limiting.

When transferring from the fitting components to a definitive setup, the fitting components may be placed in a typical transfer jig in order to capture the alignment and position of the supporting struts with respect to the underlying component such as the knee and foot. The struts may be swapped for dummy struts, which may be used for laminating a distal socket, and replacing with the actual struts after the lamination, or the like, is fabricated.

Alternatively, a modular adjustor mechanism may be used to connect the supporting members to the distal end. While there are various embodiments that may be utilized to connect the supporting struts to where the knee or distal components connect, the example of a preferred embodiment as described below captures various preferred characteristics of such a system, including simple modularity, cost effective, and low profile design.

In a preferred embodiment, such components may allow for infinite adjustability to custom tailor the connectivity position to the user, so that a select few components may be used for many different configurations. Simultaneously, such components should be able to remain very low profile and contoured about the residual limb whereas to not result in a bulky socket.

In one embodiment, as generally illustrated in FIG. 28, such distal attachment plate may be formable, such as but not limited to thermoformable, so that after use of it with the other fitting components to establish proper alignment and positions, in a transfer, its lateral end could be heated, for example, and bent into position, creating a bent structural supporting member to connect the knee attachment area to the strut.

Alternatively, such distal attachment plate may be cut to length, and a secondary curved member may be attached, which may or may not be thermoformable, to allow for connection between the distal end knee attachment area to the supporting members.

Any such component of the fitting system may utilize branding on it, including the proximal four-hole attachment plate.

Transhumeral Socket

In a similar method as described for transfemoral applications, a similar set of components may be used to fit other levels of amputations. For example, in a transhumeral fitting, a supporting member may be used which generally may have a distal attachment plate to mount to components such as a prosthetic elbow. Such plate may be near 90 degrees to the long section of such member, which may generally run along the length of the residual limb, toward the axilla, though may be located on either side of the limb. Attached to at least one supporting member may be at least one floating members. Such floating members may functionally act similar to the floating medial members of the transfemoral use-case example as described previously. Such floating members may generally reside on the medial aspect of the arm, and/or may reside just lateral to the biceps and/or in between the two heads of the triceps. All three (for example) members may be joined with compliant connectors. Such compliant members may be similar to those of the transfemoral fitting level, although their characteristics may be slightly modified such as in flexibility, method of adjustability, or width, or others. Disconnectable adjustors may be utilized to allow the system to splay open. Such adjustors or connectors may be able to be adjusted in position or tightness, allowing the user to self-tighten their fit. Such connectors may encircle the limb, connecting all floating and supporting members together around a limb. Each of such members may have means for connecting a pad within, and may additionally utilize connectivity means to an underlying liner or sock, as described in the transfemoral section, including, but not limited to VELCRO.

Similar to the dynamic tab as described in the transfemoral socket example, the floating members may be connected to either the distal end of the main support member to provide the 4-bar linkage effect to lock the socket about the body more effectively. Alternatively, the floating members may be connected to the harness, such as vest harness (MartinBionics) design, and such connectivity force may accomplish the same. Or a combination of the two may be used.

For upper extremity users, the use of a sock or liner to control and manage the residual limb tissue can still be quite valuable, and can be used to further distribute the forces over a broader surface area, and provide suspension capabilities. Using VELCRO, for instance, to connect a liner to the pads of the floating or support members can be an effective way to achieve suspension.

Similar to that described in the transfemoral level fitting, cross connectors, adjustable connectors, and other such elements may be incorporated within, to allow for quick and easy modular adjustability of the fit in every area of the socket where a practitioner may typically fit the prosthetic to the user through conventional tailoring methods.

The proximal medial aspect of the socket may utilize a floating brim design, and in a preferred embodiment may be made of comfortable materials such as fabric and/or foam, by way of example. Other materials may be used as well. Such floating brim may be connected to anchored and/or floating struts, and may be adjustable in length. Such floating brim may provide accommodation to the dynamic nature of the axilla area, and provide additional comfort. Such brim may functionally be similar to the medial brim of the transfemoral application socket.

FIGS. 29A-29E generally illustrate various embodiments of how such a socket may engage around a residual limb at the transhumeral level. Similar means may be used as described in the transfemoral level, though specific to the anatomy of this limb segment.

Transradial Socket

Likewise, a similar method may be used to connect such a device for a transradial limb. In such an example, at least one supporting member may be applied along the anterior or posterior aspect of the lower arm (front or back of forearm), as in the position on an anatomical chart. Such floating member(s) may run along opposing sides of the arm. All such members may be connected together with compliant connectors, and at least some of such connectors may be quickly and easily adjustable, and may be able to be splayed open, versus remaining as a socket, which by definition is a natural or artificial hollow into which something fits. It is contemplated that other configurations may be utilized to accomplish the same.

The use of such an open socket, versus a traditional encapsulated socket, inherently allows for the system to not trap as much heat, be considerably cooler, lighter, more breathable, and allow for simpler and more effective connectivity of EMG controls or other such sensors.

Similar to the transfemoral use-case example, the proximal anterior (front side of arm in the anatomical position) aspect of the socket may utilize a floating brim, which may be made of comfortable materials such as but not limited to fabric, webbing, foam padding, or others. As the elbow may flex, the comfortable materials may match to the underlying dynamic body, providing additional comfort. Such brim may be connected to floating member, anchor members, or a combination of both. It may also be adjustable, allowing the socket to be tightened to user preference.

Through allowing a supporting member to be attached to floating member(s) provides an opportunity that conventional socket designs cannot. For instance, VELCRO, or other textured materials, would be impractical for an amputee to use in a conventional socket for suspension, as there would not be a way of releasing it since a hollow socket cannot open up. But since this/these designs can be splayed open through the use of the floating struts, such a system can utilize VELCRO, or other such connectivity means, and the user can still doff the device when needed with ease, yet have incredible suspension capabilities when the socket is donned.

For any such fitting level application, a conventional socket, or a portion of a conventional socket may be attached within the system to utilize benefits of conventional socket fitting or suspension methods within such a system. Such a socket may be connected to the supporting members, the floating members, or a combination of both. Likewise, it may not be connected to either, and only be connected to the distal end.

FIGS. 30A-30E generally illustrate various embodiments of how such a socket may engage around a residual limb at the transradial level. Similar means may be used as described in the transfemoral level, though specific to the anatomy of this limb segment.

Transtibial Application

Transtibial use-cases may be highly similar to the transfemoral application in many ways, though with slightly different configurations of similar components. For a transtibial application, supporting member(s) may be used on the anterior, lateral, medial, and/or posterior sides, although in a preferred embodiment they may be located at least on the anterior side. There may be at least one such supporting member, and in a preferred embodiment perhaps two.

In one embodiment, a supporting member may run along the anterior lateral aspect of the tibia bone, while another supporting member may run along the medial aspect of the tibia bone. Floating member(s) may be used along the posterior aspect of the limb, such as up the middle or sides of the gastrocs muscle belly.

Alternatively, supporting member(s) may be used along just the medial aspect of the tibia for instance, with floating members along the anterior lateral aspect of the tibia, and/or along the posterior aspect of the limb.

Alternatively, a supporting member may run along the posterior aspect of the limb, with floating members along the anterior lateral and anterior medial aspects of the tibia.

In any such configuration, similar connector means and self-tightening means may be used to connect supporting and floating members together around such a limb, as has been described in the transfemoral configuration example. In addition, such system may also utilize pads, dynamic tabs, and other such components of a transfemoral system, but configured specifically to the transtibial level.

Spanning within and between such anchor and floating members may be various configurations of pads, which may be used to contain and control tissue management within such a socket. Such pads may or may not be connected together distally.

At the distal end of the socket may be an attachment point for modular components such as pylons or feet, as would be typically found in such applications.

In one embodiment, the posterior proximal aspect of the socket may utilize a floating brim, which may be made of conformable materials such as but not limited to fabric, webbing, foam, or others, by way of example.

Further, since such a socket may be able to splay open, it may accommodate for volumetric change by tightening up or loosening the circumferential dimension of the socket, by way of adjustability means as illustrated in the figures.

Any such sockets may utilize areas of custom molded contouring about the limb shape, in addition to purely modular areas of conformity. For instance, custom molded areas around the tibial and femoral condyles may be accomplished through custom molded areas as in conventional fitting methods, which may attach to the modular areas, or such area may utilize off-the-shelf section that may then be customized to fit the user.

FIGS. 31A-31G generally illustrate various embodiments of how such a socket may engage around a residual limb at the transtibial level. Similar means may be used as described in the transfemoral level, though specific to the anatomy of this limb segment.

Liner Suspension

In conventional prosthetics, gel liners are used to provide cushioning for amputees, within rigid sockets. With this disclosure, there may not be a rigid socket, and hence the requirements for and advantages of a gel liner may be distinctly different. In conventional sockets, there is vacuum that is created between a liner and an encapsulated socket to help hold the prosthetic in place. A seal is formed between the limb and socket or liner and socket to achieve such suspension. In this disclosure, a gel liner or air impervious liner may be used to suspend the prosthetic, by attaching it directly to the prosthetic with mechanical means, or other. For instance, and by way of example, a gel liner with loop VELCRO on its outer covering may be mechanically connected to VELCRO hook, which may reside on the inner surface of anchor or floating members of this disclosure. Because this disclosure offers a device that can be effectively unwrapped from around a limb, versus a traditional bucket socket, the VELCRO may be used to mechanically connect such VELCROs together, maintaining suspension. Because the gel liner may not allow air to enter, it may effectively be held onto the limb with suction, negative pressure, or vacuum.

Attaching a liner in removable manner, as generally illustrated in FIG. 32, to a strut type of design directly, for suspension, is unique for use in prosthetics, as no other strut type of designs used in prosthetics utilize a removable connectivity between the two for suspension.

Swing Brim

Users of conventional prosthetic sockets often experience discomfort in areas such as the proximal brim, such as the ischial tuberosity, ramus, and general proximal medial, anterior, and posterior aspects of a conventional socket. In such conventional sockets, the dynamic limb is encapsulated within a static socket shape, which results in rubbing, chafing, and pressure in these unwanted areas.

It has been discovered through the use of compliant brim designs, such as those disclosed in this application and its priority applications, that the user can remain significantly more comfortable if the brim materials can conform to the user, versus the user having to conform to the brim. As such, the incorporation of the disclosed brim design within a conventional prosthetic socket can significantly increase the comfort of the conventional socket.

To accomplish such, various fabrication integration options may be used, and those described below should not be considered limiting, but rather are for examples of various options. It is understood that various other options, including various trim line options and attachment options may be used.

In a preferred embodiment, the swing webbing may incorporate contouring such that it may assist in laying at the correct angle and orientation around the underlying anatomy as it wraps around the limb. In one such example, an illustration can be found in FIG. 33 showing one such configuration. In a preferred embodiment, one side of such webbing material may be VELCRO compatible, or other attachment methods, allowing for padding to be attached to it, which may help further spread forces and add comfort.

The ends of such swing webbing may attach to the frame or struts with conventional attachment means, which may include, buckles, rivets, screws, sewn in place, or the like. Such attachment means may be adjustable or non-adjustable as the practitioner deems necessary or preferable.

Option 1 as illustrated in FIGS. 34A (lateral view), 34B (posterior view), 34C (medial view), and 34D (anterior view): Conventional flexible inner socket with Socket-less Socket Swing Webbing and frame. Inner socket may or may not be trimmed down.

A conventional flexible inner socket may be removed from a conventional frame, and replaced with a Socket-less Socket frame structure around the conventional inner socket. Doing so may eliminate the rigid ischial seat, as it would be replaced by the swing webbing, which may generally span from around the lateral posterior strut, connect to the posterior medial strut, and span anterior toward the anterior medial strut and anterior lateral strut, forming a swing shape, with the two lateral struts as the hammock stand.

Since the medial struts may generally float with respect to the distal mounting method, and hence not have a rigid structure underneath, the medial brim of the socket may generally offer greater compliance, and more comfort. The socket-less socket frame around a conventional inner socket may also offer greater adjustability, by allowing for ratchet or similar adjustment means to tighten the span between various struts, causing the flexible inner socket to become tighter around the limb.

This may also expedite the fitting and fabrication process over conventional means, as well as create a more modular fitting method.

If the flexible inner socket is trimmed down from its original shape, the advantage of the swing webbing with integrated padding may be used to replace a portion of the brim of the conventional socket. For instance, the posterior and medial aspects of the conventional brim are typically uncomfortable in sitting and standing. Trimming these areas lower and replacing them with padding over the compliant swing webbing may allow for greater conformity and comfort.

Specific areas that stand to benefit from adjustments include:

Posterior brim: This area is often bulky in sitting on a chair, and uncomfortable in sitting. Lowering this area and replacing it with webbing provides a lower profile build height, and hence more comfort.

Medial brim: This area is especially uncomfortable in conventional sockets, as the medial brim typically uses a rigid ischial seat, and static ramus shape. Much of the discomfort experienced in conventional sockets is in this area. Replacing the brim with conforming webbing material for instance, allows it to conform to the user, versus the user conforming to the static brim shape.

Anterior brim: This area is often uncomfortable in sitting, as it presses into the abdomen during hip flexion. In conventional sockets, this area posts off the abdomen, and can cause a loss of suction in sitting activities. By replacing this area with flexible conforming fabrics as a brim material, it no longer posts against the abdomen, allowing for better retention of suspension and comfort.

If the conventional inner socket is trimmed down, it may be trimmed in any or all of the above mentioned areas, including as well the lateral side. This may functionally allow for the inner socket to function much like a traditional socket-less socket fitting, but utilize and existing flexible inner socket. If the conventional inner socket remains intact in part or in its entirety, the comfort may still be greater by eliminating a rigid ischial seat, and allowing the brim in general to have more conformity than a conventional frame surrounding it.

While there may be more conformity, the swing brim may simultaneously capture and control the tissue, and prevent ballooning of the tissue in this area, as well as cold creep of the plastic, since it will be supporting the underlying flexible inner socket with a non-stretch material.

Option 2 as illustrated in FIGS. 35A (lateral view of conventional inner socket trimlines compared to Swing Brim trimlines), 35B (posterior view of conventional inner socket trimlines compared to Swing Brim trimlines), 35C (medial view of conventional inner socket trimlines compared to Swing Brim trimlines), 35D (anterior view of conventional inner socket trimlines compared to Swing Brim trimlines), 36A (lateral view of conventional frame trimlines compared to Swing Brim use trimlines), 36B (posterior view of conventional frame trimlines compared to Swing Brim use trimlines), 36C (medial view of conventional frame trimlines compared to Swing Brim use trimlines), 36D (anterior view of conventional frame trimlines compared to Swing Brim use trimlines), and 37A, 37B, 37C, and 37D of integrated Swing Brim on a conventional socket: Conventional flexible inner socket and frame with modified trimlines of both, to incorporate and replace the use of the a Swing Brim instead of static brim plastics.

Similar to option 1 above, remaining with a conventional socket AND frame, both with modified trim lines, may allow the brim of the socket to benefit from a more comfortable compliant swing webbing, while maintaining a consistent fit within the remainder of the socket.

To accomplish such, the posterior, medial, and/or anterior brim of the conventional flexible inner socket and its surrounding frame can be trimmed down in various amounts as needed or desired, allowing the limb and tissue to be encapsulated by the swing webbing and padding instead of the conventional more rigid materials.

The swing webbing may be attached to the lateral posterior and lateral anterior frame areas, in similar positions as may be used with a socket-less socket frame configuration.

The contouring of the conventional flexible inner socket trim lines may as well utilize areas to resemble the strutserts of a socket-less socket configuration. As such, the flexible inner socket may extend upward near where the medial posterior and medial anterior struts may reside, and allow the swing webbing to attach to the flexible inner socket extension areas. Likewise, between any of the various areas of the swing webbing, but preferably in the anterior section, the swing may be adjustable, allowing for the user to tighten or loosen the fit of the swing brim.

Referring to FIGS. 26A-26B, such fitting components may utilize a method of determining the relational position of various fitting components with respect to others, including angles, positions, rotation, and height amongst others. Such method of determining relative positions may be used to determine the final alignment of the device, and used for definitive stage transferring. For instance, the position of the laminating plate (or its equivalent) with respect to the two through hold tube clamps which anchor to the two lateral struts may be used to determine how the final assembly is fabricated. Knowing those positions with respect to each other may enable one to fabricate a definitive lamination for instance, without having to have the specific components in hand, such as if a central fabrication facility may be doing the fabrication work.

In such an example, this may be accomplished through electronic means, with marks, or the like, on the fitting components to determine relative positions, or other such means. In any example, the method should provide a quantifiable determination of the angular, rotational, positional, or other orientation of the device.

Socket-Soft

Using modular elements to assemble a socket about a user's limb allows for various configuration options to be quantifiable, recordable, and repeatable. Specific elements of the modular assembly may further have noted configuration options, such as but not limited to, numbering various holes or mounting locations.

FIG. 38 generally illustrates an embodiment of an illustration in which mounting holes in various sub-components may be defined in order to quantify a particular configuration.

By way of example, the fifth hole down from the top in the posterior lateral strut may connect with the adjoining cross connector in its hole number 0. All elements of an entire socket assembly configuration may be defined with such a method. Additionally, there are general trends, which may be relatively common amongst various fittings and configurations. One such example may be that the top hole in the posterior lateral strut may generally connect with the swing webbing at that location. Trends also may occur when comparing limb size and shape with which connection points intersect. For instance, a limb that is large in circumference may generally have a longer span between the various struts through the cross connectors. Likewise, a limb that is smaller in circumference may generally have a shorter span between the various struts through the cross connectors. Similar trends may occur with respect to limb length and mounting locations of the distal band of connectors.

Because of the inherent trends, an algorithm may be used to correlate the defined configuration assembly to a limb circumference and/or length. Through using mathematical modeling, correlation algorithms, look up tables, artificial intelligence programs, or common sense, amongst other possible methods, a user may be able to input limb measurements and create an output assembly configuration suitable for such a limb size and shape, without a need to directly fit the device to the user to establish the same.

Such limb measurements may include, but not be limited to, proximal circumference, distal circumference, limb length from one or more of various relative distances along the limb, patient weight, scan of a limb, digitizing of a limb, tape measurements of a limb, or any other physical or electronic means of capturing limb size, shape, volume, soft tissue and skeletal anatomy, or other parameters.

The output of such a method may be at least one of any commonly used to illustrate data, but may include methods such as an App, Software, computer generated output, computer generated illustration, illustration, picture, virtual reality, or know-how, amongst others. In one embodiment, in the case of utilizing an App or Software, FIGS. 39A-39C generally illustrate a possible workflow of how a user may input variables into such system, and result in an output.

Such as system may as well be used for: ordering a device in a particular assembly configuration based on measurements, used for assembling a device in a particular configuration based on measurements, defining additional subcomponents desired in a particular configuration, storing of user data or patient specific data, documentation of user data or patient specific data, tracking utilization of device, or other related information.

Upon actual assembly of such a device, based on measurements, an actual fitting on an end user may occur, and such a device may be further customized to fit to the actual user.

Final fitting configurations, which may account for later fitting adjustments that may be made on an actual user, may be input to such a system, and used for improving such algorithms. Self-learning algorithms, modified algorithms, or other methods may be used to continue to refine the accuracy of the measurement-defined assembly configuration to that of an actual fitting configuration on an actual end user.

Such a method may be used on any level of amputation, or fitting of any level or type of orthotic device through such a system.

In one embodiment illustrated in FIGS. 40A, 40B, and 40C, and similar to FIG. 1C, stabilizing unit 102 may generally be positioned near the adductor muscle group, and may generally contour over, in between, or near the hamstrings and adductor muscle groups. Stabilizing unit 102B may generally be positioned on the lateral aspect of the limb, and more specifically may be positioned along the posterior lateral aspect of the limb, and more specifically may be positioned between the hamstrings and lateral quadriceps in some configurations.

The proximal brim may utilize a generally compliant member or structure 200 to span between the stabilizing units 102 and 102B. The limb may generally be supported through these compliant members across the brim area of the socket, including medially and posteriorly. The anterior area of the brim may also use compliant materials to span there between, and more particularly may use an adjustable member 4002A along with in such area.

Between the two stabilizing units described, a floating member 4001 may be integrated, which may be used to capture and control the limb within the socket configuration. For example, such floating member may generally be positioned to sit just anterior to the distal cut end of the bone. Likewise, at least one of the stabilizing unit members may generally be positioned just posterior to the cut end of the bone. Or alternatively, such anchored and floating members may generally be positioned on either side of the such bone, whether anterior/posterior, posterior/anterior, medial/lateral, or other such combinations.

Through integrating such floating member 4001, and through adding an adjustability means or circumferential connector 4002B and or 4005, the floating member may be user-adjusted to capture and control the limb within the socket interior 4006.

Such floating member may be relatively short, or may be long in length. It may be connected just to the other anchored stabilizing unit members circumferentially, or may also be connected to the brim area proximally, or may also be connected distally to other compliant members. In a preferred embodiment though, the floating member may not be connected rigidly, but rather through "floating" it between rigid members through compliant materials may allow the floating member to be effectively wrapped around the limb and contour to match the underlying limb shape.

Such floating member may be specifically contoured to match the underlying anatomy, or may be a pre-determined shape. A pad may also be attached on its inside to allow it to press against the limb with more specific contouring.

On the posterior/medial side of the system, another floating member 4003 may be positioned generally near or in between the hamstrings and adductor muscle groups. Such floating member may also be connected through compliant materials 4004 to other members such as the brim area of compliant member or structure 200.

The floating members may use a material, which generally can hold its form, but may be relatively flexible or rigid in nature. As the circumferential connectors 4005 and 4002B are tightened around the limb, the floating member may generally press against the underlying limb and help prevent the circumferential connectors from roping into the limb tissue.

In one embodiment, a compliant connector may provide a common mounting connector for various stabilizing members and floating members, providing a visual 'distal end' to the socket. In such a configuration, the socket may offer a low profile cosmetic appearance about the underlying limb, by effectively eliminating any potential socket bulk along the anterior/lateral aspects of the socket. Through positioning the anchored stabilizing unit members as positionally opposing each other, the socket can also achieve a narrower medial/lateral dimension, thus more effectively capturing the underlying bony anatomy and provide greater control within the device.

The invention therefor contemplates a transfemoral level prosthetic socket apparatus for attaching a prosthetic to a limb of a user comprising: a first stabilizer unit having a first proximal end and a first distal end first end and adapted to be perpendicularly positioned near an adductor muscle group of said user; a second stabilizer unit having a second proximal end and a second distal end and adapted to be perpendicularly positioned between a hamstring and a lateral quadriceps of said user; a proximal brim made of a complaint material spanning from said first proximal end of said first stabilizer to said second proximal end of said second stabilizer and adapted to support said limb; a first adjustable member having a length located opposite of said proximal brim and spanning from said first proximal end of said first stabilizer to said second proximal end of said second stabilizer wherein said length is adjustable; a floating member having a third proximal end and a third distal end perpendicularly positioned between said first stabilizer and said second stabilizer opposite and below said proximal brim and adapted capture and control said limb within said socket; and a second adjustable member having a first end attached to said first stabilizer, a second end attached to said second stabilizer, and a length attached to said floating member wherein said second adjustable member is adapted to be adjustable in length.

It is further understood that the use of such a system has the potential to functionally eliminate the need for expensive machinery commonly used to fabricate conventional prosthetics, and reduce the toolset down to simple hand tools such as Allen wrenches for example. Furthermore, the use of such a system has the potential to functionally eliminate the need for a highly trained and skilled clinician to fit a prosthetic socket for instance, as much or all of a defined and successful fit may be defined through an algorithm, or the like.

What is claimed is:

1. A prosthetic interface system using compliant members, comprising:

a proximal medial connector connecting two medial floating members;

the two medial floating members configured to be attached to a flexible member on a user side, wherein a proximal end of each medial floating member has a gradual tapering of relative stiffness, wherein at least one of the two medial floating members is modularly connected to a dynamic tab;

the dynamic tab configured to provide 360 degree rotation;

a proximal medial swing strap, wherein the proximal medial swing strap incorporates hook and loop fastener for connecting a pad;

a cross connector located on a medial distal aspect of a socket, wherein the cross connector is configured to adjust an angle and a span of the two medial floating members;

a proximal posterior cross connector configured to adjust an amount of suspension of the proximal medial swing strap;

a lateral proximal cross connector configured to prevent one or more anchor members from splaying apart under load;

a distal lateral cross connector configured to be positioned proximal to a bottom of a limb of a user, wherein a pad is configured to be placed between the distal lateral cross connector and the limb of the user;

one or more anterior connectors configured to be incrementally adjusted for circumferential tightness; and markings displayed on each of the connectors to quantify relative positions of the connectors.

2. The prosthetic interface system of claim 1, wherein the pad comprises more than one durometer.

3. The prosthetic interface system of claim 2, wherein an outer surface of the pad comprises a higher durometer, and an inner surface of the pad comprises a lower durometer.

4. The prosthetic interface system of claim 3, wherein the outer surface of the pad comprises raised geometric shapes.

5. The prosthetic interface system of claim 4, wherein the raised geometric shapes are configured by an angulation to compress in a direction, and configured by the angulation to expand in an opposite direction.

6. The prosthetic interface system of claim 1, further comprising:

a compliant member comprising asymmetrical contouring and concavity, wherein the compliant member has a reversible design such that one curvature is configured to be positioned on a distal aspect.

* * * * *